United States Patent
Katahira et al.

(10) Patent No.: US 10,533,169 B2
(45) Date of Patent: Jan. 14, 2020

(54) PROTEIN HAVING XYLOSE ISOMERASE ACTIVITY AND USE OF SAME

(71) Applicants: KABUSHIKI KAISHA TOYOTA CHUO KENKYUSHO, Nagakute-shi, Aichi-ken (JP); TOYOTA JIDOSHA KABUSHIKI KAISHA, Toyota-shi, Aichi-ken (JP)

(72) Inventors: Satoshi Katahira, Nagoya (JP); Risa Nagura, Toyota (JP); Kenro Tokuhiro, Aichi-gun (JP); Nobuhiro Ishida, Seto (JP); Chie Imamura, Nagoya (JP); Toru Onishi, Toyota (JP); Noriko Yasutani, Nagoya (JP); Nobuki Tada, Nisshin (JP)

(73) Assignees: KABUSHIKI KAISHA TOYOTA CHUO KENKYUSHO, Nagakute-shi (JP); TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/020,273

(22) Filed: Jun. 27, 2018

(65) Prior Publication Data

US 2018/0298369 A1    Oct. 18, 2018

Related U.S. Application Data

(62) Division of application No. 14/780,987, filed as application No. PCT/JP2014/001849 on Mar. 28, 2014, now Pat. No. 10,036,005.

(30) Foreign Application Priority Data

Mar. 28, 2013 (JP) ................................. 2013-070584
Feb. 12, 2014 (JP) ................................. 2014-024878

(51) Int. Cl.
    *C12N 9/92*    (2006.01)
    *C12N 15/81*   (2006.01)
    *C12P 7/06*    (2006.01)

(52) U.S. Cl.
    CPC .............. *C12N 9/92* (2013.01); *C12N 15/81* (2013.01); *C12P 7/06* (2013.01); *C12Y 503/01005* (2013.01); *Y02E 50/17* (2013.01)

(58) Field of Classification Search
None
See application file for complete search history.

(56) References Cited

U.S. PATENT DOCUMENTS

| | | |
|---|---|---|
| 7,622,284 B2 | 11/2009 | Op Den Camp et al. |
| 2008/0014620 A1 | 1/2008 | Op Den Camp et al. |
| 2010/0035306 A1 | 2/2010 | Op Den Camp et al. |
| 2010/0199387 A1 | 8/2010 | Yoshizumi et al. |
| 2011/0269180 A1 | 11/2011 | Brat et al. |
| 2012/0064607 A1 | 3/2012 | Op Den Camp et al. |
| 2013/0084617 A1 | 4/2013 | Op Den Camp et al. |
| 2013/0095538 A1 | 4/2013 | Katahira et al. |
| 2015/0031076 A1 | 1/2015 | Op Den Camp et al. |
| 2015/0099276 A1 | 4/2015 | Brat et al. |
| 2016/0002674 A1 | 1/2016 | Onishi et al. |

FOREIGN PATENT DOCUMENTS

| | | |
|---|---|---|
| JP | 2006-525029 A | 11/2006 |
| JP | 2008-079564 A | 4/2008 |
| JP | 4334352 B2 | 9/2009 |
| JP | 2011-147445 A | 8/2011 |
| JP | 2014-193152 A | 10/2014 |
| WO | 2004/099381 A2 | 11/2004 |
| WO | 2008/120410 A1 | 10/2008 |
| WO | 2010/000464 A1 | 1/2010 |
| WO | 2010/070549 A1 | 6/2010 |
| WO | 2011/150313 A1 | 12/2011 |
| WO | 2013/003219 A1 | 1/2013 |
| WO | 2014/133092 A1 | 9/2014 |

OTHER PUBLICATIONS

Lee et al.; "Directed Evolution of Xylose Isomerase for Improved Xylose Catabolism and Fermentation in the Yeast *Saccharomyces cerevisiae*;" Appl. Environ. Microbial.; Aug. 2012; vol. 78, No. 16; pp. 5708-5716.
Database Geneseq [Online]; "Ruminococcus flavefaciens mutant xylose isomerase (RF_XI) variant 60;" Feb. 28, 2013; XP002725321.
Jun. 17, 2014 International Search Report issued in International Patent Application No. PCT/JP2014/001849.
Jan. 26, 2016 Office Action issued in Japanese Patent Application No. 2014-024878.
Jul. 19, 2016 Office Action issued in Japanese Patent Application No. 2014-024878.
Oct. 31, 2017 Office Action issued in Chinese Patent Application No. 201480017949.0.
Dec. 1, 2017 Office Action issued in U.S Appl. No. 14/780,987.
Jun. 28, 2017 Office Action issued in U.S. Appl. No. 14/780,987.

*Primary Examiner* — Anand U Desai
(74) *Attorney, Agent, or Firm* — Oliff PLC

(57) ABSTRACT

A eukaryotic cell having xylose utilization ability. Provided is a protein that has xylose isomerase activity and has an amino acid sequence including, when aligned with an amino acid sequence expressed by SEQ ID NO:1, the 1st to 6th motifs expressed respectively by SEQ ID NOs:2 to 7 from the N-terminus side in the order described, and having, in place of asparagine (N) in an amino acid sequence of the 6th motif, another amino acid.

10 Claims, 9 Drawing Sheets

Specification includes a Sequence Listing.

⟨XI having activity in Yeast⟩

| Strain | Symbol | Identity | Reference |
|---|---|---|---|
| Clostridium phytofermentans | Cp | 63 | AEM 2009, 75(8):2304-2311 |
| Clostridium difficile | Cd | 57 | US 2011/0318790 |
| Fusobacterium mortiferum | Fm | 56 | US 2011/0318790 |
| Bacteroides thetaiotaomicron | Bt | 53 | WO2006009434 |
| Cyllamyces aberensis | Ca | 51 | US 2011/0318790 |
| Bacteroides fragilis | Bf | 51 | US 2011/0318790 |
| Orpinomyces sp. ukk1 | Or | 51 | AMB 2009, 82(6):1067-78 |
| Piromyces sp. E2 | Pi | 51 | JP4334352 |
| Lactococcus lactis | Ll | 50 | WO2010070549 |
| Ciona intestinalis | Ci | 46 | US 2011/0318790 |

Identities to amino acid sequence of RSXI

| | Motif 1 | Motif 2 | Motif 3 | Motif 4 | Motif 5 | Motif 6 | Overall |
|---|---|---|---|---|---|---|---|
| Cp | 95 | 95 | 91 | 80 | 90 | 77 | 63 |
| Fm | 90 | 86 | 86 | 76 | 90 | 78 | 56 |
| Ll | 85 | 65 | 73 | 80 | 81 | 72 | 50 |
| Cd | 85 | 86 | 86 | 80 | 90 | 72 | 57 |
| Bt | 80 | 82 | 82 | 71 | 72 | 72 | 51 |
| Ci | 75 | 78 | 73 | 80 | 90 | 77 | 46 |
| Ca | 75 | 82 | 82 | 71 | 72 | 67 | 51 |
| Or | 75 | 82 | 82 | 71 | 72 | 67 | 51 |
| Pi | 75 | 82 | 82 | 71 | 72 | 67 | 51 |
| Bf | 80 | 82 | 78 | 71 | 72 | 61 | 51 |

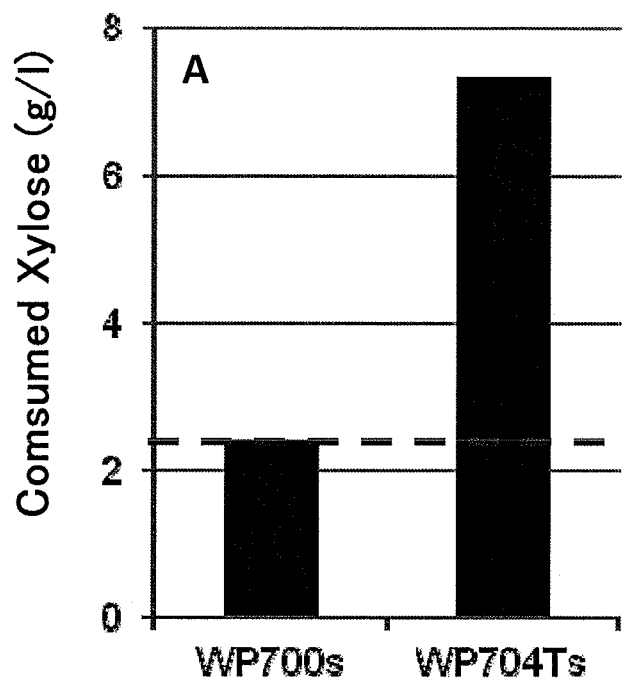
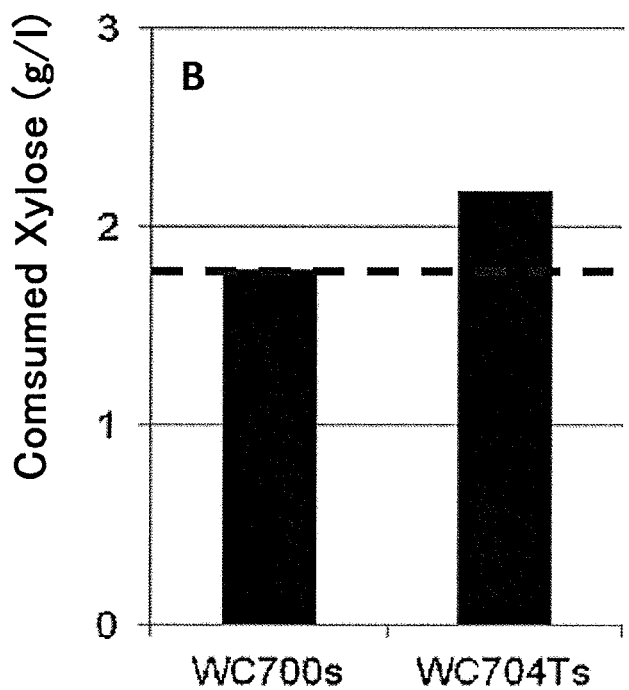
Fig.8

SEQUENCE LISTING

<160> NUMBER OF SEQ ID NOS: 105

<210> SEQ ID NO 1
<211> LENGTH: 439
<212> TYPE: PRT
<213> ORGANISM: Reticulitermis speratus

<400> SEQUENCE: 1

```
Met Ser Gln Ile Phe Lys Asp Ile Pro Val Ile Lys Tyr Glu Gly Pro
1               5                   10                  15

Ala Ser Lys Asn Pro Leu Ser Phe Lys Tyr Tyr Asp Ala Asn Lys Val
            20                  25                  30

Ile Asp Gly Lys Pro Met Lys Glu His Leu Arg Tyr Ala Met Ala Trp
        35                  40                  45

Trp His Asn Leu Cys Ala Thr Gly Gln Asp Met Phe Gly Pro Gly Thr
    50                  55                  60

Ala Asp Lys Ser Phe Gly Ser Lys Thr Val Gly Thr Met Glu His Ala
65                  70                  75                  80

His Ala Lys Val Asp Ala Gly Phe Glu Phe Met Ser Lys Leu Gly Val
                85                  90                  95

Glu Tyr Phe Cys Phe His Asp Ala Asp Leu Val Pro Glu Ala Asp Thr
            100                 105                 110

Leu Ser Glu Thr Asn Lys Arg Leu Asp Glu Ile Ala Glu His Ile Val
        115                 120                 125

Ala Lys Gln Lys Ala Thr Gly Ile Lys Cys Leu Trp Gly Thr Ala Asn
    130                 135                 140

Leu Phe Ser Asn Pro Arg Phe Leu Asn Gly Ser Gly Ser Ser Asn Ser
145                 150                 155                 160

Ala Asp Val Tyr Ala Tyr Ala Ala Gln Ile Lys Lys Ala Leu Asp
                165                 170                 175

Leu Thr Val Lys Phe Gly Gly Val Gly Tyr Val Phe Trp Gly Gly Arg
            180                 185                 190

Glu Gly Tyr Glu Thr Leu Leu Asn Thr Asp Val Lys Phe Glu Gln Glu
        195                 200                 205

Asn Ile Ala Asn Leu Met His Leu Ala Val Thr Tyr Gly Arg Ser Ile
    210                 215                 220

Gly Phe Lys Gly Asp Phe Tyr Ile Glu Pro Lys Pro Lys Glu Pro Thr
225                 230                 235                 240

Lys His Gln Tyr Asp Phe Asp Ala Ala Thr Thr Ile Gly Phe Ile Arg
                245                 250                 255

Gln Tyr Gly Leu Glu Lys Asp Phe Lys Leu Asn Ile Glu Ala Asn His
            260                 265                 270

Ala Thr Leu Ala Gly His Thr Phe Gln His Asp Leu Arg Ile Ser Ala
        275                 280                 285

Ile Asn Gly Met Leu Gly Ser Val Asp Ala Asn Thr Gly Asp Pro Leu
    290                 295                 300

Leu Gly Trp Asp Thr Asp Glu Phe Pro Tyr Ser Val Tyr Asp Thr Thr
305                 310                 315                 320

Leu Ala Met Tyr Glu Ile Ile Lys Ala Gly Gly Leu Thr Gly Gly Leu
                325                 330                 335

Asn Phe Asp Ser Lys Val Arg Arg Pro Ser Tyr Thr His Glu Asp Leu
            340                 345                 350

Phe Tyr Gly Phe Ile Leu Gly Met Asp Ser Phe Ala Leu Gly Leu Ile
        355                 360                 365
```

```
Lys Ala Lys Ala Leu Ile Ala Asp Gly Arg Leu Asp Ser Phe Val Lys
    370                 375                 380

Asp Arg Tyr Ala Ser Tyr Gly Ser Gly Ile Gly Ala Lys Ile Arg Asp
385                 390                 395                 400

His Ser Ala Thr Leu Glu Glu Leu Ala Ala Tyr Ala Leu Ala Lys Asp
                405                 410                 415

Thr Val Ala Leu Pro Gly Ser Gly Arg Gln Glu Tyr Leu Glu Ser Ile
            420                 425                 430

Ile Asn Gln Ile Leu Phe Gln
        435

<210> SEQ ID NO 2
<211> LENGTH: 18
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (2)..(2)
<223> OTHER INFORMATION: Xaa can be any naturally occuring amino acid,
      or preperably D or E
<220> FEATURE:
<221> NAME/KEY: MISC_FEATURE
<222> LOCATION: (3)..(3)
<223> OTHER INFORMATION: Xaa can be any naturally occuring amino acid,
      or preperably F or I or L or M
<220> FEATURE:
<221> NAME/KEY: MISC_FEATURE
<222> LOCATION: (4)..(4)
<223> OTHER INFORMATION: Xaa can be any naturally occuring amino acid,
      or preperably A or C or F or I or L or M or Y
<220> FEATURE:
<221> NAME/KEY: MISC_FEATURE
<222> LOCATION: (5)..(5)
<223> OTHER INFORMATION: Xaa can be any naturally occuring amino acid,
      or preperably D or E or H or N or Q or S or T
<220> FEATURE:
<221> NAME/KEY: MISC_FEATURE
<222> LOCATION: (7)..(7)
<223> OTHER INFORMATION: Xaa can be any naturally occuring amino acid,
      or preperably L or M
<220> FEATURE:
<221> NAME/KEY: MISC_FEATURE
<222> LOCATION: (8)..(8)
<223> OTHER INFORMATION: Xaa can be any naturally occuring amino acid,
      or preperably D or G or N or S
<220> FEATURE:
<221> NAME/KEY: MISC_FEATURE
<222> LOCATION: (9)..(9)
<223> OTHER INFORMATION: Xaa can be any naturally occuring amino acid,
      or preperably A or I or L or T or V
<220> FEATURE:
<221> NAME/KEY: MISC_FEATURE
<222> LOCATION: (10)..(10)
<223> OTHER INFORMATION: Xaa can be any naturally occuring amino acid,
      or preperably D or E or G or K or P
<220> FEATURE:
<221> NAME/KEY: MISC_FEATURE
<222> LOCATION: (11)..(11)
<223> OTHER INFORMATION: Xaa can be any naturally occuring amino acid,
      or preperably F or H or Y
<220> FEATURE:
<221> NAME/KEY: MISC_FEATURE
<222> LOCATION: (12)..(12)
<223> OTHER INFORMATION: Xaa can be any naturally occuring amino acid,
      or preperably F or L or W or Y
<220> FEATURE:
<221> NAME/KEY: MISC_FEATURE
<222> LOCATION: (13)..(13)
<223> OTHER INFORMATION: Xaa can be any naturally occuring amino acid,
      or preperably A or C or S or T
<220> FEATURE:
<221> NAME/KEY: MISC_FEATURE
```

```
<222> LOCATION: (14)..(14)
<223> OTHER INFORMATION: Xaa can be any naturally occuring amino acid,
      or preperably F or W
<220> FEATURE:
<221> NAME/KEY: MISC_FEATURE
<222> LOCATION: (17)..(17)
<223> OTHER INFORMATION: Xaa can be any naturally occuring amino acid,
      or preperably A or I or K or R or T or V

<400> SEQUENCE: 2

Phe Xaa Xaa Xaa Xaa Lys Xaa Xaa Xaa Xaa Xaa Xaa Xaa Xaa His Asp
1               5                   10                  15

Xaa Asp

<210> SEQ ID NO 3
<211> LENGTH: 20
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (1)..(1)
<223> OTHER INFORMATION: Xaa can be any naturally occurring amino acid,
      or preferably@D or G or K or N
<220> FEATURE:
<221> NAME/KEY: MISC_FEATURE
<222> LOCATION: (2)..(2)
<223> OTHER INFORMATION: Xaa can be any naturally occurring amino acid,
      or preferably@A or G or S
<220> FEATURE:
<221> NAME/KEY: MISC_FEATURE
<222> LOCATION: (3)..(3)
<223> OTHER INFORMATION: Xaa can be any naturally occurring amino acid,
      or preferably@A or E or K or Q or S or T or V
<220> FEATURE:
<221> NAME/KEY: MISC_FEATURE
<222> LOCATION: (4)..(4)
<223> OTHER INFORMATION: Xaa can be any naturally occurring amino acid,
      or preferably@G or N
<220> FEATURE:
<221> NAME/KEY: MISC_FEATURE
<222> LOCATION: (5)..(5)
<223> OTHER INFORMATION: Xaa can be any naturally occurring amino acid,
      or preferably@F or Y
<220> FEATURE:
<221> NAME/KEY: MISC_FEATURE
<222> LOCATION: (6)..(6)
<223> OTHER INFORMATION: Xaa can be any naturally occurring amino acid,
      or preferably@V or T
<220> FEATURE:
<221> NAME/KEY: MISC_FEATURE
<222> LOCATION: (7)..(7)
<223> OTHER INFORMATION: Xaa can be any naturally occurring amino acid,
      or preferably@F or L
<220> FEATURE:
<221> NAME/KEY: MISC_FEATURE
<222> LOCATION: (15)..(15)
<223> OTHER INFORMATION: Xaa can be any naturally occurring amino acid,
      or preferably@A or D or E or H or M
<220> FEATURE:
<221> NAME/KEY: MISC_FEATURE
<222> LOCATION: (16)..(16)
<223> OTHER INFORMATION: Xaa can be any naturally occurring amino acid,
      or preferably@C or N or S or T
<220> FEATURE:
<221> NAME/KEY: MISC_FEATURE
<222> LOCATION: (16)..(16)
<223> OTHER INFORMATION: Xaa can be any naturally occurring amino acid,
      or preferably@
<220> FEATURE:
<221> NAME/KEY: MISC_FEATURE
<222> LOCATION: (18)..(18)
<223> OTHER INFORMATION: Xaa can be any naturally occurring amino acid,
      or preferably H or L or W
```

```
<400> SEQUENCE: 3

Xaa Xaa Xaa Xaa Xaa Xaa Xaa Trp Gly Gly Arg Glu Gly Tyr Xaa Xaa
1               5                   10                  15

Leu Xaa Asn Thr
            20

<210> SEQ ID NO 4
<211> LENGTH: 23
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (1)..(1)
<223> OTHER INFORMATION: Xaa can be any naturally occurring amino acid,
      or preferably G or N
<220> FEATURE:
<221> NAME/KEY: MISC_FEATURE
<222> LOCATION: (2)..(2)
<223> OTHER INFORMATION: Xaa can be any naturally occurring amino acid,
      or preferably F or H or Y
<220> FEATURE:
<221> NAME/KEY: MISC_FEATURE
<222> LOCATION: (3)..(3)
<223> OTHER INFORMATION: Xaa can be any naturally occurring amino acid,
      or preferably D or E or K or L or N or Q or R or T
<220> FEATURE:
<221> NAME/KEY: MISC_FEATURE
<222> LOCATION: (4)..(4)
<223> OTHER INFORMATION: Xaa can be any naturally occurring amino acid,
      or preferably G or P
<220> FEATURE:
<221> NAME/KEY: MISC_FEATURE
<222> LOCATION: (5)..(5)
<223> OTHER INFORMATION: Xaa can be any naturally occurring amino acid,
      or preferably A or D or I or N or Q or T
<220> FEATURE:
<221> NAME/KEY: MISC_FEATURE
<222> LOCATION: (6)..(6)
<223> OTHER INFORMATION: Xaa can be any naturally occurring amino acid,
      or preferably F or L or M
<220> FEATURE:
<221> NAME/KEY: MISC_FEATURE
<222> LOCATION: (7)..(7)
<223> OTHER INFORMATION: Xaa can be any naturally occurring amino acid,
      or preferably F or L or Y
<220> FEATURE:
<221> NAME/KEY: MISC_FEATURE
<222> LOCATION: (8)..(8)
<223> OTHER INFORMATION: Xaa can be any naturally occurring amino acid,
      or preferably I or L
<220> FEATURE:
<221> NAME/KEY: MISC_FEATURE
<222> LOCATION: (13)..(13)
<223> OTHER INFORMATION: Xaa can be any naturally occurring amino acid,
      or preferably K or M or Q
<220> FEATURE:
<221> NAME/KEY: MISC_FEATURE
<222> LOCATION: (16)..(16)
<223> OTHER INFORMATION: Xaa can be any naturally occurring amino acid,
      or preferably M or S or T
<220> FEATURE:
<221> NAME/KEY: MISC_FEATURE
<222> LOCATION: (17)..(17)
<223> OTHER INFORMATION: Xaa can be any naturally occurring amino acid,
      or preferably K or S or T
<220> FEATURE:
<221> NAME/KEY: MISC_FEATURE
<222> LOCATION: (22)..(22)
<223> OTHER INFORMATION: Xaa can be any naturally occurring amino acid,
      or preferably F or T or V or Y

<400> SEQUENCE: 4

Xaa Xaa Xaa Xaa Xaa Xaa Xaa Xaa Glu Pro Lys Pro Xaa Glu Pro Xaa
```

```
1               5                   10                  15

Xaa His Gln Tyr Asp Xaa Asp
            20
```

<210> SEQ ID NO 5
<211> LENGTH: 23
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (2)..(2)
<223> OTHER INFORMATION: Xaa can be any naturally occurring amino acid,
      or preferably D or E or K or L or N or Q
<220> FEATURE:
<221> NAME/KEY: MISC_FEATURE
<222> LOCATION: (3)..(3)
<223> OTHER INFORMATION: Xaa can be any naturally occurring amino acid,
      or preferably D or E or G or K or N or P or Q
<220> FEATURE:
<221> NAME/KEY: MISC_FEATURE
<222> LOCATION: (4)..(4)
<223> OTHER INFORMATION: Xaa can be any naturally occurring amino acid,
      or preferably D or E or H or Y
<220> FEATURE:
<221> NAME/KEY: MISC_FEATURE
<222> LOCATION: (5)..(5)
<223> OTHER INFORMATION: Xaa can be any naturally occurring amino acid,
      or preferably F or I or V
<220> FEATURE:
<221> NAME/KEY: MISC_FEATURE
<222> LOCATION: (6)..(6)
<223> OTHER INFORMATION: Xaa can be any naturally occurring amino acid,
      or preferably K or R
<220> FEATURE:
<221> NAME/KEY: MISC_FEATURE
<222> LOCATION: (7)..(7)
<223> OTHER INFORMATION: Xaa can be any naturally occurring amino acid,
      or preferably F or I or L or M or V
<220> FEATURE:
<221> NAME/KEY: MISC_FEATURE
<222> LOCATION: (9)..(9)
<223> OTHER INFORMATION: Xaa can be any naturally occurring amino acid,
      or preferably I or L
<220> FEATURE:
<221> NAME/KEY: MISC_FEATURE
<222> LOCATION: (11)..(11)
<223> OTHER INFORMATION: Xaa can be any naturally occurring amino acid,
      or preferably A or G or P or T or V
<220> FEATURE:
<221> NAME/KEY: MISC_FEATURE
<222> LOCATION: (14)..(14)
<223> OTHER INFORMATION: Xaa can be any naturally occurring amino acid,
      or preferably A or T
<220> FEATURE:
<221> NAME/KEY: MISC_FEATURE
<222> LOCATION: (15)..(15)
<223> OTHER INFORMATION: Xaa can be any naturally occurring amino acid,
      or preferably N or T or W
<220> FEATURE:
<221> NAME/KEY: MISC_FEATURE
<222> LOCATION: (17)..(17)
<223> OTHER INFORMATION: Xaa can be any naturally occurring amino acid,
      or preferably A or S
<220> FEATURE:
<221> NAME/KEY: MISC_FEATURE
<222> LOCATION: (18)..(18)
<223> OTHER INFORMATION: Xaa can be any naturally occurring amino acid,
      or preferably F or G or Q
<220> FEATURE:
<221> NAME/KEY: MISC_FEATURE
<222> LOCATION: (20)..(20)
<223> OTHER INFORMATION: Xaa can be any naturally occurring amino acid,
      or preferably C or D or S or T
<220> FEATURE:
<221> NAME/KEY: MISC_FEATURE

```
<222> LOCATION: (21)..(21)
<223> OTHER INFORMATION: Xaa can be any naturally occurring amino acid,
      or preferably F or H or M or Y
<220> FEATURE:
<221> NAME/KEY: MISC_FEATURE
<222> LOCATION: (22)..(22)
<223> OTHER INFORMATION: Xaa can be any naturally occurring amino acid,
      or preferably D or E or H or M or Q

<400> SEQUENCE: 5

Leu Xaa Xaa Xaa Xaa Xaa Xaa Asn Xaa Glu Xaa Asn His Xaa Xaa Leu
1               5                   10                  15

Xaa Xaa His Xaa Xaa Xaa His
            20

<210> SEQ ID NO 6
<211> LENGTH: 21
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (1)..(1)
<223> OTHER INFORMATION: Xaa can be any naturally occurring amino acid,
      or preferably F or L
<220> FEATURE:
<221> NAME/KEY: MISC_FEATURE
<222> LOCATION: (4)..(4)
<223> OTHER INFORMATION: Xaa can be any naturally occurring amino acid,
      or preferably I or L or V
<220> FEATURE:
<221> NAME/KEY: MISC_FEATURE
<222> LOCATION: (6)..(6)
<223> OTHER INFORMATION: Xaa can be any naturally occurring amino acid,
      or preferably A or S
<220> FEATURE:
<221> NAME/KEY: MISC_FEATURE
<222> LOCATION: (8)..(8)
<223> OTHER INFORMATION: Xaa can be any naturally occurring amino acid,
      or preferably M or Q or R or T
<220> FEATURE:
<221> NAME/KEY: MISC_FEATURE
<222> LOCATION: (10)..(10)
<223> OTHER INFORMATION: Xaa can be any naturally occurring amino acid,
      or preferably D or H or N or S
<220> FEATURE:
<221> NAME/KEY: MISC_FEATURE
<222> LOCATION: (11)..(11)
<223> OTHER INFORMATION: Xaa can be any naturally occurring amino acid,
      or preferably A or K or L or M or P or T or V or Y
<220> FEATURE:
<221> NAME/KEY: MISC_FEATURE
<222> LOCATION: (12)..(12)
<223> OTHER INFORMATION: Xaa can be any naturally occurring amino acid,
      or preferably L or N or Q or D
<220> FEATURE:
<221> NAME/KEY: MISC_FEATURE
<222> LOCATION: (13)..(13)
<223> OTHER INFORMATION: Xaa can be any naturally occurring amino acid,
      or preferably I or L or N
<220> FEATURE:
<221> NAME/KEY: MISC_FEATURE
<222> LOCATION: (17)..(17)
<223> OTHER INFORMATION: Xaa can be any naturally occurring amino acid,
      or preferably I or T
<220> FEATURE:
<221> NAME/KEY: MISC_FEATURE
<222> LOCATION: (19)..(19)
<223> OTHER INFORMATION: Xaa can be any naturally occurring amino acid,
      or preferably E or Q
<220> FEATURE:
<221> NAME/KEY: MISC_FEATURE
<222> LOCATION: (20)..(20)
<223> OTHER INFORMATION: Xaa can be any naturally occurring amino acid,
      or preferably F or Y
```

```
<400> SEQUENCE: 6

Xaa Gly Ser Xaa Asp Xaa Asn Xaa Gly Xaa Xaa Xaa Xaa Gly Trp Asp
1               5                   10                  15

Xaa Asp Xaa Xaa Pro
            20

<210> SEQ ID NO 7
<211> LENGTH: 11
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (3)..(3)
<223> OTHER INFORMATION: Xaa can be any naturally o ccurring amino acid,
      or preferably F or I or L or M or T or V
<220> FEATURE:
<221> NAME/KEY: MISC_FEATURE
<222> LOCATION: (7)..(7)
<223> OTHER INFORMATION: Xaa can be any naturally o ccurring amino acid,
      or preferably A or C or S or T
<220> FEATURE:
<221> NAME/KEY: MISC_FEATURE
<222> LOCATION: (9)..(9)
<223> OTHER INFORMATION: Xaa can be any naturally o ccurring amino acid,
      or preferably I or L or P or T or V

<400> SEQUENCE: 7

Gly Gly Xaa Asn Phe Asp Xaa Lys Xaa Arg Arg
1               5                   10

<210> SEQ ID NO 8
<211> LENGTH: 18
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (2)..(2)
<223> OTHER INFORMATION: Xaa can be any naturally occurring amino acid,
      or preferably D or E
<220> FEATURE:
<221> NAME/KEY: MISC_FEATURE
<222> LOCATION: (3)..(3)
<223> OTHER INFORMATION: Xaa can be any naturally occurring amino acid,
      or preferably F or I or L
<220> FEATURE:
<221> NAME/KEY: MISC_FEATURE
<222> LOCATION: (4)..(4)
<223> OTHER INFORMATION: Xaa can be any naturally occurring amino acid,
      or preferably A or M
<220> FEATURE:
<221> NAME/KEY: MISC_FEATURE
<222> LOCATION: (5)..(5)
<223> OTHER INFORMATION: Xaa can be any naturally occurring amino acid,
      or preferably E or Q or S or T
<220> FEATURE:
<221> NAME/KEY: MISC_FEATURE
<222> LOCATION: (7)..(7)
<223> OTHER INFORMATION: Xaa can be any naturally occurring amino acid,
      or preferably L or M
<220> FEATURE:
<221> NAME/KEY: MISC_FEATURE
<222> LOCATION: (9)..(9)
<223> OTHER INFORMATION: Xaa can be any naturally occurring amino acid,
      or preferably I or V
<220> FEATURE:
<221> NAME/KEY: MISC_FEATURE
<222> LOCATION: (10)..(10)
<223> OTHER INFORMATION: Xaa can be any naturally occurring amino acid,
      or preferably E or G or K or P
```

```
<220> FEATURE:
<221> NAME/KEY: MISC_FEATURE
<222> LOCATION: (11)..(11)
<223> OTHER INFORMATION: Xaa can be any naturally occurring amino acid,
      or preferably F or H or Y
<220> FEATURE:
<221> NAME/KEY: MISC_FEATURE
<222> LOCATION: (12)..(12)
<223> OTHER INFORMATION: Xaa can be any naturally occurring amino acid,
      or preferably F or W or Y
<220> FEATURE:
<221> NAME/KEY: MISC_FEATURE
<222> LOCATION: (13)..(13)
<223> OTHER INFORMATION: Xaa can be any naturally occurring amino acid,
      or preferably C or T
<220> FEATURE:
<221> NAME/KEY: MISC_FEATURE
<222> LOCATION: (17)..(17)
<223> OTHER INFORMATION: Xaa can be any naturally occurring amino acid,
      or preferably A or I or K or R or V

<400> SEQUENCE: 8

Phe Xaa Xaa Xaa Xaa Lys Xaa Gly Xaa Xaa Xaa Xaa Xaa Phe His Asp
1               5                   10                  15

Xaa Asp

<210> SEQ ID NO 9
<211> LENGTH: 20
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (1)..(1)
<223> OTHER INFORMATION: Xaa can be any naturally occurring amino acid,
      or preferably G or N
<220> FEATURE:
<221> NAME/KEY: MISC_FEATURE
<222> LOCATION: (2)..(2)
<223> OTHER INFORMATION: Xaa can be any naturally occurring amino acid,
      or preferably A or G
<220> FEATURE:
<221> NAME/KEY: MISC_FEATURE
<222> LOCATION: (3)..(3)
<223> OTHER INFORMATION: Xaa can be any naturally occurring amino acid,
      or preferably V or K or E or T
<220> FEATURE:
<221> NAME/KEY: MISC_FEATURE
<222> LOCATION: (4)..(4)
<223> OTHER INFORMATION: Xaa can be any naturally occurring amino acid,
      or preferably G or N
<220> FEATURE:
<221> NAME/KEY: MISC_FEATURE
<222> LOCATION: (5)..(5)
<223> OTHER INFORMATION: Xaa can be any naturally occurring amino acid,
      or preferably F or Y
<220> FEATURE:
<221> NAME/KEY: MISC_FEATURE
<222> LOCATION: (15)..(15)
<223> OTHER INFORMATION: Xaa can be any naturally occurring amino acid,
      or preferably E or M or H
<220> FEATURE:
<221> NAME/KEY: MISC_FEATURE
<222> LOCATION: (16)..(16)
<223> OTHER INFORMATION: Xaa can be any naturally occurring amino acid,
      or preferably S or T

<400> SEQUENCE: 9

Xaa Xaa Xaa Xaa Xaa Val Phe Trp Gly Gly Arg Glu Gly Tyr Xaa Xaa
1               5                   10                  15

Leu Leu Asn Thr
            20
```

```
<210> SEQ ID NO 10
<211> LENGTH: 23
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (1)..(1)
<223> OTHER INFORMATION: Xaa can be any naturally occurring amino acid,
      or preferably G or N
<220> FEATURE:
<221> NAME/KEY: MISC_FEATURE
<222> LOCATION: (2)..(2)
<223> OTHER INFORMATION: Xaa can be any naturally occurring amino acid,
      or preferably F or H
<220> FEATURE:
<221> NAME/KEY: MISC_FEATURE
<222> LOCATION: (3)..(3)
<223> OTHER INFORMATION: Xaa can be any naturally occurring amino acid,
      or preferably K or D or T or E or L
<220> FEATURE:
<221> NAME/KEY: MISC_FEATURE
<222> LOCATION: (4)..(4)
<223> OTHER INFORMATION: Xaa can be any naturally occurring amino acid,
      or preferably G or P
<220> FEATURE:
<221> NAME/KEY: MISC_FEATURE
<222> LOCATION: (5)..(5)
<223> OTHER INFORMATION: Xaa can be any naturally occurring amino acid,
      or preferably D or Q or T or I
<220> FEATURE:
<221> NAME/KEY: MISC_FEATURE
<222> LOCATION: (7)..(7)
<223> OTHER INFORMATION: Xaa can be any naturally occurring amino acid,
      or preferably F or L or Y
<220> FEATURE:
<221> NAME/KEY: MISC_FEATURE
<222> LOCATION: (13)..(13)
<223> OTHER INFORMATION: Xaa can be any naturally occurring amino acid,
      or preferably K or M
<220> FEATURE:
<221> NAME/KEY: MISC_FEATURE
<222> LOCATION: (16)..(16)
<223> OTHER INFORMATION: Xaa can be any naturally occurring amino acid,
      or preferably M or S or T
<220> FEATURE:
<221> NAME/KEY: MISC_FEATURE
<222> LOCATION: (17)..(17)
<223> OTHER INFORMATION: Xaa can be any naturally occurring amino acid,
      or preferably K or T
<220> FEATURE:
<221> NAME/KEY: MISC_FEATURE
<222> LOCATION: (22)..(22)
<223> OTHER INFORMATION: Xaa can be any naturally occurring amino acid,
      or preferably F or V or Y

<400> SEQUENCE: 10

Xaa Xaa Xaa Xaa Xaa Phe Xaa Ile Glu Pro Lys Pro Xaa Glu Pro Xaa
1               5                   10                  15

Xaa His Gln Tyr Asp Xaa Asp
            20

<210> SEQ ID NO 11
<211> LENGTH: 23
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (2)..(2)
<223> OTHER INFORMATION: Xaa can be any naturally occurring amino acid,
      or preferably@D or E or N
<220> FEATURE:
```

```
<221> NAME/KEY: MISC_FEATURE
<222> LOCATION: (3)..(3)
<223> OTHER INFORMATION: Xaa can be any naturally occurring amino acid,
      or preferably K or Q
<220> FEATURE:
<221> NAME/KEY: MISC_FEATURE
<222> LOCATION: (4)..(4)
<223> OTHER INFORMATION: Xaa can be any naturally occurring amino acid,
      or preferably D or Y
<220> FEATURE:
<221> NAME/KEY: MISC_FEATURE
<222> LOCATION: (7)..(7)
<223> OTHER INFORMATION: Xaa can be any naturally occurring amino acid,
      or preferably I or L or M or V
<220> FEATURE:
<221> NAME/KEY: MISC_FEATURE
<222> LOCATION: (9)..(9)
<223> OTHER INFORMATION: Xaa can be any naturally occurring amino acid,
      or preferably I or L
<220> FEATURE:
<221> NAME/KEY: MISC_FEATURE
<222> LOCATION: (11)..(11)
<223> OTHER INFORMATION: Xaa can be any naturally occurring amino acid,
      or preferably A or P or T or V
<220> FEATURE:
<221> NAME/KEY: MISC_FEATURE
<222> LOCATION: (14)..(14)
<223> OTHER INFORMATION: Xaa can be any naturally occurring amino acid,
      or preferably A or T
<220> FEATURE:
<221> NAME/KEY: MISC_FEATURE
<222> LOCATION: (15)..(15)
<223> OTHER INFORMATION: Xaa can be any naturally occurring amino acid,
      or preferably T or W
<220> FEATURE:
<221> NAME/KEY: MISC_FEATURE
<222> LOCATION: (20)..(20)
<223> OTHER INFORMATION: Xaa can be any naturally occurring amino acid,
      or preferably C or T
<220> FEATURE:
<221> NAME/KEY: MISC_FEATURE
<222> LOCATION: (21)..(21)
<223> OTHER INFORMATION: Xaa can be any naturally occurring amino acid,
      or preferably F or H
<220> FEATURE:
<221> NAME/KEY: MISC_FEATURE
<222> LOCATION: (22)..(22)
<223> OTHER INFORMATION: Xaa can be any naturally occurring amino acid,
      or preferably Q or E

<400> SEQUENCE: 11

Leu Xaa Xaa Xaa Phe Lys Xaa Asn Xaa Glu Xaa Asn His Xaa Xaa Leu
1               5                   10                  15

Ala Gly His Xaa Xaa Xaa His
            20

<210> SEQ ID NO 12
<211> LENGTH: 21
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (1)..(1)
<223> OTHER INFORMATION: Xaa can be any naturally occurring amino acid,
      or preferably F or L
<220> FEATURE:
<221> NAME/KEY: MISC_FEATURE
<222> LOCATION: (4)..(4)
<223> OTHER INFORMATION: Xaa can be any naturally occurring amino acid,
      or preferably I or V
<220> FEATURE:
<221> NAME/KEY: MISC_FEATURE
<222> LOCATION: (6)..(6)
<223> OTHER INFORMATION: Xaa can be any naturally occurring amino acid,
```

```
      or preferably A or S
<220> FEATURE:
<221> NAME/KEY: MISC_FEATURE
<222> LOCATION: (8)..(8)
<223> OTHER INFORMATION: Xaa can be any naturally occurring amino acid,
      or preferably Q or R or T
<220> FEATURE:
<221> NAME/KEY: MISC_FEATURE
<222> LOCATION: (10)..(10)
<223> OTHER INFORMATION: Xaa can be any naturally occurring amino acid,
      or preferably D or N or S
<220> FEATURE:
<221> NAME/KEY: MISC_FEATURE
<222> LOCATION: (11)..(11)
<223> OTHER INFORMATION: Xaa can be any naturally occurring amino acid,
      or preferably L or M or P or Y
<220> FEATURE:
<221> NAME/KEY: MISC_FEATURE
<222> LOCATION: (12)..(12)
<223> OTHER INFORMATION: Xaa can be any naturally occurring amino acid,
      or preferably D or L or N or Q
<220> FEATURE:
<221> NAME/KEY: MISC_FEATURE
<222> LOCATION: (13)..(13)
<223> OTHER INFORMATION: Xaa can be any naturally occurring amino acid,
      or preferably L or N
<220> FEATURE:
<221> NAME/KEY: MISC_FEATURE
<222> LOCATION: (19)..(19)
<223> OTHER INFORMATION: Xaa can be any naturally occurring amino acid,
      or preferably E or Q

<400> SEQUENCE: 12

Xaa Gly Ser Xaa Asp Xaa Asn Xaa Gly Xaa Xaa Xaa Xaa Gly Trp Asp
1               5                   10                  15

Thr Asp Xaa Phe Pro
            20

<210> SEQ ID NO 13
<211> LENGTH: 11
<212> TYPE: PRT
<213> ORGANISM: Artificial
<220> FEATURE:
<223> OTHER INFORMATION: A consensus sequence in a Xylose isomerase
<220> FEATURE:
<221> NAME/KEY: MISC_FEATURE
<222> LOCATION: (3)..(3)
<223> OTHER INFORMATION: Xaa can be any naturally occurring amino acid,
      or preferably@F or I or L or T
<220> FEATURE:
<221> NAME/KEY: MISC_FEATURE
<222> LOCATION: (7)..(7)
<223> OTHER INFORMATION: Xaa can be any naturally occurring amino acid,
      or preferably A or C or S
<220> FEATURE:
<221> NAME/KEY: MISC_FEATURE
<222> LOCATION: (9)..(9)
<223> OTHER INFORMATION: Xaa can be any naturally occurring amino acid,
      or preferably T or V

<400> SEQUENCE: 13

Gly Gly Xaa Asn Phe Asp Xaa Lys Xaa Arg Arg
1               5                   10

<210> SEQ ID NO 14
<211> LENGTH: 438
<212> TYPE: PRT
<213> ORGANISM: Clostridium phytofermentans

<400> SEQUENCE: 14

Met Lys Asn Tyr Phe Pro Asn Val Pro Glu Val Lys Tyr Glu Gly Pro
1               5                   10                  15
```

```
Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Ala Asp Pro Phe Gly Val Thr Thr
        50                  55                  60

Met Asp Arg Thr Tyr Gly Asn Ile Thr Asp Pro Met Glu Leu Ala Lys
65                      70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
                100                 105                 110

Glu Glu Ser Lys Lys Asn Leu Phe Glu Ile Val Asp Tyr Ile Lys Glu
                115                 120                 125

Lys Met Asp Gln Thr Gly Ile Lys Leu Leu Trp Gly Thr Ala Asn Asn
        130                 135                 140

Phe Ser His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Lys Gly Tyr Val Phe Trp Gly Gly Arg Glu
        180                 185                 190

Gly Tyr Glu Thr Leu Leu Asn Thr Asp Leu Gly Leu Glu Leu Asp Asn
            195                 200                 205

Met Ala Arg Leu Met Lys Met Ala Val Glu Tyr Gly Arg Ala Asn Gly
210                 215                 220

Phe Asp Gly Asp Phe Tyr Ile Glu Pro Lys Pro Lys Glu Pro Thr Lys
225                 230                 235                 240

His Gln Tyr Asp Phe Asp Thr Ala Thr Val Leu Ala Phe Leu Arg Lys
                245                 250                 255

Tyr Gly Leu Glu Lys Asp Phe Lys Met Asn Ile Glu Ala Asn His Ala
            260                 265                 270

Thr Leu Ala Gly His Thr Phe Glu His Glu Leu Ala Met Ala Arg Val
        275                 280                 285

Asn Gly Ala Phe Gly Ser Val Asp Ala Asn Gln Gly Asp Pro Asn Leu
        290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Gly Phe Thr Asn Gly Gly Leu
                325                 330                 335

Asn Phe Asp Ala Lys Val Arg Arg Gly Ser Phe Glu Phe Asp Asp Ile
                340                 345                 350

Ala Tyr Gly Tyr Ile Ala Gly Met Asp Thr Phe Ala Leu Gly Leu Ile
            355                 360                 365

Lys Ala Ala Glu Ile Ile Asp Asp Gly Arg Ile Ala Lys Phe Val Asp
        370                 375                 380

Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Ser
                405                 410                 415

Glu Pro Val Met Gln Ser Gly Arg Gln Glu Val Leu Glu Thr Ile Val
                420                 425                 430

Asn Asn Ile Leu Phe Arg
```

435

<210> SEQ ID NO 15
<211> LENGTH: 445
<212> TYPE: PRT
<213> ORGANISM: Clostridium difficile

<400> SEQUENCE: 15

Met Ser Glu Ile Phe Lys Gly Ile Gly Gln Ile Lys Phe Glu Gly Val
1 5 10 15

Lys Ser Asp Asn Glu Leu Ala Phe Arg Tyr Tyr Asn Pro Glu Gln Val
20 25 30

Val Gly Asn Lys Thr Met Lys Glu His Leu Arg Phe Ala Met Ser Tyr
35 40 45

Trp His Thr Leu Cys Gly Glu Gly Asn Asp Pro Phe Gly Val Gly Thr
50 55 60

Val Glu Arg Pro Trp Asn Asn Val Thr Asp Pro Ile Glu Ile Ala Lys
65 70 75 80

Ile Lys Val Asp Ala Gly Phe Glu Phe Met Ser Lys Met Gly Ile Glu
85 90 95

Tyr Phe Cys Phe His Asp Arg Asp Ile Ala Pro Glu Gly Arg Asp Leu
100 105 110

Glu Glu Thr Asn Lys Ile Leu Asp Glu Ile Val Glu Tyr Ile Lys Val
115 120 125

Asn Met Glu Lys Thr Gly Ile Lys Leu Leu Trp Gly Thr Ala Asn Met
130 135 140

Phe Gly Asn Pro Arg Phe Val His Gly Ala Ser Thr Thr Cys Asn Ala
145 150 155 160

Asp Val Tyr Ala Tyr Ala Ala Ala Gln Val Lys Lys Ala Met Glu Ile
165 170 175

Thr Lys Tyr Leu Gly Gly Glu Asn Phe Val Phe Trp Gly Gly Arg Glu
180 185 190

Gly Tyr Glu Thr Leu Leu Asn Thr Asn Thr Glu Leu Glu Met Asp Asn
195 200 205

Phe Ala Arg Phe Leu Gln Met Ala Val Asp Tyr Ala Lys Glu Ile Gly
210 215 220

Phe Thr Gly Gln Phe Leu Ile Glu Pro Lys Pro Lys Glu Pro Thr Lys
225 230 235 240

His Gln Tyr Asp Phe Asp Thr Ala Thr Val Leu Gly Phe Leu Arg Lys
245 250 255

Tyr Asn Leu Asp Lys Tyr Phe Lys Met Asn Ile Glu Ala Asn His Ala
260 265 270

Thr Leu Ala Gly His Thr Phe Gln His Glu Leu Asn Ile Ala Arg Ile
275 280 285

Asn Asn Val Leu Gly Ser Ile Asp Ala Asn Gln Gly Asp Leu Leu Leu
290 295 300

Gly Trp Asp Thr Asp Gln Phe Pro Thr Asn Ile Tyr Asp Ala Thr Leu
305 310 315 320

Ala Met Tyr Glu Val Leu Lys Gln Gly Gly Ile Ala Pro Gly Gly Phe
325 330 335

Asn Phe Asp Ser Lys Val Arg Arg Ala Ser Phe Glu Val Glu Asp Leu
340 345 350

Phe Leu Ala Tyr Ile Ala Gly Met Asp Thr Phe Ala Lys Gly Leu Leu
355 360 365

```
Ile Ala His Lys Leu Leu Glu Asp Glu Val Phe Glu Asn Phe Thr Lys
            370                 375                 380

Glu Arg Tyr Ala Ser Phe Ser Glu Gly Ile Gly Lys Asp Ile Val Glu
385                 390                 395                 400

Gly Lys Val Gly Phe Lys Glu Leu Glu Ser Tyr Ala Leu Gln Met Pro
                405                 410                 415

Val Ile Lys Asn Lys Ser Gly Arg Gln Glu Met Leu Glu Ala Ile Leu
                420                 425                 430

Asn Arg Tyr Ile Tyr Glu Val Asp Thr Ile Ser Asn Lys
            435                 440                 445

<210> SEQ ID NO 16
<211> LENGTH: 436
<212> TYPE: PRT
<213> ORGANISM: Fusobacterium mortiferum

<400> SEQUENCE: 16

Met Glu Phe Phe Lys Gly Ile Asp Lys Val Lys Tyr Glu Gly Val Lys
1               5                   10                  15

Thr Asn Asn Leu Leu Ala Phe Ala His Tyr Asn Pro Glu Glu Val Ile
            20                  25                  30

Leu Gly Lys Lys Met Lys Asp His Leu Lys Phe Ala Met Ser Tyr Trp
        35                  40                  45

His Thr Leu Thr Gly Glu Gly Thr Asp Pro Phe Gly Asn Ala Thr Met
    50                  55                  60

Asp Arg Glu Trp Asn Glu Tyr Thr Pro Met Glu Lys Ala Lys Ala Arg
65                  70                  75                  80

Val Lys Ala Gly Phe Glu Phe Met Glu Lys Leu Gly Leu Glu Tyr Phe
                85                  90                  95

Cys Phe His Asp Lys Asp Ile Ala Pro Glu Ala Glu Thr Leu Glu Glu
            100                 105                 110

Tyr His Arg Asn Leu Asp Glu Ile Val Asp Leu Ile Glu Glu Glu Met
        115                 120                 125

Lys Arg Thr Gly Ile Lys Leu Leu Trp Gly Thr Ser Asn Met Phe Ser
130                 135                 140

His Pro Arg Phe Met His Gly Ala Ala Thr Ser Cys Asn Ala Asp Val
145                 150                 155                 160

Phe Ala Tyr Ala Ala Ala Gln Thr Lys Lys Ala Leu Glu Ile Thr Lys
                165                 170                 175

Arg Leu Asn Gly Thr Gly Tyr Val Phe Trp Gly Gly Arg Glu Gly Tyr
            180                 185                 190

Glu Thr Leu Leu Asn Thr Asp Ile Gly Leu Glu Leu Asp Asn Leu Ala
        195                 200                 205

Arg Phe Leu Gln Met Ala Val Asp Tyr Ala Lys Lys Ile Gly Phe Glu
210                 215                 220

Gly Gln Phe Phe Ile Glu Pro Lys Pro Lys Glu Pro Thr Lys His Gln
225                 230                 235                 240

Tyr Asp Phe Asp Thr Thr Thr Val Leu Glu Phe Leu Arg Lys Tyr Asn
                245                 250                 255

Leu Asp Lys Tyr Phe Lys Met Asn Ile Glu Ala Asn His Ala Thr Leu
            260                 265                 270

Ala Gly His Thr Phe Gln His Glu Leu Cys Thr Ala Arg Ile Asn Gly
        275                 280                 285

Val Phe Gly Ser Ile Asp Ala Asn Gln Gly Asp Met Leu Leu Gly Trp
290                 295                 300
```

```
Asp Thr Asp Gln Phe Pro Thr Asn Val Tyr Asp Ala Val Leu Ala Met
305                 310                 315                 320

Tyr Glu Thr Leu Leu Ala Gly Gly Phe Lys Glu Gly Gly Leu Asn Phe
                325                 330                 335

Asp Ala Lys Val Arg Arg Gly Ser Phe Glu Pro Lys Asp Leu Phe Tyr
            340                 345                 350

Ala Tyr Ile Ser Gly Met Asp Thr Phe Ala Lys Gly Leu Lys Val Ala
        355                 360                 365

Ala Lys Leu Ile Glu Asp Gly Thr Phe Glu Lys Ile Lys Val Glu Arg
    370                 375                 380

Tyr Ser Ser Tyr Thr Thr Gly Ile Gly Lys Gln Ile Val Asn Gly Glu
385                 390                 395                 400

Val Gly Phe Glu Glu Leu Ser Lys Tyr Ala Leu Thr Asn Gly Val Lys
                405                 410                 415

Lys Asn Ser Ser Gly Arg Gln Glu Met Leu Glu Asn Ile Leu Asn Arg
            420                 425                 430

Tyr Ile Tyr Glu
            435

<210> SEQ ID NO 17
<211> LENGTH: 438
<212> TYPE: PRT
<213> ORGANISM: Bacteroides thetaiotaomicron

<400> SEQUENCE: 17

Met Ala Thr Lys Glu Phe Phe Pro Gly Ile Glu Lys Ile Lys Phe Glu
1               5                   10                  15

Gly Lys Asp Ser Lys Asn Pro Met Ala Phe Arg Tyr Tyr Asp Ala Glu
                20                  25                  30

Lys Val Ile Asn Gly Lys Lys Met Lys Asp Trp Leu Arg Phe Ala Met
            35                  40                  45

Ala Trp Trp His Thr Leu Cys Ala Glu Gly Gly Asp Gln Phe Gly Gly
        50                  55                  60

Gly Thr Lys Gln Phe Pro Trp Asn Gly Asn Ala Asp Ala Ile Gln Ala
65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Val Asp Leu Val Ser Glu Gly Ala
            100                 105                 110

Ser Val Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Glu Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
```

```
            225                 230                 235                 240
        Thr Lys His Gln Tyr Asp Val Asp Thr Glu Thr Val Ile Gly Phe Leu
                        245                 250                 255
        Lys Ala His Gly Leu Asp Lys Asp Phe Lys Val Asn Ile Glu Val Asn
                        260                 265                 270
        His Ala Thr Leu Ala Gly His Thr Phe Glu His Glu Leu Ala Val Ala
                        275                 280                 285
        Val Asp Asn Gly Met Leu Gly Ser Ile Asp Ala Asn Arg Gly Asp Tyr
                        290                 295                 300
        Gln Asn Gly Trp Asp Thr Asp Gln Phe Pro Ile Asp Asn Tyr Glu Leu
        305                 310                 315                 320
        Thr Gln Ala Met Met Gln Ile Ile Arg Asn Gly Gly Leu Gly Thr Gly
                        325                 330                 335
        Gly Thr Asn Phe Asp Ala Lys Thr Arg Arg Asn Ser Thr Asp Leu Glu
                        340                 345                 350
        Asp Ile Phe Ile Ala His Ile Ala Gly Met Asp Ala Met Ala Arg Ala
                        355                 360                 365
        Leu Glu Ser Ala Ala Ala Leu Leu Asp Glu Ser Pro Tyr Lys Lys Met
                        370                 375                 380
        Leu Ala Asp Arg Tyr Ala Ser Phe Asp Gly Gly Lys Gly Lys Glu Phe
        385                 390                 395                 400
        Glu Asp Gly Lys Leu Thr Leu Glu Asp Val Val Ala Tyr Ala Lys Thr
                        405                 410                 415
        Lys Gly Glu Pro Lys Gln Thr Ser Gly Lys Gln Glu Leu Tyr Glu Ala
                        420                 425                 430
        Ile Leu Asn Met Tyr Cys
                        435

<210> SEQ ID NO 18
<211> LENGTH: 437
<212> TYPE: PRT
<213> ORGANISM: Cyllamyces aberensis

<400> SEQUENCE: 18

Met Val Lys Glu Tyr Phe Pro Ala Ile Gln Ile Lys Phe Glu Gly
        1               5                   10                  15
        Lys Asp Ser Lys Asn Pro Met Ala Phe His Tyr Tyr Asp Ala Glu Lys
                        20                  25                  30
        Glu Ile Met Gly Lys Lys Met Lys Asp Trp Leu Arg Phe Ala Met Ala
                        35                  40                  45
        Trp Trp His Thr Leu Cys Ala Glu Gly Ser Asp Gln Phe Gly Pro Gly
                        50                  55                  60
        Thr Lys Thr Phe Pro Trp Asn Glu Gly Thr Asp Pro Ile Glu Lys Ala
        65                  70                  75                  80
        Lys Gln Lys Val Asp Ala Gly Phe Glu Ile Met Thr Lys Leu Gly Ile
                        85                  90                  95
        Glu His Tyr Cys Phe His Asp Val Asp Leu Val Asp Glu Gly Lys Asn
                        100                 105                 110
        Val Glu Glu Tyr Glu Lys Asn Leu Lys Thr Ile Val Ala Tyr Leu Lys
                        115                 120                 125
        Glu Lys Gln Lys Glu Thr Gly Ile Lys Leu Leu Trp Ser Thr Ala Asn
                        130                 135                 140
        Val Phe Gly His Lys Arg Tyr Met Asn Gly Ala Ser Thr Asn Pro Asp
        145                 150                 155                 160
```

```
Phe Asp Val Val Ala Arg Ala Ile Val Gln Ile Lys Asn Ala Met Asp
                165                 170                 175
Ala Gly Ile Glu Leu Gly Ala Glu Asn Tyr Val Phe Trp Gly Gly Arg
            180                 185                 190
Glu Gly Tyr Met Ser Leu Leu Asn Thr Asp Gln Lys Arg Glu Lys Glu
        195                 200                 205
His Met Ala Met Met Leu Gly Leu Ala Arg Asp Tyr Ala Arg Ser Lys
    210                 215                 220
Gly Phe Lys Gly Thr Phe Leu Ile Glu Pro Lys Pro Met Glu Pro Thr
225                 230                 235                 240
Lys His Gln Tyr Asp Val Asp Thr Glu Thr Val Ile Gly Phe Leu Arg
                245                 250                 255
Ala His Gly Leu Asp Lys Asp Phe Lys Ile Asn Ile Glu Val Asn His
            260                 265                 270
Ala Thr Leu Ala Gly His Thr Phe Glu His Glu Leu Ala Cys Ala Val
        275                 280                 285
Asp Ala Gly Met Leu Gly Ser Ile Asp Ala Asn Arg Gly Asp Tyr Gln
    290                 295                 300
Asn Gly Trp Asp Thr Asp Gln Phe Pro Ile Asp Gln Tyr Glu Leu Val
305                 310                 315                 320
Gln Ala Trp Met Glu Ile Ile Arg Gly Gly Phe Thr Thr Gly Gly
                325                 330                 335
Thr Asn Phe Asp Ala Lys Thr Arg Arg Asn Ser Thr Asp Leu Glu Asp
            340                 345                 350
Ile Ile Ile Ala His Ile Ser Gly Met Asp Ala Met Ala Arg Ala Leu
        355                 360                 365
Glu Asn Ala Ala Lys Leu Leu Thr Glu Ser Pro Tyr Lys Lys Met Lys
    370                 375                 380
Ala Asp Arg Tyr Ala Ser Phe Asp Ser Gly Met Gly Lys Asp Phe Glu
385                 390                 395                 400
Asp Gly Lys Leu Thr Phe Glu Gln Val Tyr Tyr Gly Lys Lys Val
                405                 410                 415
Asn Glu Pro Lys Gln Thr Ser Gly Lys Gln Glu Leu Tyr Glu Ala Ile
            420                 425                 430
Val Ala Met Tyr Met
        435

<210> SEQ ID NO 19
<211> LENGTH: 439
<212> TYPE: PRT
<213> ORGANISM: Bacteroides fragilis

<400> SEQUENCE: 19

Met Ala Thr Lys Glu Tyr Phe Pro Gly Ile Gly Lys Ile Lys Phe Glu
1               5                   10                  15
Gly Lys Asp Ser Lys Asn Pro Met Ala Phe Arg Tyr Tyr Asp Ala Glu
            20                  25                  30
Lys Met Ile Asn Gly Arg Ser Met Lys Asp Trp Leu Lys Phe Ala Met
        35                  40                  45
Ala Trp Trp His Thr Leu Cys Ala Glu Gly Gly Asp Gln Phe Gly Gly
    50                  55                  60
Gly Thr Lys Gln Phe Pro Trp Asn Gly Asp Pro Asp Pro Val Gln Ala
65                  70                  75                  80
Ala Lys Asn Lys Met Asp Ala Gly Phe Glu Phe Met Gln Lys Met Gly
                85                  90                  95
```

```
Ile Gly Tyr Tyr Cys Phe His Asp Val Asp Leu Val Thr Glu Ala Asp
            100                 105                 110

Ser Ile Glu Ala Tyr Glu Ala Asn Leu Lys Glu Leu Val Ala Tyr Ala
        115                 120                 125

Lys Gln Lys Gln Ala Glu Thr Gly Ile Lys Leu Leu Trp Gly Thr Ala
    130                 135                 140

Asn Val Phe Ser His Ala Arg Tyr Met Asn Gly Ala Ala Thr Asn Pro
145                 150                 155                 160

Asp Phe Asp Val Val Ala Arg Ala Val Gln Ile Lys Asn Ala Ile
                165                 170                 175

Asp Ala Thr Ile Glu Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
                195                 200                 205

Glu His Leu Ala Gln Met Leu Thr Ile Ala Arg Asp Tyr Gly Arg Ala
        210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asn Gln Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Asp Gly Leu Gly Asn Gly
                325                 330                 335

Gly Thr Asn Phe Asp Ala Lys Thr Arg Arg Asn Ser Thr Asp Pro Glu
            340                 345                 350

Asp Ile Phe Ile Ala His Ile Ala Gly Met Asp Ala Met Ala Arg Ala
        355                 360                 365

Leu Glu Ser Ala Ala Asn Leu Leu Asn Glu Ser Pro Tyr Gln Lys Met
    370                 375                 380

Leu Ser Asp Arg Tyr Ala Ser Phe Asp Ala Gly Lys Gly Lys Glu Phe
385                 390                 395                 400

Glu Glu Gly Lys Leu Ser Leu Glu Glu Leu Val Ala Tyr Ala Lys Ala
                405                 410                 415

Asn Gly Glu Pro Lys Gln Thr Ser Gly Gln Gln Glu Leu Tyr Glu Ala
            420                 425                 430

Leu Val Asn Ile Tyr Ser Leu
        435

<210> SEQ ID NO 20
<211> LENGTH: 437
<212> TYPE: PRT
<213> ORGANISM: Orpinomyces sp.ukk1

<400> SEQUENCE: 20

Met Thr Lys Glu Tyr Phe Pro Thr Ile Gly Lys Ile Arg Phe Glu Gly
1               5                   10                  15

Lys Asp Ser Lys Asn Pro Met Ala Phe His Tyr Tyr Asp Ala Glu Lys
```

```
                  20                  25                  30
        Glu Val Met Gly Lys Lys Met Lys Asp Trp Leu Arg Phe Ala Met Ala
                        35                  40                  45
        Trp Trp His Thr Leu Cys Ala Asp Gly Ala Asp Gln Phe Gly Val Gly
                        50                  55                  60
        Thr Lys Ser Phe Pro Trp Asn Glu Gly Thr Asp Pro Ile Ala Ile Ala
        65                  70                  75                  80
        Lys Gln Lys Val Asp Ala Gly Phe Glu Ile Met Thr Lys Leu Gly Ile
                            85                  90                  95
        Glu His Tyr Cys Phe His Asp Val Asp Leu Val Ser Glu Gly Asn Ser
                        100                 105                 110
        Ile Glu Glu Tyr Glu Ser Asn Leu Lys Gln Val Val Ala Tyr Leu Lys
                        115                 120                 125
        Gln Lys Gln Gln Glu Thr Gly Ile Lys Leu Leu Trp Ser Thr Ala Asn
                        130                 135                 140
        Val Phe Gly Asn Pro Arg Tyr Met Asn Gly Ala Ser Thr Asn Pro Asp
        145                 150                 155                 160
        Phe Asp Val Val Ala Arg Ala Ile Val Gln Ile Lys Asn Ala Met Asp
                            165                 170                 175
        Ala Gly Ile Glu Leu Gly Ala Glu Asn Tyr Val Phe Trp Gly Gly Arg
                        180                 185                 190
        Glu Gly Tyr Met Ser Leu Leu Asn Thr Asp Gln Lys Arg Glu Lys Glu
                        195                 200                 205
        His Met Ala Thr Met Leu Thr Met Ala Arg Asp Tyr Ala Arg Ser Lys
                        210                 215                 220
        Gly Phe Lys Gly Thr Phe Leu Ile Glu Pro Lys Pro Met Glu Pro Thr
        225                 230                 235                 240
        Lys His Gln Tyr Asp Val Asp Thr Glu Thr Val Ile Gly Phe Leu Arg
                            245                 250                 255
        Ala His Asn Leu Asp Lys Asp Phe Lys Val Asn Ile Glu Val Asn His
                        260                 265                 270
        Ala Thr Leu Ala Gly His Thr Phe Glu His Glu Leu Ala Cys Ala Val
                        275                 280                 285
        Asp Ala Gly Met Leu Gly Ser Ile Asp Ala Asn Arg Gly Asp Tyr Gln
                        290                 295                 300
        Asn Gly Trp Asp Thr Asp Gln Phe Pro Ile Asp Gln Tyr Glu Leu Val
        305                 310                 315                 320
        Gln Ala Trp Met Glu Ile Ile Arg Gly Gly Phe Val Thr Gly Gly
                            325                 330                 335
        Thr Asn Phe Asp Ala Lys Thr Arg Arg Asn Ser Thr Asp Leu Glu Asp
                        340                 345                 350
        Ile Ile Ile Ala His Ile Ser Gly Met Asp Ala Met Ala Arg Ala Leu
                        355                 360                 365
        Glu Asn Ala Ala Lys Leu Leu Gln Glu Ser Pro Tyr Cys Asn Met Lys
                        370                 375                 380
        Lys Glu Arg Tyr Ala Ser Phe Asp Ser Gly Ile Gly Lys Asp Phe Glu
        385                 390                 395                 400
        Asp Gly Lys Leu Thr Leu Glu Gln Val Tyr Glu Tyr Gly Lys Lys Asn
                            405                 410                 415
        Gly Glu Pro Lys Val Thr Ser Gly Lys Gln Glu Leu Tyr Glu Ala Ile
                        420                 425                 430
        Val Ala Met Tyr Gln
                        435
```

<210> SEQ ID NO 21
<211> LENGTH: 437
<212> TYPE: PRT
<213> ORGANISM: Piromyces sp.E2

<400> SEQUENCE: 21

Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys

```
                 370                 375                 380
Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
                420                 425                 430

Val Ala Met Tyr Gln
            435

<210> SEQ ID NO 22
<211> LENGTH: 439
<212> TYPE: PRT
<213> ORGANISM: Lactococcus lactis

<400> SEQUENCE: 22

Met Ala Tyr Phe Asn Asp Ile Ala Pro Ile Lys Tyr Glu Gly Thr Lys
1               5                   10                  15

Thr Lys Asn Met Phe Ala Phe Arg His Tyr Asn Pro Glu Glu Val Val
                20                  25                  30

Ala Gly Lys Thr Met Glu Glu Gln Leu His Phe Ala Leu Ala Phe Trp
            35                  40                  45

His Thr Ile Thr Met Asp Gly Ser Asp Pro Phe Gly Gly Ala Thr Met
        50                  55                  60

Glu Arg Pro Trp Asp Leu Glu Gly Gly Ser Glu Leu Asp Arg Ala His
65                  70                  75                  80

Arg Arg Val Asp Ala Phe Phe Glu Ile Ala Glu Lys Leu Gly Val Lys
                85                  90                  95

Tyr Tyr Cys Phe His Asp Ile Asp Ile Ala Pro Thr Gly Asn Ser Leu
            100                 105                 110

Lys Glu Phe Tyr Ala Asn Leu Asp Glu Ile Thr Asp His Leu Leu Glu
        115                 120                 125

Lys Gln Lys Ala Thr Gly Ile Lys Leu Leu Trp Asn Thr Ala Asn Met
130                 135                 140

Phe Ser Asn Pro Arg Tyr Met Asn Gly Val Ser Thr Ser Asn Arg Ala
145                 150                 155                 160

Glu Val Phe Ala Tyr Gly Ala Ala Gln Val Lys Lys Gly Leu Glu Leu
                165                 170                 175

Ser Lys Lys Leu Gly Gly Glu Asn Tyr Val Phe Trp Gly Gly Arg Glu
            180                 185                 190

Gly Tyr Glu Ser Leu Leu Asn Thr Asp Met Gly Leu Glu Met Asp His
        195                 200                 205

Met Ala Lys Phe Phe His Leu Ala Ile Asp Tyr Ala Lys Ser Ile Asn
210                 215                 220

His Leu Pro Ile Phe Leu Ile Glu Pro Lys Pro Lys Glu Pro Met Thr
225                 230                 235                 240

His Gln Tyr Asp Phe Asp Ser Ala Thr Ala Leu Ala Phe Leu Gln Lys
                245                 250                 255

Tyr Asp Leu Asp Lys Tyr Phe Lys Leu Asn Leu Glu Thr Asn His Ala
            260                 265                 270

Trp Leu Ala Gly His Thr Phe Glu His Glu Leu Asn Thr Ala Arg Thr
        275                 280                 285

Phe Asn Ala Leu Gly Ser Ile Asp Ala Asn Gln Gly Asn Tyr Leu Leu
    290                 295                 300
```

```
Gly Trp Asp Thr Asp Glu Phe Pro Thr Leu Val Ile Asp Ile Thr Leu
305                 310                 315                 320

Ala Met His Gln Ile Leu Leu Asn Gly Leu Gly Lys Gly Gly Ile
                325                 330                 335

Asn Phe Asp Ala Lys Val Arg Arg Thr Ser Phe Lys Ala Glu Asp Leu
            340                 345                 350

Ile Leu Ala His Ile Ala Gly Met Asp Thr Tyr Ala Arg Ala Leu Lys
                355                 360                 365

Gly Ala Ala Ile Ile Glu Asp Lys Phe Leu Ser Asp Ile Val Asp
370                 375                 380

Glu Arg Tyr Ser Ser Tyr Lys Asn Thr Glu Val Gly Gln Ser Ile Glu
385                 390                 395                 400

Asn Gly Thr Ala Thr Phe Glu Ser Leu Ala Ala Phe Ala Leu Glu Tyr
                405                 410                 415

Gly Asp Asp Ile Glu Leu Asp Ser Asn His Leu Glu Tyr Ile Lys Ser
                420                 425                 430

Val Leu Asn Asp Tyr Leu Val
                435

<210> SEQ ID NO 23
<211> LENGTH: 456
<212> TYPE: PRT
<213> ORGANISM: Ciona intestinals

<400> SEQUENCE: 23

Met Ser Ser Phe Ala Pro Ala Ser Gly Lys Ser Asp Leu Ala Glu Ala
1               5                   10                  15

Gly Ser Leu Leu Thr Lys Tyr Pro Leu Glu Val Lys Lys Ile Pro Tyr
                20                  25                  30

Lys Pro Asp Ala Lys Val Asp Asp Val Leu Cys Phe Arg His Tyr Asn
            35                  40                  45

Glu Ser Glu Val Val Met Gly Lys Pro Met Ser Asp Trp Leu Arg Phe
50                  55                  60

Ser Val Cys Tyr Trp His Thr Phe Arg Gly Thr Gly Ala Asp Pro Phe
65                  70                  75                  80

Gly Phe Pro Thr Leu Val Arg Pro Trp Asp Asp Gly Thr Asp Ser Ile
                85                  90                  95

Glu Asn Ala Glu Arg Arg Met Arg Val Ala Phe Asp Phe Met Ser Lys
            100                 105                 110

Leu Gly Val Lys Tyr Trp Thr Phe His Asp Arg Asp Ile Ala Pro Glu
        115                 120                 125

Gly Val Thr Leu Ser Glu Thr Asn Ala Asn Leu Asp Arg Leu Ala Glu
    130                 135                 140

Leu Ala Ser Gln Leu Gln Gly Glu Thr Gly Ile Lys Leu Leu Trp Asn
145                 150                 155                 160

Thr Cys Asn Leu Phe Ala His Pro Arg Tyr Ser Asn Gly Ala Ala Thr
                165                 170                 175

Asn Ala Asp Ala His Val Val Ala Tyr Ala Ala Ala Gln Val Lys Lys
            180                 185                 190

Ser Leu Glu Ile Gly Lys Lys Leu Gly Ala Glu Asn Phe Val Phe Trp
        195                 200                 205

Gly Gly Arg Glu Gly Tyr His Thr Leu Leu Asn Thr Asn Val Arg Glu
    210                 215                 220

Glu Leu Asp Asn Leu Ala Asn Phe Phe Lys Met Val Val Ala Tyr Lys
225                 230                 235                 240
```

```
Lys Lys Ile Gly Phe Thr Gly Gln Phe Leu Ile Glu Pro Lys Pro Lys
                245                 250                 255

Glu Pro Ser Lys His Gln Tyr Asp Tyr Asp Ala Met Thr Val Ile Ala
            260                 265                 270

Phe Leu Lys Thr Tyr Asp Leu Asp Lys Asp Phe Lys Leu Asn Ile Glu
        275                 280                 285

Pro Asn His Thr Thr Leu Ala Gly His Cys His Glu His Asp Val Val
    290                 295                 300

Met Ala Ser Ala Tyr Asn Met Leu Gly Ser Val Asp Ser Asn Thr Gly
305                 310                 315                 320

Ser Pro Asp Leu Gly Trp Asp Thr Asp Gln Phe Pro Met Asp Val Lys
                325                 330                 335

Asn Ala Thr Met Ile Met Gln Thr Val Leu Glu Gln Gly Gly Leu Ala
            340                 345                 350

Pro Gly Gly Leu Asn Phe Asp Cys Lys Val Arg Arg Glu Ser Thr Asp
        355                 360                 365

Val Ile Asp Met Met Ile Ala His Val Gly Ala Met Asp Cys Phe Ala
    370                 375                 380

Lys Ala Leu Lys Ile Ala Ala Lys Ile Arg Glu Asp Gly Val Leu Gly
385                 390                 395                 400

Lys Met Lys Lys Glu Arg Tyr Ala Ser Phe Gly Ser Gly Leu Gly Leu
                405                 410                 415

Lys Ile Lys Thr Gly Thr Ala Thr Leu Glu Glu Cys Asp Ser Phe Ile
            420                 425                 430

Gln Glu Asn Gly Glu Pro Ala Lys Leu Ser Gly Lys Gln Glu Met Phe
        435                 440                 445

Glu Ala Val Leu Asn Arg Tyr Phe
    450                 455

<210> SEQ ID NO 24
<211> LENGTH: 18
<212> TYPE: PRT
<213> ORGANISM: Reticulitermis speratus

<400> SEQUENCE: 24

Phe Glu Phe Met Ser Lys Leu Gly Val Glu Tyr Phe Cys Phe His Asp
1               5                   10                  15

Ala Asp

<210> SEQ ID NO 25
<211> LENGTH: 20
<212> TYPE: PRT
<213> ORGANISM: Reticulitermis speratus

<400> SEQUENCE: 25

Gly Gly Val Gly Tyr Val Phe Trp Gly Gly Arg Glu Gly Tyr Glu Thr
1               5                   10                  15

Leu Leu Asn Thr
            20

<210> SEQ ID NO 26
<211> LENGTH: 23
<212> TYPE: PRT
<213> ORGANISM: Reticulitermis speratus

<400> SEQUENCE: 26

Gly Phe Lys Gly Asp Phe Tyr Ile Glu Pro Lys Pro Lys Glu Pro Thr
```

```
<210> SEQ ID NO 27
<211> LENGTH: 34
<212> TYPE: PRT
<213> ORGANISM: Reticulitermis speratus

<400> SEQUENCE: 27

Gly Gly Leu Asn Phe Asp Ser Lys Val Arg Arg Leu Glu Lys Asp Phe
1               5                   10                  15

Lys Leu Asn Ile Glu Ala Asn His Ala Thr Leu Ala Gly His Thr Phe
            20                  25                  30

Gln His

<210> SEQ ID NO 28
<211> LENGTH: 21
<212> TYPE: PRT
<213> ORGANISM: Reticulitermis speratus

<400> SEQUENCE: 28

Leu Gly Ser Val Asp Ala Asn Thr Gly Asp Pro Leu Leu Gly Trp Asp
1               5                   10                  15

Thr Asp Glu Phe Pro
            20

<210> SEQ ID NO 29
<211> LENGTH: 11
<212> TYPE: PRT
<213> ORGANISM: Reticulitermis speratus

<400> SEQUENCE: 29

Gly Gly Leu Asn Phe Asp Ser Lys Val Arg Arg
1               5                   10

<210> SEQ ID NO 30
<211> LENGTH: 456
<212> TYPE: PRT
<213> ORGANISM: Artificial
<220> FEATURE:
<223> OTHER INFORMATION: Xylose isomerase mutant

<400> SEQUENCE: 30

Met Ser Ser Phe Ala Pro Ala Ser Gly Lys Ser Asp Leu Ala Glu Ala
1               5                   10                  15

Gly Ser Leu Leu Thr Lys Tyr Pro Leu Glu Val Lys Lys Ile Pro Tyr
            20                  25                  30

Lys Pro Asp Ala Lys Val Asp Asp Val Leu Cys Phe His Tyr Asn
        35                  40                  45

Glu Ser Glu Val Val Met Gly Lys Pro Met Ser Asp Trp Leu Arg Phe
    50                  55                  60

Ser Val Cys Tyr Trp His Thr Phe Arg Gly Thr Gly Ala Asp Pro Phe
65                  70                  75                  80

Gly Phe Pro Thr Leu Val Arg Trp Asp Asp Gly Thr Asp Ser Ile
                85                  90                  95

Glu Asn Ala Glu Arg Arg Met Arg Val Ala Phe Asp Phe Met Ser Lys
            100                 105                 110

Leu Gly Val Lys Tyr Trp Thr Phe His Asp Arg Asp Ile Ala Pro Glu
        115                 120                 125
```

Gly Val Thr Leu Ser Glu Thr Asn Ala Asn Leu Asp Arg Leu Ala Glu
                130                 135                 140

Leu Ala Ser Gln Leu Gln Gly Glu Thr Gly Ile Lys Leu Leu Trp Asn
145                 150                 155                 160

Thr Cys Asn Leu Phe Ala His Pro Arg Tyr Ser Asn Gly Ala Ala Thr
                165                 170                 175

Asn Ala Asp Ala His Val Val Ala Tyr Ala Ala Gln Val Lys Lys
                180                 185                 190

Ser Leu Glu Ile Gly Lys Lys Leu Gly Ala Glu Asn Phe Val Phe Trp
                195                 200                 205

Gly Gly Arg Glu Gly Tyr His Thr Leu Leu Asn Thr Asn Val Arg Glu
                210                 215                 220

Glu Leu Asp Asn Leu Ala Asn Phe Phe Lys Met Val Val Ala Tyr Lys
225                 230                 235                 240

Lys Lys Ile Gly Phe Thr Gly Gln Phe Leu Ile Glu Pro Lys Pro Lys
                245                 250                 255

Glu Pro Ser Lys His Gln Tyr Asp Tyr Asp Ala Met Thr Val Ile Ala
                260                 265                 270

Phe Leu Lys Thr Tyr Asp Leu Asp Lys Asp Phe Lys Leu Asn Ile Glu
                275                 280                 285

Pro Asn His Thr Thr Leu Ala Gly His Cys His Glu His Asp Val Val
                290                 295                 300

Met Ala Ser Ala Tyr Asn Met Leu Gly Ser Val Asp Ser Asn Thr Gly
305                 310                 315                 320

Ser Pro Asp Leu Gly Trp Asp Thr Asp Gln Phe Pro Met Asp Val Lys
                325                 330                 335

Thr Ala Thr Met Ile Met Gln Thr Val Leu Glu Gln Gly Gly Leu Ala
                340                 345                 350

Pro Gly Gly Leu Asn Phe Asp Cys Lys Val Arg Arg Glu Ser Thr Asp
                355                 360                 365

Val Ile Asp Met Met Ile Ala His Val Gly Ala Met Asp Cys Phe Ala
                370                 375                 380

Lys Ala Leu Lys Ile Ala Ala Lys Ile Arg Glu Asp Gly Val Leu Gly
385                 390                 395                 400

Lys Met Lys Lys Glu Arg Tyr Ala Ser Phe Gly Ser Gly Leu Gly Leu
                405                 410                 415

Lys Ile Lys Thr Gly Thr Ala Thr Leu Glu Glu Cys Asp Ser Phe Ile
                420                 425                 430

Gln Glu Asn Gly Glu Pro Ala Lys Leu Ser Gly Lys Gln Glu Met Phe
                435                 440                 445

Glu Ala Val Leu Asn Arg Tyr Phe
    450                 455

<210> SEQ ID NO 31
<211> LENGTH: 438
<212> TYPE: PRT
<213> ORGANISM: Artificial
<220> FEATURE:
<223> OTHER INFORMATION: Xylose isomerase mutant

<400> SEQUENCE: 31

Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
                20                  25                  30

-continued

```
Val Ala Gly Lys Thr Met Lys Glu His Cys Arg Phe Ala Leu Ser Trp
         35                  40                  45
Trp His Thr Leu Cys Ala Gly Gly Ala Asp Pro Phe Gly Val Thr Thr
 50                  55                  60
Met Asp Arg Thr Tyr Gly Asn Ile Thr Asp Pro Met Glu Leu Ala Lys
 65                  70                  75                  80
Ala Lys Val Asp Ala Gly Phe Glu Leu Met Thr Lys Leu Gly Ile Glu
                 85                  90                  95
Phe Phe Cys Phe His Asp Ala Asp Ile Ala Pro Glu Gly Asp Thr Phe
                100                 105                 110
Glu Glu Ser Lys Lys Asn Leu Phe Glu Ile Val Asp Tyr Ile Lys Glu
                115                 120                 125
Lys Met Asp Gln Thr Gly Ile Lys Leu Leu Trp Gly Thr Ala Asn Asn
130                 135                 140
Phe Ser His Pro Arg Phe Met His Gly Ala Ser Thr Ser Cys Asn Ala
145                 150                 155                 160
Asp Val Phe Ala Tyr Ala Ala Ala Lys Ile Lys Asn Ala Leu Asp Ala
                165                 170                 175
Thr Ile Lys Leu Gly Gly Lys Gly Tyr Val Phe Trp Gly Gly Arg Glu
                180                 185                 190
Gly Tyr Glu Thr Leu Leu Asn Thr Asp Leu Gly Leu Glu Leu Asp Asn
                195                 200                 205
Met Ala Arg Leu Met Lys Met Ala Val Glu Tyr Gly Arg Ala Asn Gly
210                 215                 220
Phe Asp Gly Asp Phe Tyr Ile Glu Pro Lys Pro Lys Glu Pro Thr Lys
225                 230                 235                 240
His Gln Tyr Asp Phe Asp Thr Ala Thr Val Leu Ala Phe Leu Arg Lys
                245                 250                 255
Tyr Gly Leu Glu Lys Asp Phe Lys Met Asn Ile Glu Ala Asn His Ala
                260                 265                 270
Thr Leu Ala Gly His Thr Phe Glu His Glu Leu Ala Met Ala Arg Val
                275                 280                 285
Asn Gly Ala Phe Gly Ser Val Asp Ala Asn Gln Gly Asp Pro Asn Leu
                290                 295                 300
Gly Trp Asp Thr Asp Gln Phe Pro Thr Asp Val His Ser Ala Thr Leu
305                 310                 315                 320
Ala Met Leu Glu Val Leu Lys Ala Gly Gly Phe Thr Asn Gly Gly Leu
                325                 330                 335
Thr Phe Asp Ala Lys Val Arg Arg Gly Ser Phe Glu Phe Asp Asp Ile
                340                 345                 350
Ala Tyr Gly Tyr Ile Ala Gly Met Asp Thr Phe Ala Leu Gly Leu Ile
                355                 360                 365
Lys Ala Ala Glu Ile Ile Asp Asp Gly Arg Ile Ala Lys Phe Val Asp
                370                 375                 380
Asp Arg Tyr Ala Ser Tyr Lys Thr Gly Ile Gly Lys Ala Ile Val Asp
385                 390                 395                 400
Gly Thr Thr Ser Leu Glu Glu Leu Glu Gln Tyr Val Leu Thr His Ser
                405                 410                 415
Glu Pro Val Met Gln Ser Gly Arg Gln Glu Val Leu Glu Thr Ile Val
                420                 425                 430
Asn Asn Ile Leu Phe Arg
                435
```

<210> SEQ ID NO 32
<211> LENGTH: 445
<212> TYPE: PRT
<213> ORGANISM: Artificial
<220> FEATURE:
<223> OTHER INFORMATION: Xylose isomerase mutant

<400> SEQUENCE: 32

```
Met Ser Glu Ile Phe Lys Gly Ile Gly Gln Ile Lys Phe Glu Gly Val
1               5                   10                  15
Lys Ser Asp Asn Glu Leu Ala Phe Arg Tyr Tyr Asn Pro Glu Gln Val
                20                  25                  30
Val Gly Asn Lys Thr Met Lys Glu His Leu Arg Phe Ala Met Ser Tyr
            35                  40                  45
Trp His Thr Leu Cys Gly Glu Gly Asn Asp Pro Phe Gly Val Gly Thr
50                  55                  60
Val Glu Arg Pro Trp Asn Asn Val Thr Asp Pro Ile Glu Ile Ala Lys
65                  70                  75                  80
Ile Lys Val Asp Ala Gly Phe Glu Phe Met Ser Lys Met Gly Ile Glu
                85                  90                  95
Tyr Phe Cys Phe His Asp Arg Asp Ile Ala Pro Glu Gly Arg Asp Leu
            100                 105                 110
Glu Glu Thr Asn Lys Ile Leu Asp Glu Ile Val Glu Tyr Ile Lys Val
        115                 120                 125
Asn Met Glu Lys Thr Gly Ile Lys Leu Leu Trp Gly Thr Ala Asn Met
130                 135                 140
Phe Gly Asn Pro Arg Phe Val His Gly Ala Ser Thr Thr Cys Asn Ala
145                 150                 155                 160
Asp Val Tyr Ala Tyr Ala Ala Ala Gln Val Lys Lys Ala Met Glu Ile
                165                 170                 175
Thr Lys Tyr Leu Gly Gly Glu Asn Phe Val Phe Trp Gly Gly Arg Glu
            180                 185                 190
Gly Tyr Glu Thr Leu Leu Asn Thr Asn Thr Glu Leu Glu Met Asp Asn
        195                 200                 205
Phe Ala Arg Phe Leu Gln Met Ala Val Asp Tyr Ala Lys Glu Ile Gly
210                 215                 220
Phe Thr Gly Gln Phe Leu Ile Glu Pro Lys Pro Lys Glu Pro Thr Lys
225                 230                 235                 240
His Gln Tyr Asp Phe Asp Thr Ala Thr Val Leu Gly Phe Leu Arg Lys
                245                 250                 255
Tyr Asn Leu Asp Lys Tyr Phe Lys Met Asn Ile Glu Ala Asn His Ala
            260                 265                 270
Thr Leu Ala Gly His Thr Phe Gln His Glu Leu Asn Ile Ala Arg Ile
        275                 280                 285
Asn Asn Val Leu Gly Ser Ile Asp Ala Asn Gln Gly Asp Leu Leu Leu
290                 295                 300
Gly Trp Asp Thr Asp Gln Phe Pro Thr Asn Ile Tyr Asp Ala Thr Leu
305                 310                 315                 320
Ala Met Tyr Glu Val Leu Lys Gln Gly Gly Ile Ala Pro Gly Gly Phe
                325                 330                 335
Thr Phe Asp Ser Lys Val Arg Arg Ala Ser Phe Glu Val Glu Asp Leu
            340                 345                 350
Phe Leu Ala Tyr Ile Ala Gly Met Asp Thr Phe Ala Lys Gly Leu Leu
        355                 360                 365
```

```
Ile Ala His Lys Leu Leu Glu Asp Glu Val Phe Glu Asn Phe Thr Lys
370                 375                 380

Glu Arg Tyr Ala Ser Phe Ser Glu Gly Ile Gly Lys Asp Ile Val Glu
385                 390                 395                 400

Gly Lys Val Gly Phe Lys Glu Leu Glu Ser Tyr Ala Leu Gln Met Pro
                405                 410                 415

Val Ile Lys Asn Lys Ser Gly Arg Gln Glu Met Leu Glu Ala Ile Leu
                420                 425                 430

Asn Arg Tyr Ile Tyr Glu Val Asp Thr Ile Ser Asn Lys
                435                 440                 445

<210> SEQ ID NO 33
<211> LENGTH: 436
<212> TYPE: PRT
<213> ORGANISM: Artificial
<220> FEATURE:
<223> OTHER INFORMATION: Xylose isomerase mutant

<400> SEQUENCE: 33

Met Glu Phe Phe Lys Gly Ile Asp Lys Val Lys Tyr Glu Gly Val Lys
1               5                   10                  15

Thr Asn Asn Leu Leu Ala Phe Ala His Tyr Asn Pro Glu Glu Val Ile
                20                  25                  30

Leu Gly Lys Lys Met Lys Asp His Leu Lys Phe Ala Met Ser Tyr Trp
            35                  40                  45

His Thr Leu Thr Gly Glu Gly Thr Asp Pro Phe Gly Asn Ala Thr Met
        50                  55                  60

Asp Arg Glu Trp Asn Glu Tyr Thr Pro Met Glu Lys Ala Lys Ala Arg
65                  70                  75                  80

Val Lys Ala Gly Phe Glu Phe Met Glu Lys Leu Gly Leu Glu Tyr Phe
                85                  90                  95

Cys Phe His Asp Lys Asp Ile Ala Pro Glu Ala Glu Thr Leu Glu Glu
                100                 105                 110

Tyr His Arg Asn Leu Asp Glu Ile Val Asp Leu Ile Glu Glu Glu Met
            115                 120                 125

Lys Arg Thr Gly Ile Lys Leu Leu Trp Gly Thr Ser Asn Met Phe Ser
130                 135                 140

His Pro Arg Phe Met His Gly Ala Ala Thr Ser Cys Asn Ala Asp Val
145                 150                 155                 160

Phe Ala Tyr Ala Ala Ala Gln Thr Lys Lys Ala Leu Glu Ile Thr Lys
                165                 170                 175

Arg Leu Asn Gly Thr Gly Tyr Val Phe Trp Gly Gly Arg Glu Gly Tyr
            180                 185                 190

Glu Thr Leu Leu Asn Thr Asp Ile Gly Leu Glu Leu Asp Asn Leu Ala
        195                 200                 205

Arg Phe Leu Gln Met Ala Val Asp Tyr Ala Lys Lys Ile Gly Phe Glu
210                 215                 220

Gly Gln Phe Phe Ile Glu Pro Lys Pro Lys Glu Pro Thr Lys His Gln
225                 230                 235                 240

Tyr Asp Phe Asp Thr Thr Thr Val Leu Glu Phe Leu Arg Lys Tyr Asn
                245                 250                 255

Leu Asp Lys Tyr Phe Lys Met Asn Ile Glu Ala Asn His Ala Thr Leu
            260                 265                 270

Ala Gly His Thr Phe Gln His Glu Leu Cys Thr Ala Arg Ile Asn Gly
        275                 280                 285
```

```
Val Phe Gly Ser Ile Asp Ala Asn Gln Gly Asp Met Leu Leu Gly Trp
            290                 295                 300

Asp Thr Asp Gln Phe Pro Thr Asn Val Tyr Asp Ala Val Leu Ala Met
305                 310                 315                 320

Tyr Glu Thr Leu Leu Ala Gly Gly Phe Lys Glu Gly Gly Leu Thr Phe
                325                 330                 335

Asp Ala Lys Val Arg Arg Gly Ser Phe Glu Pro Lys Asp Leu Phe Tyr
                340                 345                 350

Ala Tyr Ile Ser Gly Met Asp Thr Phe Ala Lys Gly Leu Lys Val Ala
                355                 360                 365

Ala Lys Leu Ile Glu Asp Gly Thr Phe Glu Lys Ile Lys Val Glu Arg
                370                 375                 380

Tyr Ser Ser Tyr Thr Thr Gly Ile Gly Lys Gln Ile Val Asn Gly Glu
385                 390                 395                 400

Val Gly Phe Glu Glu Leu Ser Lys Tyr Ala Leu Thr Asn Gly Val Lys
                405                 410                 415

Lys Asn Ser Ser Gly Arg Gln Glu Met Leu Glu Asn Ile Leu Asn Arg
                420                 425                 430

Tyr Ile Tyr Glu
            435

<210> SEQ ID NO 34
<211> LENGTH: 438
<212> TYPE: PRT
<213> ORGANISM: Artificial
<220> FEATURE:
<223> OTHER INFORMATION: Xylose isomerase mutant

<400> SEQUENCE: 34

Met Ala Thr Lys Glu Phe Phe Pro Gly Ile Glu Lys Ile Lys Phe Glu
1               5                   10                  15

Gly Lys Asp Ser Lys Asn Pro Met Ala Phe Arg Tyr Tyr Asp Ala Glu
                20                  25                  30

Lys Val Ile Asn Gly Lys Lys Met Lys Asp Trp Leu Arg Phe Ala Met
            35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asn Ala Asp Ala Ile Gln Ala
65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Val Asp Leu Val Ser Glu Gly Ala
            100                 105                 110

Ser Val Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Glu Asn Tyr Val Phe Trp Gly Gly
            180                 185                 190

Arg Glu Gly Tyr Met Ser Leu Leu Asn Thr Asp Gln Lys Arg Glu Lys
        195                 200                 205
```

-continued

Glu His Leu Ala Gln Met Leu Thr Ile Ala Arg Asp Tyr Ala Arg Ala
210             215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
                260                 265                 270

His Ala Thr Leu Ala Gly His Thr Phe Glu His Glu Leu Ala Val Ala
            275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Thr Gly
                325                 330                 335

Gly Thr Thr Phe Asp Ala Lys Thr Arg Arg Asn Ser Thr Asp Leu Glu
                340                 345                 350

Asp Ile Phe Ile Ala His Ile Ala Gly Met Asp Ala Met Ala Arg Ala
            355                 360                 365

Leu Glu Ser Ala Ala Ala Leu Leu Asp Glu Ser Pro Tyr Lys Lys Met
370                 375                 380

Leu Ala Asp Arg Tyr Ala Ser Phe Asp Gly Lys Gly Lys Glu Phe
385                 390                 395                 400

Glu Asp Gly Lys Leu Thr Leu Glu Asp Val Val Ala Tyr Ala Lys Thr
                405                 410                 415

Lys Gly Glu Pro Lys Gln Thr Ser Gly Lys Gln Glu Leu Tyr Glu Ala
                420                 425                 430

Ile Leu Asn Met Tyr Cys
            435

<210> SEQ ID NO 35
<211> LENGTH: 437
<212> TYPE: PRT
<213> ORGANISM: Artificial
<220> FEATURE:
<223> OTHER INFORMATION: Xylose isomerase mutant

<400> SEQUENCE: 35

Met Val Lys Glu Tyr Phe Pro Ala Ile Gln Lys Ile Lys Phe Glu Gly
1               5                   10                  15

Lys Asp Ser Lys Asn Pro Met Ala Phe His Tyr Tyr Asp Ala Glu Lys
                20                  25                  30

Glu Ile Met Gly Lys Lys Met Lys Asp Trp Leu Arg Phe Ala Met Ala
            35                  40                  45

Trp Trp His Thr Leu Cys Ala Glu Gly Ser Asp Gln Phe Gly Pro Gly
        50                  55                  60

Thr Lys Thr Phe Pro Trp Asn Glu Gly Thr Asp Pro Ile Glu Lys Ala
65                  70                  75                  80

Lys Gln Lys Val Asp Ala Gly Phe Glu Ile Met Thr Lys Leu Gly Ile
                85                  90                  95

Glu His Tyr Cys Phe His Asp Val Asp Leu Val Asp Glu Gly Lys Asn
                100                 105                 110

Val Glu Glu Tyr Glu Lys Asn Leu Lys Thr Ile Val Ala Tyr Leu Lys
            115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Met Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Met Met Leu Gly Leu Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala His Gly Leu Asp Lys Asp Phe Lys Ile Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Thr Thr Gly Gly
                325                 330                 335

Thr Thr Phe Asp Ala Lys Thr Arg Arg Asn Ser Thr Asp Leu Glu Asp
                340                 345                 350

Ile Ile Ile Ala His Ile Ser Gly Met Asp Ala Met Ala Arg Ala Leu
            355                 360                 365

Glu Asn Ala Ala Lys Leu Leu Thr Glu Ser Pro Tyr Lys Lys Met Lys
    370                 375                 380

Ala Asp Arg Tyr Ala Ser Phe Asp Ser Gly Met Gly Lys Asp Phe Glu
385                 390                 395                 400

Asp Gly Lys Leu Thr Phe Glu Gln Val Tyr Glu Tyr Gly Lys Lys Val
                405                 410                 415

Asn Glu Pro Lys Gln Thr Ser Gly Lys Gln Glu Leu Tyr Glu Ala Ile
                420                 425                 430

Val Ala Met Tyr Met
        435

<210> SEQ ID NO 36
<211> LENGTH: 439
<212> TYPE: PRT
<213> ORGANISM: Artificial
<220> FEATURE:
<223> OTHER INFORMATION: Xylose isomerase mutant

<400> SEQUENCE: 36

Met Ala Thr Lys Glu Tyr Phe Pro Gly Ile Gly Lys Ile Lys Phe Glu
1               5                   10                  15

Gly Lys Asp Ser Lys Asn Pro Met Ala Phe Arg Tyr Tyr Asp Ala Glu
            20                  25                  30

Lys Met Ile Asn Gly Arg Ser Met Lys Asp Trp Leu Lys Phe Ala Met
        35                  40                  45

Ala Trp Trp His Thr Leu Cys Ala Glu Gly Gly Asp Gln Phe Gly Gly
 50                  55                  60

Gly Thr Lys Gln Phe Pro Trp Asn Gly Asp Pro Asp Pro Val Gln Ala
 65                  70                  75                  80

Ala Lys Asn Lys Met Asp Ala Gly Phe Glu Phe Met Gln Lys Met Gly
                 85                  90                  95

Ile Gly Tyr Tyr Cys Phe His Asp Val Asp Leu Val Thr Glu Ala Asp
            100                 105                 110

Ser Ile Glu Ala Tyr Glu Ala Asn Leu Lys Glu Leu Val Ala Tyr Ala
        115                 120                 125

Lys Gln Lys Gln Ala Glu Thr Gly Ile Lys Leu Leu Trp Gly Thr Ala
130                 135                 140

Asn Val Phe Ser His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Gly Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asn Gln Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Asp Gly Leu Gly Asn Gly
                325                 330                 335

Gly Thr Thr Phe Asp Ala Lys Thr Arg Arg Asn Ser Thr Asp Pro Glu
            340                 345                 350

Asp Ile Phe Ile Ala His Ile Ala Gly Met Asp Ala Met Ala Arg Ala
        355                 360                 365

Leu Glu Ser Ala Ala Asn Leu Leu Asn Glu Ser Pro Tyr Gln Lys Met
    370                 375                 380

Leu Ser Asp Arg Tyr Ala Ser Phe Asp Ala Gly Lys Gly Lys Glu Phe
385                 390                 395                 400

Glu Glu Gly Lys Leu Ser Leu Glu Glu Leu Val Ala Tyr Ala Lys Ala
                405                 410                 415

Asn Gly Glu Pro Lys Gln Thr Ser Gly Gln Gln Glu Leu Tyr Glu Ala
            420                 425                 430

Leu Val Asn Ile Tyr Ser Leu
        435

<210> SEQ ID NO 37
<211> LENGTH: 437
<212> TYPE: PRT

<213> ORGANISM: Artificial
<220> FEATURE:
<223> OTHER INFORMATION: Xylose isomerase mutant

<400> SEQUENCE: 37

```
Met Thr Lys Glu Tyr Phe Pro Thr Ile Gly Lys Ile Arg Phe Glu Gly
1               5                   10                  15

Lys Asp Ser Lys Asn Pro Met Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Asp Gly Ala Asp Gln Phe Gly Val Gly
    50                  55                  60

Thr Lys Ser Phe Pro Trp Asn Glu Gly Thr Asp Pro Ile Ala Ile Ala
65                  70                  75                  80

Lys Gln Lys Val Asp Ala Gly Phe Glu Ile Met Thr Lys Leu Gly Ile
                85                  90                  95

Glu His Tyr Cys Phe His Asp Val Asp Leu Val Ser Glu Gly Asn Ser
            100                 105                 110

Ile Glu Glu Tyr Glu Ser Asn Leu Lys Gln Val Val Ala Tyr Leu Lys
        115                 120                 125

Gln Lys Gln Gln Glu Thr Gly Ile Lys Leu Leu Trp Ser Thr Ala Asn
    130                 135                 140

Val Phe Gly Asn Pro Arg Tyr Met Asn Gly Ala Ser Thr Asn Pro Asp
145                 150                 155                 160

Phe Asp Val Val Ala Arg Ala Ile Val Gln Ile Lys Asn Ala Met Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
    275                 280                 285

Asp Ala Gly Met Leu Gly Ser Ile Asp Ala Asn Arg Gly Asp Tyr Gln
290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Thr Phe Asp Ala Lys Thr Arg Arg Asn Ser Thr Asp Leu Glu Asp
            340                 345                 350

Ile Ile Ile Ala His Ile Ser Gly Met Asp Ala Met Ala Arg Ala Leu
        355                 360                 365

Glu Asn Ala Ala Lys Leu Leu Gln Glu Ser Pro Tyr Cys Asn Met Lys
    370                 375                 380

Lys Glu Arg Tyr Ala Ser Phe Asp Ser Gly Ile Gly Lys Asp Phe Glu
```

```
                                385                 390                 395                 400
Asp Gly Lys Leu Thr Leu Glu Gln Val Tyr Glu Tyr Gly Lys Lys Asn
                    405                 410                 415
Gly Glu Pro Lys Val Thr Ser Gly Lys Gln Glu Leu Tyr Glu Ala Ile
                420                 425                 430
Val Ala Met Tyr Gln
            435

<210> SEQ ID NO 38
<211> LENGTH: 437
<212> TYPE: PRT
<213> ORGANISM: Artificial
<220> FEATURE:
<223> OTHER INFORMATION: Xylose isomerase mutant

<400> SEQUENCE: 38

Met Ala Lys Glu Tyr Phe Pro Gln Ile Gln Lys Ile Lys Phe Glu Gly
1               5                   10                  15
Lys Asp Ser Lys Asn Pro Leu Ala Phe His Tyr Tyr Asp Ala Glu Lys
            20                  25                  30
Glu Val Met Gly Lys Lys Met Lys Asp Trp Leu Arg Phe Ala Met Ala
        35                  40                  45
Trp Trp His Thr Leu Cys Ala Glu Gly Ala Asp Gln Phe Gly Gly Gly
    50                  55                  60
Thr Lys Ser Phe Pro Trp Asn Glu Gly Thr Asp Ala Ile Glu Ile Ala
65                  70                  75                  80
Lys Gln Lys Val Asp Ala Gly Phe Glu Ile Met Gln Lys Leu Gly Ile
                85                  90                  95
Pro Tyr Tyr Cys Phe His Asp Val Asp Leu Val Ser Glu Gly Asn Ser
            100                 105                 110
Ile Glu Glu Tyr Glu Ser Asn Leu Lys Ala Val Val Ala Tyr Leu Lys
        115                 120                 125
Glu Lys Gln Lys Glu Thr Gly Ile Lys Leu Leu Trp Ser Thr Ala Asn
    130                 135                 140
Val Phe Gly His Lys Arg Tyr Met Asn Gly Ala Ser Thr Asn Pro Asp
145                 150                 155                 160
Phe Asp Val Val Ala Arg Ala Ile Val Gln Ile Lys Asn Ala Ile Asp
                165                 170                 175
Ala Gly Ile Glu Leu Gly Ala Glu Asn Tyr Val Phe Trp Gly Gly Arg
            180                 185                 190
Glu Gly Tyr Met Ser Leu Leu Asn Thr Asp Gln Lys Arg Glu Lys Glu
        195                 200                 205
His Met Ala Thr Met Leu Thr Met Ala Arg Asp Tyr Ala Arg Ser Lys
    210                 215                 220
Gly Phe Lys Gly Thr Phe Leu Ile Glu Pro Lys Pro Met Glu Pro Thr
225                 230                 235                 240
Lys His Gln Tyr Asp Val Asp Thr Glu Thr Ala Ile Gly Phe Leu Lys
                245                 250                 255
Ala His Asn Leu Asp Lys Asp Phe Lys Val Asn Ile Glu Val Asn His
            260                 265                 270
Ala Thr Leu Ala Gly His Thr Phe Glu His Glu Leu Ala Cys Ala Val
        275                 280                 285
Asp Ala Gly Met Leu Gly Ser Ile Asp Ala Asn Arg Gly Asp Tyr Gln
    290                 295                 300
Asn Gly Trp Asp Thr Asp Gln Phe Pro Ile Asp Gln Tyr Glu Leu Val
```

```
            305                 310                 315                 320
      Gln Ala Trp Met Glu Ile Ile Arg Gly Gly Gly Phe Val Thr Gly Gly
                      325                 330                 335

Thr Thr Phe Asp Ala Lys Thr Arg Arg Asn Ser Thr Asp Leu Glu Asp
                      340                 345                 350

Ile Ile Ile Ala His Val Ser Gly Met Asp Ala Met Arg Ala Leu
                      355                 360                 365

Glu Asn Ala Ala Lys Leu Leu Gln Glu Ser Pro Tyr Thr Lys Met Lys
                      370                 375                 380

Lys Glu Arg Tyr Ala Ser Phe Asp Ser Gly Ile Gly Lys Asp Phe Glu
      385                 390                 395                 400

Asp Gly Lys Leu Thr Leu Glu Gln Val Tyr Glu Tyr Gly Lys Lys Asn
                      405                 410                 415

Gly Glu Pro Lys Gln Thr Ser Gly Lys Gln Glu Leu Tyr Glu Ala Ile
                      420                 425                 430

Val Ala Met Tyr Gln
                      435

<210> SEQ ID NO 39
<211> LENGTH: 439
<212> TYPE: PRT
<213> ORGANISM: Artificial
<220> FEATURE:
<223> OTHER INFORMATION: Xylose isomerase mutant

<400> SEQUENCE: 39

Met Ala Tyr Phe Asn Asp Ile Ala Pro Ile Lys Tyr Glu Gly Thr Lys
      1               5                   10                  15

Thr Lys Asn Met Phe Ala Phe Arg His Tyr Asn Pro Glu Glu Val Val
                      20                  25                  30

Ala Gly Lys Thr Met Glu Glu Gln Leu His Phe Ala Leu Ala Phe Trp
                      35                  40                  45

His Thr Ile Thr Met Asp Gly Ser Asp Pro Phe Gly Gly Ala Thr Met
                      50                  55                  60

Glu Arg Pro Trp Asp Leu Glu Gly Gly Ser Glu Leu Asp Arg Ala His
      65                  70                  75                  80

Arg Arg Val Asp Ala Phe Phe Glu Ile Ala Glu Lys Leu Gly Val Lys
                      85                  90                  95

Tyr Tyr Cys Phe His Asp Ile Asp Ile Ala Pro Thr Gly Asn Ser Leu
                      100                 105                 110

Lys Glu Phe Tyr Ala Asn Leu Asp Glu Ile Thr Asp His Leu Leu Glu
                      115                 120                 125

Lys Gln Lys Ala Thr Gly Ile Lys Leu Leu Trp Asn Thr Ala Asn Met
                      130                 135                 140

Phe Ser Asn Pro Arg Tyr Met Asn Gly Val Ser Thr Ser Asn Arg Ala
      145                 150                 155                 160

Glu Val Phe Ala Tyr Gly Ala Ala Gln Val Lys Lys Gly Leu Glu Leu
                      165                 170                 175

Ser Lys Lys Leu Gly Gly Glu Asn Tyr Val Phe Trp Gly Gly Arg Glu
                      180                 185                 190

Gly Tyr Glu Ser Leu Leu Asn Thr Asp Met Gly Leu Glu Met Asp His
                      195                 200                 205

Met Ala Lys Phe Phe His Leu Ala Ile Asp Tyr Ala Lys Ser Ile Asn
                      210                 215                 220

His Leu Pro Ile Phe Leu Ile Glu Pro Lys Pro Lys Glu Pro Met Thr
```

```
                225                 230                 235                 240
His Gln Tyr Asp Phe Asp Ser Ala Thr Ala Leu Ala Phe Leu Gln Lys
                245                 250                 255

Tyr Asp Leu Asp Lys Tyr Phe Lys Leu Asn Leu Glu Thr Asn His Ala
                260                 265                 270

Trp Leu Ala Gly His Thr Phe Glu His Glu Leu Asn Thr Ala Arg Thr
                275                 280                 285

Phe Asn Ala Leu Gly Ser Ile Asp Ala Asn Gln Gly Asn Tyr Leu Leu
                290                 295                 300

Gly Trp Asp Thr Asp Glu Phe Pro Thr Leu Val Ile Asp Ile Thr Leu
305                 310                 315                 320

Ala Met His Gln Ile Leu Leu Asn Gly Gly Leu Gly Lys Gly Gly Ile
                325                 330                 335

Thr Phe Asp Ala Lys Val Arg Arg Thr Ser Phe Lys Ala Glu Asp Leu
                340                 345                 350

Ile Leu Ala His Ile Ala Gly Met Asp Thr Tyr Ala Arg Ala Leu Lys
                355                 360                 365

Gly Ala Ala Ile Ile Glu Asp Lys Phe Leu Ser Asp Ile Val Asp
        370                 375                 380

Glu Arg Tyr Ser Ser Tyr Lys Asn Thr Glu Val Gly Gln Ser Ile Glu
385                 390                 395                 400

Asn Gly Thr Ala Thr Phe Glu Ser Leu Ala Ala Phe Ala Leu Glu Tyr
                405                 410                 415

Gly Asp Asp Ile Glu Leu Asp Ser Asn His Leu Glu Tyr Ile Lys Ser
                420                 425                 430

Val Leu Asn Asp Tyr Leu Val
        435

<210> SEQ ID NO 40
<211> LENGTH: 456
<212> TYPE: PRT
<213> ORGANISM: Artificial
<220> FEATURE:
<223> OTHER INFORMATION: Xylose isomerase mutant

<400> SEQUENCE: 40

Met Ser Ser Phe Ala Pro Ala Ser Gly Lys Ser Asp Leu Ala Glu Ala
1               5                   10                  15

Gly Ser Leu Leu Thr Lys Tyr Pro Leu Glu Val Lys Lys Ile Pro Tyr
                20                  25                  30

Lys Pro Asp Ala Lys Val Asp Asp Val Leu Cys Phe Arg His Tyr Asn
                35                  40                  45

Glu Ser Glu Val Val Met Gly Lys Pro Met Ser Asp Trp Leu Arg Phe
            50                  55                  60

Ser Val Cys Tyr Trp His Thr Phe Arg Gly Thr Gly Ala Asp Pro Phe
65                  70                  75                  80

Gly Phe Pro Thr Leu Val Arg Pro Trp Asp Asp Gly Thr Asp Ser Ile
                85                  90                  95

Glu Asn Ala Glu Arg Arg Met Arg Val Ala Phe Asp Phe Met Ser Lys
                100                 105                 110

Leu Gly Val Lys Tyr Trp Thr Phe His Asp Arg Asp Ile Ala Pro Glu
            115                 120                 125

Gly Val Thr Leu Ser Glu Thr Asn Ala Asn Leu Asp Arg Leu Ala Glu
        130                 135                 140

Leu Ala Ser Gln Leu Gln Gly Glu Thr Gly Ile Lys Leu Leu Trp Asn
```

| | | | | | | | | | | | | | | |
|---|---|---|---|---|---|---|---|---|---|---|---|---|---|---|
| | 145 | | | | 150 | | | | 155 | | | | 160 | |
| Thr | Cys | Asn | Leu | Phe | Ala | His | Pro | Arg | Tyr | Ser | Asn | Gly | Ala | Ala | Thr |
| | | | | 165 | | | | | 170 | | | | | 175 |
| Asn | Ala | Asp | Ala | His | Val | Val | Ala | Tyr | Ala | Ala | Gln | Val | Lys | Lys |
| | | | 180 | | | | | 185 | | | | 190 | | |
| Ser | Leu | Glu | Ile | Gly | Lys | Lys | Leu | Gly | Ala | Glu | Asn | Phe | Val | Phe | Trp |
| | | 195 | | | | | 200 | | | | | 205 | | |
| Gly | Gly | Arg | Glu | Gly | Tyr | His | Thr | Leu | Leu | Asn | Thr | Asn | Val | Arg | Glu |
| | 210 | | | | | 215 | | | | | 220 | | | |
| Glu | Leu | Asp | Asn | Leu | Ala | Asn | Phe | Phe | Lys | Met | Val | Val | Ala | Tyr | Lys |
| 225 | | | | | 230 | | | | | 235 | | | | | 240 |
| Lys | Lys | Ile | Gly | Phe | Thr | Gly | Gln | Phe | Leu | Ile | Glu | Pro | Lys | Pro | Lys |
| | | | | 245 | | | | | 250 | | | | | 255 | |
| Glu | Pro | Ser | Lys | His | Gln | Tyr | Asp | Tyr | Asp | Ala | Met | Thr | Val | Ile | Ala |
| | | | 260 | | | | | 265 | | | | | 270 | | |
| Phe | Leu | Lys | Thr | Tyr | Asp | Leu | Asp | Lys | Asp | Phe | Lys | Leu | Asn | Ile | Glu |
| | | 275 | | | | | 280 | | | | | 285 | | | |
| Pro | Asn | His | Thr | Thr | Leu | Ala | Gly | His | Cys | His | Glu | His | Asp | Val | Val |
| | 290 | | | | | 295 | | | | | 300 | | | | |
| Met | Ala | Ser | Ala | Tyr | Asn | Met | Leu | Gly | Ser | Val | Asp | Ser | Asn | Thr | Gly |
| 305 | | | | | 310 | | | | | 315 | | | | | 320 |
| Ser | Pro | Asp | Leu | Gly | Trp | Asp | Thr | Asp | Gln | Phe | Pro | Met | Asp | Val | Lys |
| | | | | 325 | | | | | 330 | | | | | 335 | |
| Asn | Ala | Thr | Met | Ile | Met | Gln | Thr | Val | Leu | Glu | Gln | Gly | Gly | Leu | Ala |
| | | | 340 | | | | | 345 | | | | | 350 | | |
| Pro | Gly | Gly | Leu | Thr | Phe | Asp | Cys | Lys | Val | Arg | Arg | Glu | Ser | Thr | Asp |
| | | 355 | | | | | 360 | | | | | 365 | | | |
| Val | Ile | Asp | Met | Met | Ile | Ala | His | Val | Gly | Ala | Met | Asp | Cys | Phe | Ala |
| | 370 | | | | | 375 | | | | | 380 | | | | |
| Lys | Ala | Leu | Lys | Ile | Ala | Ala | Lys | Ile | Arg | Glu | Asp | Gly | Val | Leu | Gly |
| 385 | | | | | 390 | | | | | 395 | | | | | 400 |
| Lys | Met | Lys | Lys | Glu | Arg | Tyr | Ala | Ser | Phe | Gly | Ser | Gly | Leu | Gly | Leu |
| | | | | 405 | | | | | 410 | | | | | 415 | |
| Lys | Ile | Lys | Thr | Gly | Thr | Ala | Thr | Leu | Glu | Glu | Cys | Asp | Ser | Phe | Ile |
| | | | 420 | | | | | 425 | | | | | 430 | | |
| Gln | Glu | Asn | Gly | Glu | Pro | Ala | Lys | Leu | Ser | Gly | Lys | Gln | Glu | Met | Phe |
| | | 435 | | | | | 440 | | | | | 445 | | | |
| Glu | Ala | Val | Leu | Asn | Arg | Tyr | Phe | | | | | | | | |
| | 450 | | | | | 455 | | | | | | | | | |

<210> SEQ ID NO 41
<211> LENGTH: 49
<212> TYPE: DNA
<213> ORGANISM: Artificial
<220> FEATURE:
<223> OTHER INFORMATION: Primer

<400> SEQUENCE: 41
gaacttagtt tcgaataaac acacataaac aaacaaaccg cggaaaatg         49

<210> SEQ ID NO 42
<211> LENGTH: 49
<212> TYPE: DNA
<213> ORGANISM: Artificial
<220> FEATURE:
<223> OTHER INFORMATION: Primer

<400> SEQUENCE: 42
gtgaatgtaa gcgtgacata actaattaca tgatgcggcc ctcgagtta                49

<210> SEQ ID NO 43
<211> LENGTH: 35
<212> TYPE: DNA
<213> ORGANISM: Artificial
<220> FEATURE:
<223> OTHER INFORMATION: Primer

<400> SEQUENCE: 43
tcgctattac gccagctggc gaaaggggga tgtgc                                35

<210> SEQ ID NO 44
<211> LENGTH: 45
<212> TYPE: DNA
<213> ORGANISM: Artificial
<220> FEATURE:
<223> OTHER INFORMATION: Primer

<400> SEQUENCE: 44
gattcattaa tgcagctggc acgacaggtt tcccgactgg aaagc                     45

<210> SEQ ID NO 45
<211> LENGTH: 56
<212> TYPE: DNA
<213> ORGANISM: Artificial
<220> FEATURE:
<223> OTHER INFORMATION: Primer

<400> SEQUENCE: 45
attaaggcag gtggtttgac cggtggtttg cttttgatt ccaaggttag aagacc          56

<210> SEQ ID NO 46
<211> LENGTH: 56
<212> TYPE: DNA
<213> ORGANISM: Artificial
<220> FEATURE:
<223> OTHER INFORMATION: Primer

<400> SEQUENCE: 46
attaaggcag gtggtttgac cggtggtttg agatttgatt ccaaggttag aagacc         56

<210> SEQ ID NO 47
<211> LENGTH: 56
<212> TYPE: DNA
<213> ORGANISM: Artificial
<220> FEATURE:
<223> OTHER INFORMATION: Primer

<400> SEQUENCE: 47
attaaggcag gtggtttgac cggtggtttg gattttgatt ccaaggttag aagacc         56

<210> SEQ ID NO 48
<211> LENGTH: 56
<212> TYPE: DNA
<213> ORGANISM: Artificial
<220> FEATURE:
<223> OTHER INFORMATION: Primer

<400> SEQUENCE: 48
attaaggcag gtggtttgac cggtggtttg tgttttgatt ccaaggttag aagacc         56

<210> SEQ ID NO 49
<211> LENGTH: 56

<212> TYPE: DNA
<213> ORGANISM: Artificial
<220> FEATURE:
<223> OTHER INFORMATION: Primer

<400> SEQUENCE: 49
attaaggcag gtggtttgac cggtggtttg caatttgatt ccaaggttag aagacc    56

<210> SEQ ID NO 50
<211> LENGTH: 56
<212> TYPE: DNA
<213> ORGANISM: Artificial
<220> FEATURE:
<223> OTHER INFORMATION: Primer

<400> SEQUENCE: 50
attaaggcag gtggtttgac cggtggtttg gaatttgatt ccaaggttag aagacc    56

<210> SEQ ID NO 51
<211> LENGTH: 56
<212> TYPE: DNA
<213> ORGANISM: Artificial
<220> FEATURE:
<223> OTHER INFORMATION: Primer

<400> SEQUENCE: 51
attaaggcag gtggtttgac cggtggtttg ggttttgatt ccaaggttag aagacc    56

<210> SEQ ID NO 52
<211> LENGTH: 56
<212> TYPE: DNA
<213> ORGANISM: Artificial
<220> FEATURE:
<223> OTHER INFORMATION: Primer

<400> SEQUENCE: 52
attaaggcag gtggtttgac cggtggtttg cattttgatt ccaaggttag aagacc    56

<210> SEQ ID NO 53
<211> LENGTH: 56
<212> TYPE: DNA
<213> ORGANISM: Artificial
<220> FEATURE:
<223> OTHER INFORMATION: Primer

<400> SEQUENCE: 53
attaaggcag gtggtttgac cggtggtttg attttgatt ccaaggttag aagacc    56

<210> SEQ ID NO 54
<211> LENGTH: 56
<212> TYPE: DNA
<213> ORGANISM: Artificial
<220> FEATURE:
<223> OTHER INFORMATION: Primer

<400> SEQUENCE: 54
attaaggcag gtggtttgac cggtggtttg ttgtttgatt ccaaggttag aagacc    56

<210> SEQ ID NO 55
<211> LENGTH: 56
<212> TYPE: DNA
<213> ORGANISM: Artificial
<220> FEATURE:
<223> OTHER INFORMATION: Primer

<400> SEQUENCE: 55
attaaggcag gtggtttgac cggtggtttg aaatttgatt ccaaggttag aagacc        56

<210> SEQ ID NO 56
<211> LENGTH: 56
<212> TYPE: DNA
<213> ORGANISM: Artificial
<220> FEATURE:
<223> OTHER INFORMATION: Primer

<400> SEQUENCE: 56
attaaggcag gtggtttgac cggtggtttg atgtttgatt ccaaggttag aagacc        56

<210> SEQ ID NO 57
<211> LENGTH: 56
<212> TYPE: DNA
<213> ORGANISM: Artificial
<220> FEATURE:
<223> OTHER INFORMATION: Primer

<400> SEQUENCE: 57
attaaggcag gtggtttgac cggtggtttg tttttgatt ccaaggttag aagacc         56

<210> SEQ ID NO 58
<211> LENGTH: 56
<212> TYPE: DNA
<213> ORGANISM: Artificial
<220> FEATURE:
<223> OTHER INFORMATION: Primer

<400> SEQUENCE: 58
attaaggcag gtggtttgac cggtggtttg ccatttgatt ccaaggttag aagacc        56

<210> SEQ ID NO 59
<211> LENGTH: 56
<212> TYPE: DNA
<213> ORGANISM: Artificial
<220> FEATURE:
<223> OTHER INFORMATION: Primer

<400> SEQUENCE: 59
attaaggcag gtggtttgac cggtggtttg tcttttgatt ccaaggttag aagacc        56

<210> SEQ ID NO 60
<211> LENGTH: 56
<212> TYPE: DNA
<213> ORGANISM: Artificial
<220> FEATURE:
<223> OTHER INFORMATION: Primer

<400> SEQUENCE: 60
attaaggcag gtggtttgac cggtggtttg tggtttgatt ccaaggttag aagacc        56

<210> SEQ ID NO 61
<211> LENGTH: 56
<212> TYPE: DNA
<213> ORGANISM: Artificial
<220> FEATURE:
<223> OTHER INFORMATION: Primer

<400> SEQUENCE: 61
attaaggcag gtggtttgac cggtggtttg tattttgatt ccaaggttag aagacc        56

<210> SEQ ID NO 62
<211> LENGTH: 56
<212> TYPE: DNA
<213> ORGANISM: Artificial

```
<220> FEATURE:
<223> OTHER INFORMATION: Primer

<400> SEQUENCE: 62
attaaggcag gtggtttgac cggtggtttg gtttttgatt ccaaggttag aagacc     56

<210> SEQ ID NO 63
<211> LENGTH: 69
<212> TYPE: DNA
<213> ORGANISM: Artificial
<220> FEATURE:
<223> OTHER INFORMATION: Primer

<400> SEQUENCE: 63
ataaacaaac aaaccgcgga aaatggctaa ggaatacttc ccacaaatcc aaagattaa   60 attcgaggg                                                         69

<210> SEQ ID NO 64
<211> LENGTH: 57
<212> TYPE: DNA
<213> ORGANISM: Artificial
<220> FEATURE:
<223> OTHER INFORMATION: Primer

<400> SEQUENCE: 64
agtagagttt cttctggttt ttgcatcgaa agtggtacca cctgtaacaa aaccacc     57

<210> SEQ ID NO 65
<211> LENGTH: 53
<212> TYPE: DNA
<213> ORGANISM: Artificial
<220> FEATURE:
<223> OTHER INFORMATION: Primer

<400> SEQUENCE: 65
atcagaggtg gtggttttgt tacaggtggt accactttcg atgcaaaaac cag         53

<210> SEQ ID NO 66
<211> LENGTH: 63
<212> TYPE: DNA
<213> ORGANISM: Artificial
<220> FEATURE:
<223> OTHER INFORMATION: Primer

<400> SEQUENCE: 66
tgatgcggcc ctcgagttat tggtacatag caacaattgc ttcatacaat tcttgtttac  60
cac                                                               63

<210> SEQ ID NO 67
<211> LENGTH: 69
<212> TYPE: DNA
<213> ORGANISM: Artificial
<220> FEATURE:
<223> OTHER INFORMATION: Primer

<400> SEQUENCE: 67
ataaacaaac aaaccgcgga aaatgaagaa ttacttccca aatgtcccag aagtgaaata  60
tgaaggccc                                                         69

<210> SEQ ID NO 68
<211> LENGTH: 63
<212> TYPE: DNA
<213> ORGANISM: Artificial
<220> FEATURE:
```

```
<223> OTHER INFORMATION: Primer

<400> SEQUENCE: 68
actgcctctt ctaaccttag catcaaaagt tagaccacca ttagtaaagc ctccagcttt     60
cag                                                                   63

<210> SEQ ID NO 69
<211> LENGTH: 61
<212> TYPE: DNA
<213> ORGANISM: Artificial
<220> FEATURE:
<223> OTHER INFORMATION: Primer

<400> SEQUENCE: 69
tgaaagctgg aggctttact aatggtggtc taacttttga tgctaaggtt agaagaggca     60
g                                                                     61

<210> SEQ ID NO 70
<211> LENGTH: 63
<212> TYPE: DNA
<213> ORGANISM: Artificial
<220> FEATURE:
<223> OTHER INFORMATION: Primer

<400> SEQUENCE: 70
tgatgcggcc ctcgagtcat ctaaacaaga tgttattgac aatagtctcc aagacttctt     60
gtc                                                                   63

<210> SEQ ID NO 71
<211> LENGTH: 1320
<212> TYPE: DNA
<213> ORGANISM: Artificial
<220> FEATURE:
<223> OTHER INFORMATION: Mutated xylose isomerase

<400> SEQUENCE: 71
atgtctcaaa tttttaagga tatcccagtt attaaatatg aaggtccagc ttccaagaat     60
cctttgagtt tcaaatacta cgatgcaaac aaggttattg atggtaaacc aatgaaggaa    120
catttgagat acgcaatggc ttggtggcat aatttgtgtg ctaccggtca agatatgttt    180
ggtcctggta ctgcagataa atccttcggt agtaagacag ttggtaccat ggaacatgca    240
catgctaaag ttgatgctgg ttttgaattc atgtccaagt gggtgttga atacttctgt    300 ttccatgatg ctgatttggt tccagaagca gatactttga gtgaaacaaa caaaagattg    360
gatgaaatcg ctgaacatat cgttgctaag caaaaggcaa ctggtattaa atgtttgtgg    420
ggtacagcaa atttgttttc taaccctaga ttcttaaatg ttctggttc ttcaaactca    480 gctgatgttt atgcatacgc tgcagctcaa attaaaaagg ctttggattt gactgttaaa    540
tttggtggtg ttggttatgt tttctggggt ggtagagaag gttacgaaac cttgttgaac    600
actgatgtta agttcgaaca agaaaacatc gctaacttga tgcatttggc agttacttac    660
ggtagatcaa tcggttttaa aggtgacttc tacattgaac caaaacctaa ggaaccaaca    720
aagcatcaat atgattttga tgcagctact acaattggtt tcattagaca atacggtttg    780
gaaaaggatt tcaagttgaa catcgaagca accatgcta cattagcagg tcataccttc    840
caacatgatt tgagaatctc tgctattaat ggcatgttag ttcagttga tgcaaacaca    900 ggtgacccat tgttaggttg ggataccgat gaatttcctt attccgttta cgataccact    960
ttggctatgt acgaaattat taaggcaggt ggtttgaccg gtggtttgac ttttgattcc    1020
```

```
aaggttagaa gaccaagtta cacacatgaa gatttgtttt acggtttcat tttgggtatg    1080
gattctttcg ctttgggttt gattaaagca aaggctttga ttgcagatgg tagattggat    1140
tcattcgtta aggatagata cgcttcttac ggttcaggta ttggtgctaa gattagagat    1200
cattctgcaa ctttggaaga attagcagct tatgcattag ctaaagatac agttgctttg    1260
cctggttccg gtagacaaga atacttagaa agtattatta accaaatttt gtttcaataa    1320
```

<210> SEQ ID NO 72
<211> LENGTH: 1320
<212> TYPE: DNA
<213> ORGANISM: Artificial
<220> FEATURE:
<223> OTHER INFORMATION: Mutated xylose isomerase

<400> SEQUENCE: 72

```
atgtctcaaa ttttaagga tatcccagtt attaaatatg aaggtccagc ttccaagaat      60
cctttgagtt tcaaatacta cgatgcaaac aaggttattg atggtaaacc aatgaaggaa    120
catttgagat acgcaatggc ttggtggcat aatttgtgtg ctaccggtca agatatgttt    180
ggtcctggta ctgcagataa atccttcggt agtaagacag ttggtaccat ggaacatgca    240
catgctaaag ttgatgctgg ttttgaattc atgtccaagt gggtgttga atacttctgt     300 ttccatgatg ctgatttggt tccagaagca gatactttga gtgaaacaaa caaaagattg    360
gatgaaatcg ctgaacatat cgttgctaag caaaaggcaa ctggtattaa atgtttgtgg    420
ggtacagcaa atttgttttc taaccctaga ttcttaaatg gttctggttc ttcaaactca    480
gctgatgttt atgcatacgc tgcagctcaa attaaaaagg ctttggattt gactgttaaa    540
tttggtggtg ttggttatgt tttctgggg ggtagagaag gttacgaaac cttgttgaac    600
actgatgtta agttcgaaca agaaaacatc gctaacttga tgcatttggc agttacttac    660
ggtagatcaa tcggttttaa aggtgacttc tacattgaac aaaaacctaa ggaaccaaca    720
aagcatcaat atgattttga tgcagctact acaattggtt tcattagaca atacggtttg    780
gaaaaggatt tcaagttgaa catcgaagca aaccatgcta cattagcagg tcataccttc    840
caacatgatt tgagaatctc tgctattaat ggcatgttag gttcagttga tgcaaacaca    900
ggtgacccat tgttaggttg ggatacccgat gaatttcctt attccgttta cgataccact    960
ttggctatgt acgaaattat taaggcaggt ggtttgaccg gtggtttgtg ttttgattcc   1020
aaggttagaa gaccaagtta cacacatgaa gatttgtttt acggtttcat tttgggtatg  1080
gattctttcg ctttgggttt gattaaagca aaggctttga ttgcagatgg tagattggat  1140
tcattcgtta aggatagata cgcttcttac ggttcaggta ttggtgctaa gattagagat  1200
cattctgcaa ctttggaaga attagcagct tatgcattag ctaaagatac agttgctttg  1260
cctggttccg gtagacaaga atacttagaa agtattatta accaaatttt gtttcaataa  1320
```

<210> SEQ ID NO 73
<211> LENGTH: 1320
<212> TYPE: DNA
<213> ORGANISM: Artificial
<220> FEATURE:
<223> OTHER INFORMATION: Mutated xylose isomerase

<400> SEQUENCE: 73

```
atgtctcaaa ttttaagga tatcccagtt attaaatatg aaggtccagc ttccaagaat      60
cctttgagtt tcaaatacta cgatgcaaac aaggttattg atggtaaacc aatgaaggaa    120
```

```
catttgagat acgcaatggc ttggtggcat aatttgtgtg ctaccggtca agatatgttt    180
ggtcctggta ctgcagataa atccttcggt agtaagacag ttggtaccat ggaacatgca    240
catgctaaag ttgatgctgg ttttgaattc atgtccaagt gggtgttga atacttctgt     300
ttccatgatg ctgatttggt tccagaagca gatactttga gtgaaacaaa caaaagattg    360
gatgaaatcg ctgaacatat cgttgctaag caaaaggcaa ctggtattaa atgtttgtgg    420
ggtacagcaa atttgttttc taaccctaga ttcttaaatg ttctggttc ttcaaactca     480
gctgatgttt atgcatacgc tgcagctcaa attaaaaagg ctttggattt gactgttaaa    540
tttggtggtg ttggttatgt tttctggggt ggtagagaag ttacgaaac cttgttgaac     600
actgatgtta agttcgaaca agaaaacatc gctaacttga tgcatttggc agttacttac    660
ggtagatcaa tcggttttaa aggtgacttc tacattgaac caaaacctaa ggaaccaaca    720
aagcatcaat atgattttga tgcagctact acaattggtt tcattagaca atacggtttg    780
gaaaaggatt tcaagttgaa catcgaagca aaccatgcta cattagcagg tcataccttc    840
caacatgatt tgagaatctc tgctattaat ggcatgttag gttcagttga tgcaaacaca    900
ggtgacccat tgttaggttg ggataccgat gaatttcctt attccgttta cgataccact    960
ttggctatgt acgaaattat taaggcaggt ggtttgaccg tggtttggt ttttgattcc     1020
aaggttagaa gaccaagtta cacacatgaa gatttgtttt acggtttcat tttgggtatg    1080
gattctttcg ctttggggttt gattaaagca aaggctttga ttgcagatgg tagattggat    1140
tcattcgtta aggatagata cgcttcttac ggttcaggta ttggtgctaa gattagagat    1200
cattctgcaa ctttggaaga attagcagct tatgcattag ctaaagatac agttgctttg    1260
cctggttccg gtagacaaga atacttagaa agtattatta accaaatttt gtttcaataa    1320
```

<210> SEQ ID NO 74
<211> LENGTH: 1320
<212> TYPE: DNA
<213> ORGANISM: Artificial
<220> FEATURE:
<223> OTHER INFORMATION: Mutated xylose isomerase

<400> SEQUENCE: 74

```
atgtctcaaa tttttaagga tatcccagtt attaaatatg aaggtccagc ttccaagaat     60
cctttgagtt tcaaatacta cgatgcaaac aaggttattg atggtaaacc aatgaaggaa    120
catttgagat acgcaatggc ttggtggcat aatttgtgtg ctaccggtca agatatgttt    180
ggtcctggta ctgcagataa atccttcggt agtaagacag ttggtaccat ggaacatgca    240
catgctaaag ttgatgctgg ttttgaattc atgtccaagt gggtgttga atacttctgt     300
ttccatgatg ctgatttggt tccagaagca gatactttga gtgaaacaaa caaaagattg    360
gatgaaatcg ctgaacatat cgttgctaag caaaaggcaa ctggtattaa atgtttgtgg    420
ggtacagcaa atttgttttc taaccctaga ttcttaaatg ttctggttc ttcaaactca     480
gctgatgttt atgcatacgc tgcagctcaa attaaaaagg ctttggattt gactgttaaa    540
tttggtggtg ttggttatgt tttctggggt ggtagagaag ttacgaaac cttgttgaac     600
actgatgtta agttcgaaca agaaaacatc gctaacttga tgcatttggc agttacttac    660
ggtagatcaa tcggttttaa aggtgacttc tacattgaac caaaacctaa ggaaccaaca    720
aagcatcaat atgattttga tgcagctact acaattggtt tcattagaca atacggtttg    780
gaaaaggatt tcaagttgaa catcgaagca aaccatgcta cattagcagg tcataccttc    840
caacatgatt tgagaatctc tgctattaat ggcatgttag gttcagttga tgcaaacaca    900
```

```
ggtgacccat tgttaggttg ggataccgat gaatttcctt attccgttta cgataccact      960
ttggctatgt acgaaattat taaggcaggt ggtttgaccg gtggtttggc ttttgattcc     1020
aaggttagaa gaccaagtta cacacatgaa gatttgtttt acggtttcat tttgggtatg     1080
gattctttcg ctttgggttt gattaaagca aaggctttga ttgcagatgg tagattggat     1140
tcattcgtta aggatagata cgcttcttac ggttcaggta ttggtgctaa gattagagat     1200
cattctgcaa ctttggaaga attagcagct tatgcattag ctaaagatac agttgctttg     1260
cctggttccg gtagacaaga atacttagaa agtattatta accaaatttt gtttcaataa     1320
```

<210> SEQ ID NO 75
<211> LENGTH: 1314
<212> TYPE: DNA
<213> ORGANISM: Artificial
<220> FEATURE:
<223> OTHER INFORMATION: Mutated xylose isomerase

<400> SEQUENCE: 75

```
atggctaagg aatacttccc acaaatccaa aagattaaat tcgagggtaa agattctaaa       60
aatcctttgg cattccatta ctacgatgct gaaaaggaag ttatgggtaa aaagatgaag      120
gattggttga gattcgctat ggcatggtgg catactttgt gtgcagaagg tgctgatcaa      180
tttggtggtg gtactaagtc attcccatgg aacgaaggta cagatgcaat cgaaatcgct      240
aagcaaaagg ttgatgctgg tttcgaaatc atgcaaaagt gggtatccc ttactactgt       300 ttccatgatg ttgatttggt ttccgagggt aacagtatcg aagaatacga atccaacttg      360
aaagcagttg ttgcttactt aaaggaaaag caaaaggaaa caggtattaa gttgttgtgg      420
tccaccgcaa acgttttcgg tcataagaga tacatgaacg gtgctagtac taacccagat      480
ttcgatgttg ttgctagagc aatcgttcaa attaaaaatg caatcgatgc tggtattgaa      540
ttgggtgcag aaaactatgt tttctggggt ggtagagaag gttacatgtc tttgttgaac      600
acagatcaaa agagagaaaa agaacatatg gctaccatgt taactatggc aagagattat      660
gctagatcaa agggttttaa aggtaccttc ttgattgaac caaagcctat ggaaccaact      720
aaacatcaat acgatgttga tactgaaaca gcaattggtt tcttgaaggc tcataatttg      780
gataaggatt tcaaggttaa catcgaagtt aaccatgcaa ctttggctgg tcatacattt      840
gaacatgaat tagcttgtgc agttgatgca ggcatgttgg ttctattga tgctaatcgt      900 ggtgactatc aaaacggttg ggatactgat caattcccta tcgatcaata cgaattagtt     960
caagcttgga tggaaatcat cagaggtggt ggttttgtta caggtggtac cactttcgat     1020
gcaaaaacca agaaactc tactgatttg gaagatatca tcatcgctca tgtttctggt     1080
atggatgcta tggcaagagc tttggaaaat gctgcaaagt tgttacaaga tccccatac      1140 acaaagatga aaaggaaag atacgcttct ttcgattcag gtatcggtaa agatttcgaa      1200
gatggtaaat tgacattaga acaagtttac gaatacggta aaaagaacgg tgaacctaag     1260
caaaccagtg gtaaacaaga attgtatgaa gcaattgttg ctatgtacca ataa           1314
```

<210> SEQ ID NO 76
<211> LENGTH: 1317
<212> TYPE: DNA
<213> ORGANISM: Artificial
<220> FEATURE:
<223> OTHER INFORMATION: Mutated xylose isomerase

<400> SEQUENCE: 76

```
atgaagaatt acttcccaaa tgtcccagaa gtgaaatatg aaggcccccaa ttcaaccaac      60 ccatttgcat tcaaatacta cgacgcaaac aaggttgttg caggaaaaac tatgaaagag     120
cactgtaggt ttgcacttag ctggtggcat actttatgcg caggtggagc tgacccgttc     180
ggagttacta ctatggacag aacgtacggt aacattactg acccaatgga actagcaaaa     240
gcaaaagttg acgcaggttt tgaactgatg accaagcttg gtattgaatt tttttgtttt     300
catgacgctg atattgcccc agaaggtgac acgttcgaag aatccaaaaa aaatctattt     360
gaaattgtag attatataaa ggaaaaaatg gatcaaacag gaatcaaact actttggggt     420
actgccaata atttttctca tccccgtttt atgcacggcg catccacatc ttgtaacgct     480
gacgtgttcg cgtacgccgc tgcaaagatc aaaaacgcgt tggatgccac tataaaattg     540
ggtggtaaag gttacgtctt ctgggggggt agggaaggtt acgagacctt gcttaacact     600
gatctgggtt tggaattaga caatatggcc agattaatga aaatggcagt tgaatacgga     660
agagcaaatg gcttcgatgg cgatttttat atagagccca aacctaaaga gcctactaaa     720
catcaatatg actttgacac cgcgactgtc ttagcctttt taagaaagta cgggcttgaa     780
aaagacttca aaatgaatat cgaagccaac catgcgacgt tggctggtca tacctttgag     840
catgagctag ccatggcaag agtcaatggc gcctttgggt ctgtcgatgc taatcagggc     900
gatcctaacc ttggatggga tacggatcaa tttcctacag atgttcactc agcaacactt     960
gcaatgttgg aagttctgaa agctggaggc tttactaatg gtggtctaac ttttgatgct    1020
aaggttagaa gaggcagttt cgaatttgac gacatcgcat acggttatat tgctggtatg    1080
gacacgttcg ctttaggcct gattaaagcc gctgaaatta ttgatgatgg cagaatagct    1140
aagtttgttg atgacagata cgcaagttac aaaaccggta ttggtaaggc catcgtagac    1200
gggactacta gcttggaaga acttgaacag tatgttttga ctcattccga accagtaatg    1260
caatctggta gacaagaagt cttggagact attgtcaata acatcttgtt tagatga     1317

<210> SEQ ID NO 77
<211> LENGTH: 69
<212> TYPE: DNA
<213> ORGANISM: Artificial Sequence
<220> FEATURE:
<223> OTHER INFORMATION: primer

<400> SEQUENCE: 77
ataaacaaac aaaccgcgga aaatggctaa ggaatacttc ccacaaatcc aaaagattaa      60
attcgaggg                                                             69

<210> SEQ ID NO 78
<211> LENGTH: 63
<212> TYPE: DNA
<213> ORGANISM: Artificial Sequence
<220> FEATURE:
<223> OTHER INFORMATION: primer

<400> SEQUENCE: 78
tgatgcggcc ctcgagttat tggtacatag caacaattgc ttcatacaat tcttgtttac      60
cac                                                                   63

<210> SEQ ID NO 79
<211> LENGTH: 69
<212> TYPE: DNA
<213> ORGANISM: Artificial Sequence
<220> FEATURE:
<223> OTHER INFORMATION: primer
```

<400> SEQUENCE: 79
ataaacaaac aaaccgcgga aaatgaagaa ttacttccca aatgtcccag aagtgaaata    60
tgaaggccc                                                            69

<210> SEQ ID NO 80
<211> LENGTH: 63
<212> TYPE: DNA
<213> ORGANISM: Artificial Sequence
<220> FEATURE:
<223> OTHER INFORMATION: primer

<400> SEQUENCE: 80
tgatgcggcc ctcgagtcat ctaaacaaga tgttattgac aatagtctcc aagacttctt    60
gtc                                                                  63

<210> SEQ ID NO 81
<211> LENGTH: 68
<212> TYPE: DNA
<213> ORGANISM: Artificial Sequence
<220> FEATURE:
<223> OTHER INFORMATION: primer

<400> SEQUENCE: 81
ataaacaaac aaaccgcgga aaatggcaac aaaagaattt tttccgggaa ttgaaaagat    60
taaatttg                                                             68

<210> SEQ ID NO 82
<211> LENGTH: 57
<212> TYPE: DNA
<213> ORGANISM: Artificial Sequence
<220> FEATURE:
<223> OTHER INFORMATION: primer

<400> SEQUENCE: 82
tgatgcggcc ctcgagttaa tacatattca gaattgcctc ataaagttct tgcttgc       57

<210> SEQ ID NO 83
<211> LENGTH: 1317
<212> TYPE: DNA
<213> ORGANISM: Lactococcus lactis

<400> SEQUENCE: 83
atggcctatt ttaacgacat tgcccctatc aagtatgaag gtaccaagac caagaatatg    60
ttcgctttta gacactacaa ccctgaagaa gttgtcgctg gtaaaactat ggaagaacaa   120
ttgcattttg cattagcctt ctggcacact attacaatgg atggttccga cccatttggt   180
ggtgctacaa tggaaagacc ttgggatttg aaggtggta gtgaattaga tagagcacat   240
agaagagtag acgcattttt cgaaatagcc gaaaagttgg gtgttaagta ctactgtttc   300
cacgatatcg acattgcccc aaccggtaac tccttgaagg aattctacgc aaacttagat   360
gaaatcactg accatttgtt agaaaagcaa aaggctaccg gtattaagtt gttgtggaac   420
actgcaaaca tgttctctaa ccctagatac atgaacggtg tatccaccag taatagagct   480
gaagttttcg catacggtgc tgcacaagtc aaaaagggtt tggaattgtc taaaaagttg   540
ggtggtgaaa actacgtttt ctggggtggt agagaaggtt acgaatcatt gttgaacaca   600
gatatgggtt tagaaatgga ccatatggct aagttttcc acttggccat agattatgct   660
aagtccatca atcatttgcc aattttcttg atcgaaccaa aacctaagga acctatgaca   720

```
caccaatacg attttgacag tgctaccgca ttggccttct tacaaaagta cgatttggac    780
aagtacttca agttgaattt ggaaactaac catgcctggt tggctggtca tacattcgaa    840
cacgaattga acacagctag aaccttcaac gcattgggtt caattgatgc taatcagggt    900
aactacttgt taggttggga tactgacgaa ttcccaacat tggttataga tatcactttg    960
gctatgcatc aaatcttgtt gaacggtggt ttgggtaaag gtggtataaa ctttgatgcc   1020
aaagtcagaa gaacatcttt caaggctgaa gatttgatct tagcacacat tgccggtatg   1080 gataccatg ctagagcatt aaaaggtgcc gctgcaataa tcgaggataa gttcttgtca    1140
gatatagtcg acgaaagata ttcttcatac agaaacacag aagtaggtca atctattgaa   1200
aacggtaccg caacttttga atcattggcc gctttcgcct tagaatacgg tgacgacatt   1260
gaattggaca gtaatcactt agaatacata aaatccgtct tgaacgacta cttggtt     1317
```

<210> SEQ ID NO 84
<211> LENGTH: 70
<212> TYPE: DNA
<213> ORGANISM: Artificial Sequence
<220> FEATURE:
<223> OTHER INFORMATION: primer

<400> SEQUENCE: 84

```
ataaacaaac aaaccgcgga aaatggccta ctttaacgac atcgcaccaa tcaaatacga    60
aggtactaag                                                           70
```

<210> SEQ ID NO 85
<211> LENGTH: 62
<212> TYPE: DNA
<213> ORGANISM: Artificial Sequence
<220> FEATURE:
<223> OTHER INFORMATION: primer

<400> SEQUENCE: 85

```
tgatgcggcc ctcgagttat accaagtagt cgttcaaaac actctttatg tattccaaat    60
gg                                                                   62
```

<210> SEQ ID NO 86
<211> LENGTH: 53
<212> TYPE: DNA
<213> ORGANISM: Artificial Sequence
<220> FEATURE:
<223> OTHER INFORMATION: primer

<400> SEQUENCE: 86

```
atcagaggtg gtggttttgt tacaggtggt accgctttcg atgcaaaaac cag           53
```

<210> SEQ ID NO 87
<211> LENGTH: 53
<212> TYPE: DNA
<213> ORGANISM: Artificial Sequence
<220> FEATURE:
<223> OTHER INFORMATION: primer

<400> SEQUENCE: 87

```
atcagaggtg gtggttttgt tacaggtggt acctgtttcg atgcaaaaac cag           53
```

<210> SEQ ID NO 88
<211> LENGTH: 53
<212> TYPE: DNA
<213> ORGANISM: Artificial Sequence
<220> FEATURE:
<223> OTHER INFORMATION: primer

<400> SEQUENCE: 88
atcagaggtg gtggttttgt tacaggtggt accactttcg atgcaaaaac cag        53

<210> SEQ ID NO 89
<211> LENGTH: 53
<212> TYPE: DNA
<213> ORGANISM: Artificial Sequence
<220> FEATURE:
<223> OTHER INFORMATION: primer

<400> SEQUENCE: 89
atcagaggtg gtggttttgt tacaggtggt accgttttcg atgcaaaaac cag        53

<210> SEQ ID NO 90
<211> LENGTH: 61
<212> TYPE: DNA
<213> ORGANISM: Artificial Sequence
<220> FEATURE:
<223> OTHER INFORMATION: primer

<400> SEQUENCE: 90
tgaaagctgg aggctttact aatggtggtc tagcttttga tgctaaggtt agaagaggca        60
g        61

<210> SEQ ID NO 91
<211> LENGTH: 61
<212> TYPE: DNA
<213> ORGANISM: Artificial Sequence
<220> FEATURE:
<223> OTHER INFORMATION: primer

<400> SEQUENCE: 91
tgaaagctgg aggctttact aatggtggtc tatgttttga tgctaaggtt agaagaggca        60
g        61

<210> SEQ ID NO 92
<211> LENGTH: 61
<212> TYPE: DNA
<213> ORGANISM: Artificial Sequence
<220> FEATURE:
<223> OTHER INFORMATION: primer

<400> SEQUENCE: 92
tgaaagctgg aggctttact aatggtggtc taacttttga tgctaaggtt agaagaggca        60
g        61

<210> SEQ ID NO 93
<211> LENGTH: 61
<212> TYPE: DNA
<213> ORGANISM: Artificial Sequence
<220> FEATURE:
<223> OTHER INFORMATION: primer

<400> SEQUENCE: 93
tgaaagctgg aggctttact aatggtggtc tagttttga tgctaaggtt agaagaggca        60
g        61

<210> SEQ ID NO 94
<211> LENGTH: 53
<212> TYPE: DNA
<213> ORGANISM: Artificial Sequence
<220> FEATURE:

<223> OTHER INFORMATION: primer

<400> SEQUENCE: 94
cggtaccggt ggtacggctt ttgatgctaa aacccgtcgt aattctactg atc        53

<210> SEQ ID NO 95
<211> LENGTH: 53
<212> TYPE: DNA
<213> ORGANISM: Artificial Sequence
<220> FEATURE:
<223> OTHER INFORMATION: primer

<400> SEQUENCE: 95
cggtaccggt ggtacgtgtt ttgatgctaa aacccgtcgt aattctactg atc        53

<210> SEQ ID NO 96
<211> LENGTH: 53
<212> TYPE: DNA
<213> ORGANISM: Artificial Sequence
<220> FEATURE:
<223> OTHER INFORMATION: primer

<400> SEQUENCE: 96
cggtaccggt ggtacgactt ttgatgctaa aacccgtcgt aattctactg atc        53

<210> SEQ ID NO 97
<211> LENGTH: 53
<212> TYPE: DNA
<213> ORGANISM: Artificial Sequence
<220> FEATURE:
<223> OTHER INFORMATION: primer

<400> SEQUENCE: 97
cggtaccggt ggtacggttt ttgatgctaa aacccgtcgt aattctactg atc        53

<210> SEQ ID NO 98
<211> LENGTH: 57
<212> TYPE: DNA
<213> ORGANISM: Artificial Sequence
<220> FEATURE:
<223> OTHER INFORMATION: primer

<400> SEQUENCE: 98
gaacggtggt ttgggtaaag gtggtatagc ttttgatgcc aaagtcagaa gaacatc    57

<210> SEQ ID NO 99
<211> LENGTH: 57
<212> TYPE: DNA
<213> ORGANISM: Artificial Sequence
<220> FEATURE:
<223> OTHER INFORMATION: primer

<400> SEQUENCE: 99
gaacggtggt ttgggtaaag gtggtatatg ttttgatgcc aaagtcagaa gaacatc    57

<210> SEQ ID NO 100
<211> LENGTH: 57
<212> TYPE: DNA
<213> ORGANISM: Artificial Sequence
<220> FEATURE:
<223> OTHER INFORMATION: primer

<400> SEQUENCE: 100
gaacggtggt ttgggtaaag gtggtataac ttttgatgcc aaagtcagaa gaacatc    57

```
<210> SEQ ID NO 101
<211> LENGTH: 57
<212> TYPE: DNA
<213> ORGANISM: Artificial Sequence
<220> FEATURE:
<223> OTHER INFORMATION: primer

<400> SEQUENCE: 101
gaacggtggt ttgggtaaag gtggtatagt ttttgatgcc aaagtcagaa gaacatc      57

<210> SEQ ID NO 102
<211> LENGTH: 18
<212> TYPE: PRT
<213> ORGANISM: Artificial Sequence
<220> FEATURE:
<223> OTHER INFORMATION: A consensus sequence in a Xylose ismerase
<220> FEATURE:
<221> NAME/KEY: MISC_FEATURE
<222> LOCATION: (3)..(3)
<223> OTHER INFORMATION: Xaa can be any naturally occurring amino acid,
      or preferably F or I or L
<220> FEATURE:
<221> NAME/KEY: MISC_FEATURE
<222> LOCATION: (4)..(4)
<223> OTHER INFORMATION: Xaa can be any naturally occurring amino acid,
      or preferably A or M
<220> FEATURE:
<221> NAME/KEY: MISC_FEATURE
<222> LOCATION: (5)..(5)
<223> OTHER INFORMATION: Xaa can be any naturally occurring amino acid,
      or preferably E or Q or S or T
<220> FEATURE:
<221> NAME/KEY: MISC_FEATURE
<222> LOCATION: (7)..(7)
<223> OTHER INFORMATION: Xaa can be any naturally occurring amino acid,
      or preferably L or M
<220> FEATURE:
<221> NAME/KEY: MISC_FEATURE
<222> LOCATION: (9)..(9)
<223> OTHER INFORMATION: Xaa can be any naturally occurring amino acid,
      or preferably I or V
<220> FEATURE:
<221> NAME/KEY: MISC_FEATURE
<222> LOCATION: (10)..(10)
<223> OTHER INFORMATION: Xaa can be any naturally occurring amino acid,
      or preferably E or K or P
<220> FEATURE:
<221> NAME/KEY: MISC_FEATURE
<222> LOCATION: (11)..(11)
<223> OTHER INFORMATION: Xaa can be any naturally occurring amino acid,
      or preferably F or Y
<220> FEATURE:
<221> NAME/KEY: MISC_FEATURE
<222> LOCATION: (12)..(12)
<223> OTHER INFORMATION: Xaa can be any naturally occurring amino acid,
      or preferably F or Y
<220> FEATURE:
<221> NAME/KEY: MISC_FEATURE
<222> LOCATION: (17)..(17)
<223> OTHER INFORMATION: Xaa can be any naturally occurring amino acid,
      or preferably A or I or V

<400> SEQUENCE: 102

Phe Glu Xaa Xaa Xaa Lys Xaa Gly Xaa Xaa Xaa Xaa Cys Phe His Asp
1               5                   10                  15

Xaa Asp

<210> SEQ ID NO 103
<211> LENGTH: 20
<212> TYPE: PRT
<213> ORGANISM: Artificial Sequence
<220> FEATURE:
<223> OTHER INFORMATION: A cosensus sequence in a Xylose isomerase
<220> FEATURE:
```

```
<221> NAME/KEY: MISC_FEATURE
<222> LOCATION: (2)..(2)
<223> OTHER INFORMATION: Xaa can be any naturally occurring amino acid,
      or preferably A or G
<220> FEATURE:
<221> NAME/KEY: MISC_FEATURE
<222> LOCATION: (3)..(3)
<223> OTHER INFORMATION: Xaa can be any naturally occurring amino acid,
      or preferably V or K or E
<220> FEATURE:
<221> NAME/KEY: MISC_FEATURE
<222> LOCATION: (4)..(4)
<223> OTHER INFORMATION: Xaa can be any naturally occurring amino acid,
      or preferably G or N
<220> FEATURE:
<221> NAME/KEY: MISC_FEATURE
<222> LOCATION: (15)..(15)
<223> OTHER INFORMATION: Xaa can be any naturally occurring amino acid,
      or preferably E or M
<220> FEATURE:
<221> NAME/KEY: MISC_FEATURE
<222> LOCATION: (16)..(16)
<223> OTHER INFORMATION: Xaa can be any naturally occurring amino acid,
      or preferably S or T

<400> SEQUENCE: 103

Gly Xaa Xaa Xaa Tyr Val Phe Trp Gly Gly Arg Glu Gly Tyr Xaa Xaa
1               5                   10                  15

Leu Leu Asn Thr
            20

<210> SEQ ID NO 104
<211> LENGTH: 23
<212> TYPE: PRT
<213> ORGANISM: Artificial Sequence
<220> FEATURE:
<223> OTHER INFORMATION: A consensus sequence in Xylose isomerase
<220> FEATURE:
<221> NAME/KEY: MISC_FEATURE
<222> LOCATION: (2)..(2)
<223> OTHER INFORMATION: Xaa can be any naturally occurring amino acid,
      or preferably D or E
<220> FEATURE:
<221> NAME/KEY: MISC_FEATURE
<222> LOCATION: (4)..(4)
<223> OTHER INFORMATION: Xaa can be any naturally occurring amino acid,
      or preferably D or Y
<220> FEATURE:
<221> NAME/KEY: MISC_FEATURE
<222> LOCATION: (7)..(7)
<223> OTHER INFORMATION: Xaa can be any naturally occurring amino acid,
      or preferably L or M or V
<220> FEATURE:
<221> NAME/KEY: MISC_FEATURE
<222> LOCATION: (9)..(9)
<223> OTHER INFORMATION: Xaa can be any naturally occurring amino acid,
      or preferably I or L
<220> FEATURE:
<221> NAME/KEY: MISC_FEATURE
<222> LOCATION: (11)..(11)
<223> OTHER INFORMATION: Xaa can be any naturally occurring amino acid,
      or preferably A or T or V
<220> FEATURE:
<221> NAME/KEY: MISC_FEATURE
<222> LOCATION: (15)..(15)
<223> OTHER INFORMATION: Xaa can be any naturally occurring amino acid,
      or preferably T or W
<220> FEATURE:
<221> NAME/KEY: MISC_FEATURE
<222> LOCATION: (22)..(22)
<223> OTHER INFORMATION: Xaa can be any naturally occurring amino acid,
      or preferably Q or E

<400> SEQUENCE: 104

Leu Xaa Lys Xaa Phe Lys Xaa Asn Xaa Glu Xaa Asn His Ala Xaa Leu
```

```
1               5                   10                  15
Ala Gly His Thr Phe Xaa His
            20
```

```
<210> SEQ ID NO 105
<211> LENGTH: 21
<212> TYPE: PRT
<213> ORGANISM: Artificial Sequence
<220> FEATURE:
<223> OTHER INFORMATION: A consensus sequence in a Xylose isomerase
<220> FEATURE:
<221> NAME/KEY: MISC_FEATURE
<222> LOCATION: (1)..(1)
<223> OTHER INFORMATION: Xaa can be any naturally occurring amino acid,
      or preferably F or L
<220> FEATURE:
<221> NAME/KEY: MISC_FEATURE
<222> LOCATION: (4)..(4)
<223> OTHER INFORMATION: Xaa can be any naturally occurring amino acid,
      or preferably I or V
<220> FEATURE:
<221> NAME/KEY: MISC_FEATURE
<222> LOCATION: (8)..(8)
<223> OTHER INFORMATION: Xaa can be any naturally occurring amino acid,
      or preferably Q or R or T
<220> FEATURE:
<221> NAME/KEY: MISC_FEATURE
<222> LOCATION: (10)..(10)
<223> OTHER INFORMATION: Xaa can be any naturally occurring amino acid,
      or preferably D or N
<220> FEATURE:
<221> NAME/KEY: MISC_FEATURE
<222> LOCATION: (11)..(11)
<223> OTHER INFORMATION: Xaa can be any naturally occurring amino acid,
      or preferably P or Y
<220> FEATURE:
<221> NAME/KEY: MISC_FEATURE
<222> LOCATION: (12)..(12)
<223> OTHER INFORMATION: Xaa can be any naturally occurring amino acid,
      or preferably L or N or Q
<220> FEATURE:
<221> NAME/KEY: MISC_FEATURE
<222> LOCATION: (13)..(13)
<223> OTHER INFORMATION: Xaa can be any naturally occurring amino acid,
      or preferably L or N
<220> FEATURE:
<221> NAME/KEY: MISC_FEATURE
<222> LOCATION: (19)..(19)
<223> OTHER INFORMATION: Xaa can be any naturally occurring amino acid,
      or preferably E or Q

<400> SEQUENCE: 105

Xaa Gly Ser Xaa Asp Ala Asn Xaa Gly Xaa Xaa Xaa Xaa Gly Trp Asp
1               5                   10                  15

Thr Asp Xaa Phe Pro
            20
```

PROTEIN HAVING XYLOSE ISOMERASE ACTIVITY AND USE OF SAME

CROSS REFERENCE TO RELATED APPLICATIONS

This is a Division of application Ser. No. 14/780,987 filed Sep. 28, 2015, which in turn is a national stage entry of PCT/JP2014/001849 filed Mar. 28, 2014, which claims priority to JP 2013-070584 filed Mar. 28, 2013, and JP 2014-024878 filed Feb. 12, 2014. The disclosure of the prior applications is hereby incorporated by reference herein in its entirety.

The present application relates to a protein having novel xylose isomerase activity, and to a technique for producing a useful substance in use of this protein, with xylose being a carbon source.

TECHNICAL FIELD

Background Art

Yeast, *Saccharomyces cerevisiae*, which is a fermentation microorganism for a production process of cellulose ethanol, is not able to utilize xylose included in vegetable biomass in a large amount. Therefore, researches for imparting xylose utilization ability to *Saccharomyces cerevisiae* are in progress. To this end, introduction of 2 types of pathways to the yeast is investigated. One is a pathway (XR-XDH pathway) using a xylose reductase (XR) and a xylitol dehydrogenase (XDH). However, there is a drawback in the pathway that intermediate metabolites accumulate and the ethanol yield decreases. Meanwhile, in the case of a pathway (XI pathway) using a xylose isomerase (XI), there is no such a drawback, but another drawback arises that the consumption rate of xylose is slow in comparison to the XR-XDH pathway. Therefore, various investigations are under way for a high performance XI.

Improvement of a XI originated from *Piromyces* sp. E2, which was reported as the first XI being able to function in yeast, has been carried out (Patent Literature 1, Non Patent Literature 1). Further, improvement of a XI originated from *Ruminococcus flavefaciens* has been also carried out (Patent Literature 2). Further, improvement of a XI originated from *Lactococcus lactis* has been also carried out (Patent Literature 3). Furthermore, a XI originated from an enteric protist of *Reticulitermes speratus* having higher xylose consuming ability of yeast compared to a heretofore known XI has been reported (Patent Literature 4).

CITATION LIST

Patent Literature

[Patent Literature 1] Japanese Patent Application Publication No. 2008-79564
[Patent Literature 2] WO 2011/150313
[Patent Literature 3] WO 2010/070549
[Patent Literature 4] Japanese Patent Application Publication No. 2011-147445

Non Patent Literature

[Non Patent Literature 1] Lee S, Jellison T, Alper H S. Appl Environ Microbiol, 2012; 78 (16): 5708-16

SUMMARY OF INVENTION

However, the xylose consumption rate of an XI in Patent Literature 1 and Non Patent Literature 1 remained too low. Further, with respect to an XI in Patent Literature 1 the activity in yeast was not disclosed. Meanwhile, with respect to an XI in Patent Literature 2, although improvement of the growth rate of a transgenic yeast in a xylose culture medium has been recognized, the fermentation performance is not clear. Further, with respect to a XI in Patent Literature 3 the growth characteristic and fermentation performance in a xylose culture medium are not clear. Further, with respect to a XI described in Patent Literature 4, although XI ability in yeast has been improved, further improvement thereof is sought after.

Under such circumstances, an XI favorable for improving xylose consuming capacity and improving fermenting capacity in yeast has been still sought after.

According to the present description, a protein with XI activity useful for improving the xylose fermentation ability of yeast and a use of the same are provided.

Solution to Technical Problem

The inventors focused on an XI originated from an enteric protist in *Reticulitermes speratus* (hereinafter referred to as "RsXI") and found that the xylose fermenting capacity of yeast could be improved by modification of the XI by introduction of a point mutation substituting another amino acid. Further, it was found that the amino acid substitution mutation introduced into the XI was also effective in another XI having a similar amino acid sequence. Based on the findings, the following means are disclosed hereunder.

[1] A protein that has xylose isomerase activity and has an amino acid sequence including, when aligned with an amino acid sequence expressed by SEQ ID NO:1, the following 1st to 6th motifs from the N-terminus of the protein in the order described, and having, in place of asparagine (N) in an amino acid sequence of the 6th motif, another amino acid:

1st motif: FXXXXKXXXXXXXHDXD (SEQ ID NO:2)
  wherein X represents a naturally occurring amino acid,
2nd motif: XXXXXXXWGGREGYXXLXNT (SEQ ID NO:3)
  wherein X represents a naturally occurring amino acid,
3rd motif: XXXXXXXXEPKPXEPXXHQYDXD (SEQ ID NO:4)
  wherein X represents a naturally occurring amino acid,
4th motif: LXXXXXXNXEXNHXXLXXHXXXH (SEQ ID NO:5)
  wherein X represents a naturally occurring amino acid,
5th motif: XGSXDXNXGXXXXGWDXDXXP (SEQ ID NO:6)
  wherein X represents a naturally occurring amino acid, and
6th motif: GGXNFDXKXRR (SEQ ID NO:7)
  wherein X represents a naturally occurring amino acid.

[2] The protein according to [1], wherein:
the 1st motif is expressed by FXXXXKXGXXXXXFHDXD (SEQ ID NO:8),
the 2nd motif is expressed by XXXXXVFWGGREGYXXLLNT (SEQ ID NO:9),
the 3rd motif is expressed by XXXXXFXIEPKPXEPXXHQYDXD (SEQ ID NO:10),
the 4th motif is expressed by LXXXFKXNXEXNHXXLAGHXXXH (SEQ ID NO:11),
the 5th motif is expressed by XGSXDXNXGXXXXGWDTDXFP (SEQ ID NO:12), and
the 6th motif is expressed by GGXNFDXKXRR (SEQ ID NO:13).

[3] The protein according to claim [1] or [2], wherein:
the 1st motif is expressed by FEXXXKXGXXXXCFHDXD (SEQ ID NO:102), (wherein position 3 is F or I or L; position 4 is A or M; position 5 is E or Q or S or T; position 7 is L or M; position 9 is I or V; position 10 is E or K or P; position 11 is F or Y; position 12 is F or Y; and position 17 is A or I or V), the 2nd motif is expressed by GXXXYVFWGGREGYXXLLNT (SEQ ID NO:103), (wherein, position 2 is A or G; position 3 is V or K or E; position 4 is G or N; position 15 is E or M; and position 16 is S or T), the 3rd motif is expressed by XXXXXFXIEPKPXEPXXHQYDXD (SEQ ID NO:10), (wherein, position 1 is G or N; position 2 is F or H; position 3 is K or D or L; position 4 is G or P; position 5 is D or T or I; position 7 is L or Y; position 13 is K or M; position 16 is M or T; position 17 is K or T; and position 22 is F or V), the 4th motif is expressed by LXKXFKXNXEXNHAXLAGHTFXH (SEQ ID NO:104), (wherein, position 2 is D or E; position 4 is D or Y; position 7 is L or M or V; position 9 is I or L; position 11 is A or T or V; position 15 is T or W; and position 22 is Q or E), the 5th motif is expressed by XGSXDANXGXXXXGWDTDXFP (SEQ ID NO:105), (wherein, position 1 is F or L; position 4 is I or V; position 8 is Q or R or T; position 10 is D or N; position 11 is P or Y; position 12 is L or N or Q; position 13 is L or N, and position 19 is E or Q), and the 6th motif is expressed by GGXNFDXKXRR (SEQ ID NO:13), (wherein, position 3 is I or L or T; position 7 is A or S; and position 9 is T or V).

[4] The protein according to any one of [1] to [3], comprising an amino acid selected from the group consisting of cysteine, threonine, valine, and alanine in place of asparagine (N) in the 6th motif

[5] The protein according to any one of [1] to [4], comprising threonine or cysteine in place of the asparagine.

[6] The protein according to any one of [1] to [5], wherein
the 1st motif is composed of an amino acid sequence having an identity of 65% or more with the amino acid sequence expressed by SEQ ID NO:24, the 2nd motif is composed of an amino acid sequence having an identity of 75% or more with the amino acid sequence expressed by SEQ ID NO:25, the 3rd motif is composed of an amino acid sequence having an identity of 65% or more with the amino acid sequence expressed by SEQ ID NO:26, the 4th motif is composed of an amino acid sequence having an identity of 70% or more with the amino acid sequence expressed by SEQ ID NO:27, the 5th motif is composed of an amino acid sequence having an identity of 70% or more with the amino acid sequence expressed by SEQ ID NO:28, and the 6th motif is composed of an amino acid sequence having an identity of 70% or more with the amino acid sequence expressed by SEQ ID NO:29.

[7] A DNA coding for the protein according to any one of [1] to [6].

[8] A transformation vector for a eukaryotic cell, containing the DNA according to [7].

[9] A eukaryotic cell retaining the DNA according to [7].

[10] The eukaryotic cell according to [9], which is yeast.

[11] The eukaryotic cell according to [10], wherein the yeast belongs to any one selected from the group consisting of *Saccharomyces, Kluyveromyces, Candida, Pichia, Schizosaccharomyces, Hancenula, Klocckera, Schwanniomyces, Yarrowia*, and *Issatchenkia*.

[12] The eukaryotic cell according to any one of [9] to [11], which produces secretory cellulase.

[13] The eukaryotic cell according to any one of [9] to [12], having an exogenous or endogenous gene that produces any one selected from the group consisting of ethanol, lactic acid, acetic acid, 1,3-propanediol, propanol, butanol, succinic acid, ethylene, glycerol, farnesol, geranylgeraniol and squalene.

[14] A method for generating a eukaryotic cell with imparted or improved xylose utilization ability, comprising a step of introducing the DNA according to [7] into a eukaryotic cell for transformation.

[15] A method for producing a useful substance, comprising a step of culturing the eukaryotic cell according to any one of [9] to [13] in the presence of xylose.

[16] The production method according to [15], wherein the useful substance is any one selected from the group consisting of ethanol, lactic acid, acetic acid, 1,3-propane diol, propanol, butanol, succinic acid, ethylene, glycerol, farnesol, geranylgeraniol and squalene.

BRIEF DESCRIPTION OF DRAWINGS

FIG. 1 is a chart showing identities of amino acid sequences of XIs having activity in yeast with that of RsXI.

FIG. 3 is a chart showing amino acid sequence alignments of RsXI (SEQ ID NO: 1) and other XIs (SEQ ID NOS: 14 to 23) having activity in yeast.

FIG. 4 is a chart showing identities with respect to each motif of XIs having activity in yeast.

FIG. 8 is a chart showing fermentation test results (xylose consumption in 72 hours) utilizing xylose as a carbon source.

DESCRIPTION OF EMBODIMENTS

The disclosure hereunder relates to a novel XI, which has certain relationship with RsXI, namely a xylose isomerase originated from an enteric protist in *Reticulitermes speratus* and is useful for enhancing xylose utilization ability of an eukaryotic cell such as yeast. The inventors have discovered that a substitution mutation effective in enhancing xylose utilization ability of yeast found for RsXI is also effective in enhancing xylose utilization ability of a eukaryotic cell with respect to another XI. Another XI having motifs common to RsXI is considered to be a XI having a function similar to RsXI. In the event that a modified XI, in which a substitution mutation is introduced to asparagine in a motif, is expressed in a eukaryotic cell, xylose isomerase activity can be exhibited and the xylose utilization ability of the host eukaryotic cell can be improved. The disclosure of the current description will be described below in detail referring appropriately to the drawings.

(Protein Having Xylose Isomerase Activity)

The present protein, when aligned with an amino acid sequence expressed by SEQ ID NO:1 of RsXI, may include 1, or 2 or more of the 1st to 6th motifs (SEQ ID NOs:2 to 7) described below. The 1st to 6th motifs may be contained in the present protein from the N-terminus side of the amino acid sequence in the order described.

All of the motifs are found in RsXI, and the inventors found the same also in other XIs by a motif analysis according to multiple alignments with such other XIs.

The present protein contains preferably at least the 6th motif out of the 1st to 6th motifs. The protein contains preferably also the 4th motif, more preferably also the 5th motif, still more preferably also the 3rd motif, even more preferably also the 1st motif, and still even more preferably also the 2nd motif.

In the motif analysis, the amino acid sequence of RsXI was searched by Protein BLAST (Database: Non-redundant protein sequence, Algorism parameter: default setting). With respect to other top 500 analogous amino acid sequences and the amino acid sequence of RsXI, alignment analysis was performed. Form the results of the alignment analysis, consensus sequences of 6 characteristic domains were defined as motif sequences.

Examples of such other XIs hit as analogous amino acid sequences include 10 XIs having activity in yeast shown in FIG. 1. The identities of the XIs with the amino acid sequence expressed by SEQ ID NO:1 of RsXI are 46% to 63% and not particularly high, however the XIs have in common the 1st to 6th motifs and have high identities with the respective motifs in SEQ ID NO:1. Such other XIs can be found in a publicly known database using the amino acid sequence of RsXI expressed by SEQ ID NO:1.

Figure 2:
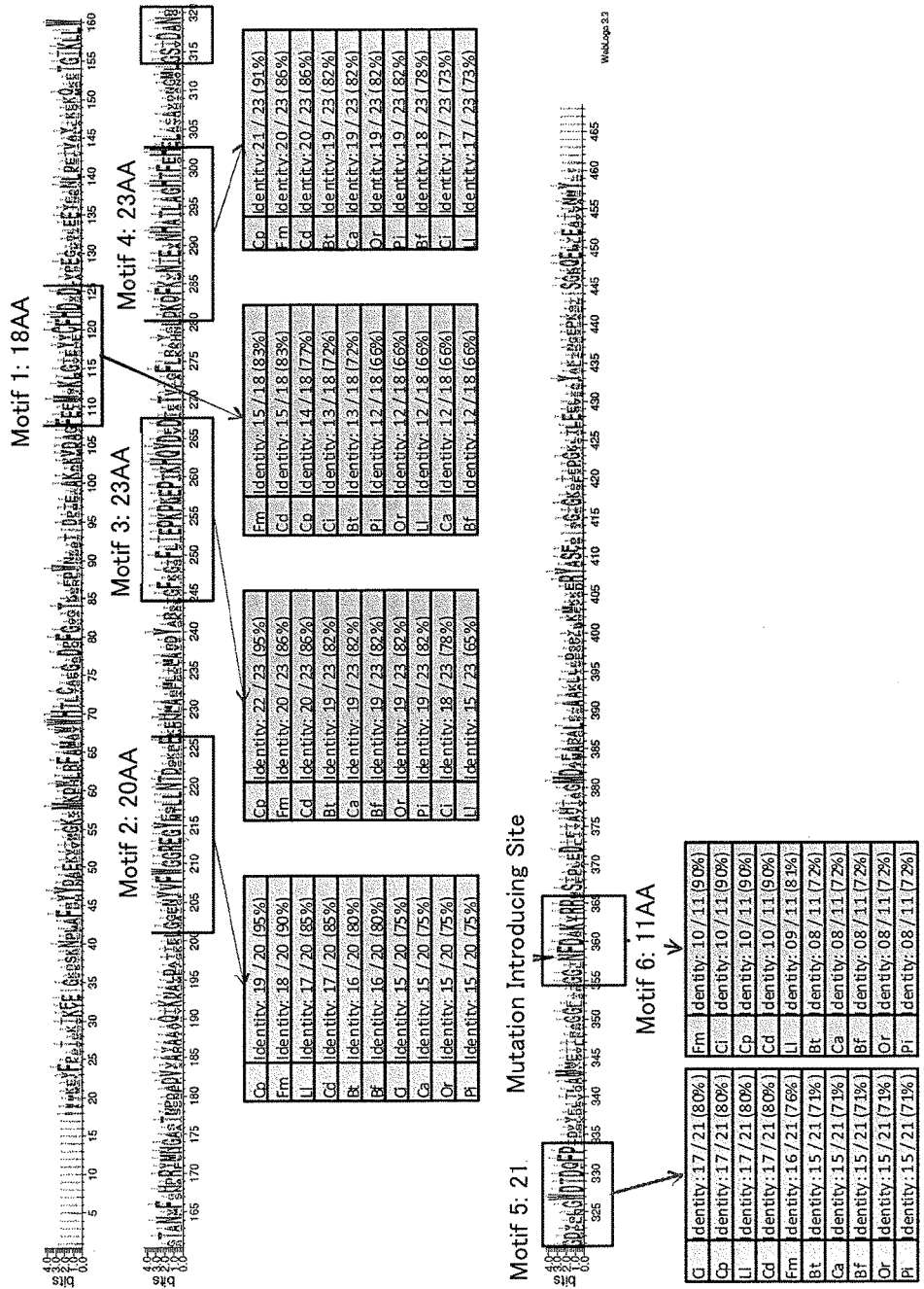
FIG. 2 is a chart showing sequence logo analysis results and motif analysis results of RsXI and other XIs having activity in yeast.
Figure 3:
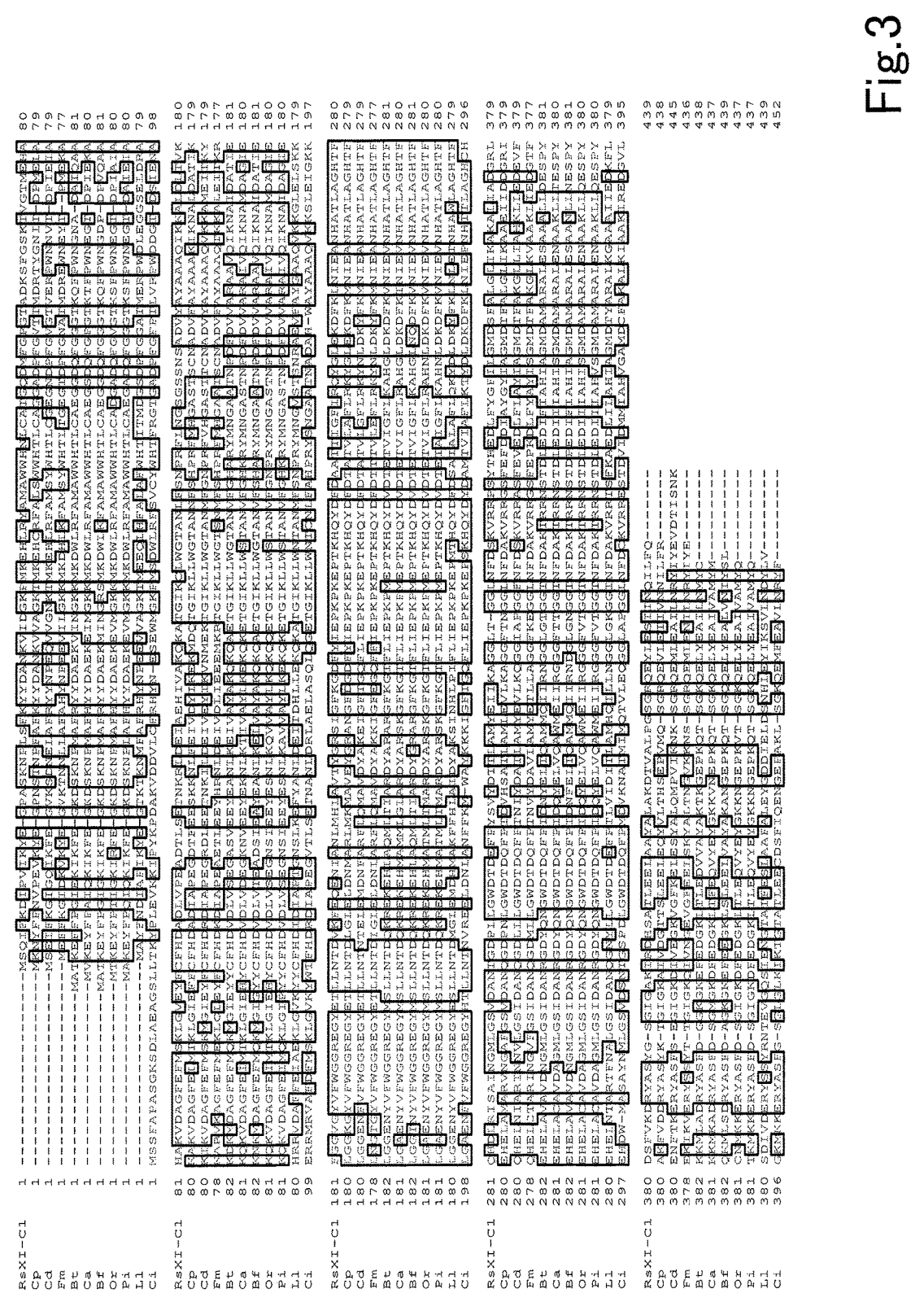

In FIG. 2 are shown the results of a sequence logo analysis and a motif analysis by multiple alignments of the amino acid sequence expressed by SEQ ID NO:1 and the amino acid sequences of the 10 XIs (SEQ ID NOs:14 to 23) shown in FIG. 1, as well as the identities with respect to each motif. The identities are described in FIG. 2 in descending order of identity percentage. FIG. 3 shows multiple alignment analysis results of RsXI and other 10 XIs. FIG. 4 shows identities with respect to each motif of other XIs having activity in yeast.

Those skilled in the art can perform multiple alignment by using various publicly known database such as Protein BLAST, which is an aforedescribed publicly known database. There is no particular restriction on a technique to be used for multiple alignment or a technique for obtaining a consensus sequence, and various techniques, such as ClustalW; HMMER (hidden Markov model); MultiAlin; and mkdom/xdom, can be applied. Further, from the multiple alignment highly conservative amino acids can be extracted. Such a technique is also well known to those skilled in the art. For example, using Weblogo3.3 a logo of highly conservative amino acids can be created. In the sequence logo analysis shown in FIG. 2, a higher conservation amino acid is represented larger. Further, from such a sequence logo analysis, a motif analysis to specify a high conservation region (motif) is possible.

"Identity" and "similarity" herein, as have been known well to those skilled in the art, are relationships between two or more proteins or two more polynucleotide determined by comparing the sequences. "Identity" in the art, also means the degree of sequence invariance between protein or polynucleotide sequences, as determined by the alignment between the protein or polynucleotide sequences, as the case maybe the alignment between strings of such sequences. In addition, "similarity" means the degree of sequence relatedness between protein or polynucleotide sequences, as determined by the alignment between the protein or polynucleotide sequences, as the case maybe the alignment between strings of such sequences. More specifically, "Similarity" is determined by the sequence identity or conservativeness (replacement which can maintain the physical and chemical properties of a particular amino acid or amino acid sequence). "Similarity" is referred to as Similarity in the search result BLAST sequence homology to be described later. Preferred methods of determining "identity" or "similarity" are designed to give the longest alignment between the sequences to be tested. Method for determining identity and similarity, are codified in publicly available computer programs. "Identity" and "similarity" can be determined by, for example, using the BLAST (Basic Local Alignment Search Tool) program by Altschul et. al., (for example, Altschul S F, Gish W, Miller W, Myers E W, Lipman D J, J. Mol Biol, 215: P 403-410 (1990), Altschyl S F, Madden T L, Schaffer A A, Zhang J, Miller W, Lipman D J, 25 Nucleic Acids Res. 25: p 3389-3402 (1997)). Where software such as BLAST used, it is but not limited to, preferable to use default values.

(The 1st Motif)

The 1st motif is expressed by FXXXXKXXXXXXXX-HDXD (SEQ ID NO:2). The 1st motif is composed of 18 amino acids and corresponds to position 88 to position 105 of the amino acid sequence expressed by SEQ ID NO:1. It is presumed that in the motif the amino acid residues at position 15 (H) and position 18 (D) are residues constituting an active site (Hu, H., H. Liu, and Y. Shi., 1997. The reaction pathway of the isomerization of D-xylose catalyzed by the enzyme D-xylose isomerase: a theoretical study, Proteins 27: 545-55.).

The respective X's (naturally occurring amino acids) in the 1st motif expressed by SEQ ID NO:2 are preferably the following amino acids:
position 2: D or E
position 3: F or I or L or M
position 4: A or C or F or I or L or M or Y
position 5: D or E or H or N or Q or S or T
position 7: L or M
position 8: D or G or N or S
position 9: A or I or L or T or V
position 10: D or E or G or K or P
position 11: F or H or Y
position 12: F or L or W or Y
position 13: A or C or S or T
position 14: F or W, and
position 17: A or I or K or R or T or V.

The 1st motif is preferably expressed by FXXXXKXGXXXXXFHDXD (SEQ ID NO:8). Meanwhile, the 1st motif to the 6th motif expressed by SEQ ID NOs:8 to 13 were defined as domains that agree with the top 500 motif sequences obtained by the alignment analysis by performing another alignment analysis similar to the above, limitedly with the amino acid sequence of RsXI (SEQ ID NO:1) and 10 amino acid sequences (SEQ ID NO:14 to 23) of XIs, which activity in yeast was confirmed, shown in FIG. 1.

The respective X's (naturally occurring amino acids) in the 1st motif expressed by SEQ ID NO:8 are preferably the following amino acids:
position 2: D or E
position 3: F or I or L
position 4: A or M
position 5: E or Q or S or T
position 7: L or M
position 9: I or V
position 10: E or G or K or P
position 11: F or H or Y
position 12: F or W or Y
position 13: C or T, and
position 17: A or I or K or R or V.

The 1st motif is more preferably expressed by FEXXXKXGXXXXCFHDXD (SEQ ID NO:102). The respective X's (naturally occurring amino acids) in the 1st motif expressed by SEQ ID NO:102 are preferably the following amino acids. This 1st motif is based on the results of an alignment analysis performed with the amino acid sequence of RsXI (SEQ ID NO:1) and amino acid sequences of XIs originated from *Piromyces* sp. E2, *Clostridium phytofermentans*, *Bacteroides thetaiotaomicron*, and *Lactococcus lactis* respectively.
position 3: F or I or L
position 4: A or M
position 5: E or Q or S or T
position 7: L or M
position 9: I or V
position 10: E or K or P
position 11: F or Y
position 12: F or Y, and
position 17: A or I or V The 1st motif is preferably composed of an amino acid sequence having an identity of 60% or more with the amino acid corresponding to the 1st motif of RsXI expressed by FEFMSKLGVEYFCFHDAD (SEQ ID NO:24). The 1st motif is more preferably composed of an amino acid sequence having an identity of 65% or more with the amino acid sequence expressed by SEQ ID NO:24, still more preferably 70% or more, and even more preferably 75% or more. The identity may be 80% or more, may be 85% or more, may be 90% or more, and further may be 95% or more.

As obvious from FIG. 2, with respect to the 1st motif, 10 XIs having activity in yeast shown in FIG. 1 have preferably an identity of 66% or more in terms of amino acid sequence identity, preferably 70% or more, more preferably 75% or more, and further preferably 80% or more.

(The 2nd Motif)

The 2nd motif is expressed by XXXXXXXWGGREGYXXLXNT (SEQ ID NO:3). The 2nd motif is composed of 20 amino acids and corresponds to position 182 to 201 of the amino acid sequence of RsXI expressed by SEQ ID NO:1.

The respective X's (naturally occurring amino acids) in the 2nd motif expressed by SEQ ID NO:2 are preferably the following amino acids:
position 1: D or G or K or N
position 2: A or G or S
position 3: A or E or K or Q or S or T or V
position 4: G or N
position 5: F or Y
6position: V or T
position 7: F or L
position 15: A or D or E or H or M
position 16: C or N or S or T, and
position 18: H or L or W.

The 2nd motif is preferably expressed by XXXXXXVFWGGREGYXXLLNT (SEQ ID NO:9). The respective X's (naturally occurring amino acids) in the 2nd motif expressed by SEQ ID NO:9 are preferably the following amino acids:
position 1: G or N
position 2: A or G
position 3: V or K or E or T
position 4: G or N
position 5: F or Y
position 15: E or M or H, and
position 16: S or T.

The 2nd motif is more preferably expressed by GXXXYVFWGGREGYXXLLNT (SEQ ID NO:103). The respective X's (naturally occurring amino acids) in the 2nd motif expressed by SEQ ID NO:103 are preferably the following amino acids. This 2nd motif is based on the results of an alignment analysis performed with the amino acid sequence of RsXI (SEQ ID NO:1) and amino acid sequences of XIs originated from *Piromyces* sp. E2, *Clostridium phytofermentans*, *Bacteroides thetaiotaomicron*, and *Lactococcus lactis* respectively.
position 2: A or G
position 3: V or K or E
position 4: G or N
position 15: E or M, and
position 16: S or T The 2nd motif is preferably composed of an amino acid sequence having an identity of 60% or more with the amino acid corresponding to the 2nd motif of RsXI expressed by GGVGYVFWGGREGYETLLNT (SEQ ID NO:25). The 2nd motif is more preferably composed of an amino acid sequence having an identity of 65% or more with the amino acid sequence expressed by SEQ ID NO:25, still more preferably 70% or more, and even more preferably 75% or more. The identity may be 80% or more, may be 85% or more, may be 90% or more, and further may be 95% or more.

As obvious from FIG. 2, with respect to the 2nd motif, 10 XIs having activity in yeast shown in FIG. 1 have preferably an identity of amino acid sequence of 75% or more, preferably 80% or more, more preferably 85% or more, still more preferably 90% or more, and even more preferably 95% or more.

(The 3rd Motif)

The 3rd motif is expressed by XXXXXXXXEPKPXEPXXHQYDXD (SEQ ID NO:4). The 3rd motif is composed of 23 amino acids and corresponds to position 225 to position 247 of the amino acid sequence of RsXI expressed by SEQ ID NO:1. It is presumed that in the motif the amino acid residues at position 9 (E) and position 11 (K) are residues constituting an active site.

The respective X's (naturally occurring amino acids) in the 3rd motif expressed by SEQ ID NO:4 are preferably the following amino acids:
position 1: G or N
position 2: F or H or Y
position 3: D or E or K or L or N or Q or R or T
position 4: G or P
position 5: A or D or I or N or Q or T
position 6: F or L or M
position 7: F or L or Y
position 8: I or L
position 13: K or M or Q
position 16: M or S or T
position 17: K or S or T, and
position 22: F or T or V or Y.

The 3rd motif is preferably expressed by XXXXXFX-IEPKPXEPXXHQYDXD (SEQ ID NO:10). The respective X's (naturally occurring amino acids) in the 3rd motif expressed by SEQ ID NO:10 are preferably the following amino acids:
position 1: G or N
position 2: F or H
position 3: K or D or T or E or L
position 4: G or P
position 5: D or Q or T or I
position 7: F or L or Y
position 13: K or M
position 16: M or S or T
position 17: K or T, and
position 22: F or V or Y.

With respect to the 3rd motif in the amino acid sequence expressed by SEQ ID NO:10, based on the results of an alignment analysis performed with the amino acid sequence of RsXI (SEQ ID NO:1) and amino acid sequences of XIs originated from *Piromyces* sp. E2, *Clostridium phytofermentans*, *Bacteroides thetaiotaomicron*, and *Lactococcus lactis* respectively, the following amino acids are preferable:
position 1: G or N
position 2: F or H
position 3: K or D or L
position 4: G or P
position 5: D or T or I
position 7: L or Y
position 13: K or M
position 16: M or T
position 17: K or T, and
position 22: F or V.

The 3rd motif is preferably composed of an amino acid sequence having an identity of 60% or more with the amino acid corresponding to the 3rd motif of RsXI expressed by GFKGDFYIEPKPKEPTKHQYDFD (SEQ ID NO:26). The 3rd motif is more preferably composed of an amino acid sequence having an identity of 65% or more with the amino acid sequence expressed by SEQ ID NO:26, still more preferably 70% or more, and even more preferably 75% or more. The identity may be 80% or more, may be 85% or more, may be 90% or more, and further may be 95% or more.

As obvious from FIG. 2, with respect to the 3rd motif, 10 XIs having activity in yeast shown in FIG. 1 have preferably an identity of amino acid sequence of 65% or more, preferably 70% or more, more preferably 75% or more, still more preferably 80% or more, even more preferably 85% or more, still even more preferably 90% or more, and yet even more preferably 95% or more.

(The 4th Motif)

The 4th motif is expressed by LXXXXXXXNXEXNHXX-LXXHXXXH (SEQ ID NO:5). The 4th motif is composed of 23 amino acids and corresponds to position 260 to position 282 of the amino acid sequence of RsXI expressed by SEQ ID NO:1. It is presumed that in the motif the amino acid residues at position 10 (E) and position 13 (K) are residues constituting an active site.

The respective X's (naturally occurring amino acids) in the 4th motif expressed by SEQ ID NO:5 are preferably the following amino acids:
position 2: D or E or K or L or N or Q
position 3: D or E or G or K or N or P or Q
position 4: D or E or H or Y
position 5: F or I or V
position 6: K or R
position 7: F or I or L or M or V
position 9: I or L
position 11: A or G or P or T or V
position 14: A or T
position 15: N or T or W
position 17: A or S
position 18: F or G or Q
position 20: C or D or S or T
position 21: F or H or M or Y, and
position 22: D or E or H or M or Q.

The 4th motif is preferably expressed by LXXXFKXNX-EXNHXXLAGHXXXH (SEQ ID NO:11). The respective X's (naturally occurring amino acids) in the 4th motif expressed by SEQ ID NO:11 are preferably the following amino acids:
position 2: D or E or N
position 3: K or Q
position 4: D or Y
position 7: I or L or M or V
position 9: I or L
position 11: A or P or T or V
position 14: A or T
position 15: T or W
position 20: C or T
position 21: F or H, and
position 22: Q or E.

The 4th motif is more preferably expressed by LXKXFKXNXEXNHAXLAGHTFXH (SEQ ID NO:104). The respective X's (naturally occurring amino acids) in the 4th motif expressed by SEQ ID NO:104 are preferably the following amino acids. This 4th motif is based on the results of an alignment analysis performed with the amino acid sequence of RsXI (SEQ ID NO:1) and amino acid sequences of XIs originated from *Piromyces* sp. E2, *Clostridium phytofermentans*, *Bacteroides thetaiotaomicron*, and *Lactococcus lactis* respectively.
position 2: D or E
position 4: D or Y
position 7: L or M or V
position 9: I or L
position 11: A or T or V
position 15: T or W, and
position 22: Q or E The 4th motif is preferably composed of an amino acid sequence having an identity of 60% or more with the amino acid corresponding to the 4th motif of RsXI expressed by LEKDFKLNIEANHATLAGHTFQH (SEQ ID NO:27). The 4th motif is more preferably composed of an amino acid sequence having an identity of 65% or more with the amino acid sequence expressed by SEQ ID NO:27, still more preferably 70% or more, and even more preferably 75% or more. The identity may be 80% or more, may be 85% or more, may be 90% or more, and further may be 95% or more.

As obvious from FIG. 2, with respect to the 4th motif, 10 XIs having activity in yeast shown in FIG. 1 have preferably an identity of amino acid sequence of 73% or more, preferably 75% or more, more preferably 80% or more, still more preferably 85% or more, and even more preferably 90% or more.

(The 5th Motif)

The 5th motif is expressed by XGSXDXNXGXXXXG-WDXDXXP (SEQ ID NO:6). The 5th motif is composed of 21 amino acids and corresponds to position 293 to position 303 of the amino acid sequence of RsXI expressed by SEQ ID NO:1. It is presumed that in the motif the amino acid residues at position 5 (D), position 16 (D) and position 18 (D) are residues constituting an active site.

The respective X's (naturally occurring amino acids) in the 5th motif expressed by SEQ ID NO:6 are preferably the following amino acids:
position 1: F or L
position 4: I or L or V
position 6: A or S
position 8: M or Q or R or T
position 10: D or H or N or S
position 11: A or K or L or M or P or T or V or Y
position 12: L or N or Q or D
position 13: I or L or N
position 17: I or T
position 19: E or Q, and
position 20: F or Y.

The 5th motif is preferably expressed by XGSXDX-NXGXXXXGWDTDXFP (SEQ ID NO:12). The respective X's (naturally occurring amino acids) in the 5th motif expressed by SEQ ID NO:12 are preferably the following amino acids:
position 1: F or L
position 4: I or V
position 6: A or S
position 8: Q or R or T
position 10: D or N or S
position 11: L or M or P or Y
position 12: D or L or N or Q
position 13: L or N, and
position 19: E or Q.

The 5th motif is more preferably expressed by XGSX-DANXGXXXXGWDTDXFP (SEQ ID NO:105). The respective X's (naturally occurring amino acids) in the 5th motif expressed by SEQ ID NO:105 are preferably the following amino acids. This 5th motif is based on the results of an alignment analysis performed with the amino acid sequence of RsXI (SEQ ID NO:1) and amino acid sequences of XIs originated from *Piromyces* sp. E2, *Clostridium phytofermentans, Bacteroides thetaiotaomicron*, and *Lactococcus lactis* respectively.
position 1: F or L
position 4: I or V
position 8: Q or R or T
position 10: D or N
position 11: P or Y
position 12: L or N or Q
position 13: L or N, and
position 19: E or Q The 6th motif is preferably composed of an amino acid sequence having an identity of 60% or more with the amino acid corresponding to the 5th motif of RsXI expressed by LGSVDANTGDPLLGWDTDEFP (SEQ ID NO:28). The 5th motif is more preferably composed of an amino acid sequence having an identity of 65% or more with the amino acid sequence expressed by SEQ ID NO:28, still more preferably 70% or more, and even more preferably 75% or more. The identity may be 80% or more, may be 85% or more, may be 90% or more, and further may be 95% or more.

As obvious from FIG. 2, with respect to the 5th motif, 10 XIs having activity in yeast shown in FIG. 1 have preferably an identity of amino acid sequence of 71% or more, preferably 75% or more, and more preferably 80% or more.

(The 6th motif)
The 6th motif is expressed by GGXNFDXKXRR (SEQ ID NO:7). The 6th motif is composed of 11 amino acids and corresponds to position 335 to position 345 of the amino acid sequence of RsXI expressed by SEQ ID NO:1. It is presumed that in the motif the amino acid residue at position 6 (D) is a residue constituting an active site.

The respective X's (naturally occurring amino acids) in the 6th motif expressed by SEQ ID NO:7 are preferably the following amino acids:
position 3: F or I or L or M or T or V
position 7: A or C or S or T, and
position 9: I or L or P or T or V.

The 6th motif is preferably expressed by GGX-NFDXKXRR (SEQ ID NO:13). The respective X's (naturally occurring amino acids) in the 6th motif expressed by SEQ ID NO:13 are preferably the following amino acids:
position 3: F or I or L or T
position 7: A or C or S, and
position 9: T or V.

The respective X's (naturally occurring amino acids) in the 6th motif expressed by SEQ ID NO:13 are preferably the following amino acids. This 6th motif is based on the results of an alignment analysis performed with the amino acid sequence of RsXI (SEQ ID NO:1) and amino acid sequences of XIs originated from *Piromyces* sp. E2, *Clostridium phytofermentans, Bacteroides thetaiotaomicron*, and *Lactococcus lactis* respectively.
position 3: I or L or T
position 7: A or S, and
position 9: T or V The 6th motif is preferably composed of an amino acid sequence having an identity of 60% or more with the amino acid corresponding to the 6th motif of RsXI expressed by GGLNFDSKVRR (SEQ ID NO:29). The 6th motif is more preferably composed of an amino acid sequence having an identity of 65% or more with the amino acid sequence expressed by SEQ ID NO:29, still more preferably 70% or more, and even more preferably 75% or more. The identity may be 80% or more, may be 85% or more, may be 90% or more, and further may be 95% or more.

As obvious from FIG. 2, with respect to the 6th motif, 10 XIs having activity in yeast shown in FIG. 1 have preferably an identity of amino acid sequence of 72% or more, preferably 75% or more, more preferably 80% or more, still more preferably 85% or more, and even more preferably 90% or more.

The present protein has an amino acid sequence, in which asparagine (N) in the 6th motif is another amino acid. In other words, it has an amino acid sequence, in which asparagine in the 6th motif is substituted with another amino acid. The asparagine in the 6th motif is considered to have important value for improving the xylose utilization (fermentation) ability of a eukaryotic cell owing to a XI having certain relationship with RsXI.

There is no particular restriction on a substituting other amino acid for N in the 6th motif, and those skilled in the art can specify the same by introducing a point mutation to the position of asparagine in the 6th motif by a publicly known mutagenesis method to generate a modified protein, introducing the modified protein into a eukaryotic cell such as yeast, and comparing the improved xylose utilization ability with a wild type protein.

Examples of a preferable other amino acid include cysteine, threonine, valine and alanine. A mutation by substituting any of the above amino acids for asparagine is preferable. In some cases, cysteine or threonine is more preferable.

All of the identities with respect to the 1st to the 6th motifs of the present protein are preferably 65% or more, and more preferably any of the identities are 70% or more.

Further, all of the identities with respect to the 2nd to the 4th motifs of the present protein are preferably 75% or more, and more preferably 80% or more.

Further, the present protein has preferably an amino acid sequence having an identity of 45% or more with respect to an amino acid sequence of RsXI expressed by SEQ ID NO:1 and more preferably an amino acid sequence having an identity of 50% or more.

Amino acid sequences within a predetermined range of identity with respect to the respective amino acid sequences of the various motifs and the amino acid sequence expressed by SEQ ID NO:1 of RsXI are amino acid sequences derived by deletion, substitution, or addition of one or several amino acids from the amino acid sequence in question. A mutation of an amino acid in an amino acid sequence, namely deletion, substitution, and addition, may occur singly or in combination of 2 or more types thereof. Further, there is no particular restriction on the total number of mutations, insofar as the identity is within a specified range.

The present protein has xylose isomerase activity. "XI activity" is the activity of isomerizing xylose into xylulose. XI activity can be measured by known methods using the reduction in the amount of xylose as the substrate of this isomerization reaction, or the amount of xylulose produced by the reaction. "Having XI activity" simply means that there is XI activity. Preferably, this means that the XI activity is equivalent to or greater than that of a protein consisting of an amino acid sequence represented by SEQ ID NO: 1 or any one of SEQ ID NO: 14-23. The XI activity can be measured based on the consumption amount or the consumption rate of xylose or production amount of xylulose by the present protein or XI content fraction such as cell lysate of the present protein expressing eukaryotic cell such as yeast. The XI activity is preferably at least 70% or more preferably at least 80% or still more preferably at least 90% or most preferably at least 100% of the XI activity of the protein consisting of an amino acid sequence represented by SEQ ID NO: 1 or any one of SEQ ID NO: 14-23 or the present protein which has Asparagine at the specified site (typically wild type xylose isomerase).

When the present protein is expressed in a eukaryotic cell such as yeast, the xylose utilization ability of the eukaryotic cell is preferably higher than the xylose utilization ability evaluated under the same conditions for a protein equivalent to the present protein, in which the specific position is asparagine (typically, a protein having wild type xylose isomerase activity (wild type protein)). Xylose utilization ability is evaluated, for example, by the growth amount (rate) of a eukaryotic cell, the xylose consumption amount (rate), the fermentation production amount (e.g. ethanol), or the like in the presence of xylose. This is because xylose utilization ability is the ultimately required function. The xylose utilization ability is preferably 110% or more as high as that of the wild type protein, more preferably 120% or more, still more preferably 130% or more, even more preferably 150% or more, still even more preferably 200% or more, yet even more preferably 250% or more, and most preferably 300% or more.

Examples of the present protein include proteins having amino acid sequences containing an amino acid other than asparagine at the asparagine position of the 6th motif in SEQ ID NO:1 and SEQ ID NOs:14 to 23. Namely, with respect to RsXI, examples include a protein having the amino acid sequence expressed by SEQ ID NO:30, with respect to a XI originated from *Clostridium phytofermentans* a protein having the amino acid sequence expressed by SEQ ID NO:31, with respect to a XI originated from *Clostridium difficile* a protein having the amino acid sequence expressed by SEQ ID NO:32, with respect to a XI originated from *Fusobacterium mortiferum* a protein having the amino acid sequence expressed by SEQ ID NO:33, with respect to a XI originated from *Bacteroides* thetaiotaomicron a protein having the amino acid sequence expressed by SEQ ID NO:34, with respect to a XI originated from *Cyllamyces aberensisn* a protein having the amino acid sequence expressed by SEQ ID NO:35, with respect to a XI originated from *Bacteroides fragilis* a protein having the amino acid sequence expressed by SEQ ID NO:36, with respect to a XI originated from *Orpinomyces* sp. ukk1 a protein having the amino acid sequence expressed by SEQ ID NO:37, with respect to a XI originated from *Piromyces* sp. E2 a protein having the amino acid sequence expressed by SEQ ID NO:38, with respect to a XI originated from *Lactococcus lactis* a protein having the amino acid sequence expressed by SEQ ID NO:39, and with respect to a XI originated from *Ciona intestinals* a protein having the amino acid sequence expressed by SEQ ID NO:40.

Further, the present protein includes, for example, proteins having an amino acid sequence having an identity of 70% or more, preferably 75% or more, still more preferably 80% or more, even more preferably 85% or more, still even more preferably 90% or more, yet even more preferably 95% or more, and most preferably 98% or more with any of amino acid sequences expressed by SEQ ID NO:1, and SEQ ID NOs:14 to 23, as well as an amino acid other than asparagine (preferable examples are cysteine, threonine, valine, and alanine; a mutation substituting any of the amino acids for asparagine is preferable; and in some cases cysteine and threonine are preferable) substituting for asparagine at a position corresponding to position 337 of SEQ ID NO:1. Meanwhile, the expression "position corresponding to" means, when alignment of an amino acid sequence to be compared having a certain amino acid sequence identity with respect to a base amino acid sequence such as SEQ ID NO:1 is performed, a position of the amino acid sequence to be compared corresponding to a specific position of the base amino acid sequence. In amino acid sequences expressed by SEQ ID NOs:14 to 23, positions corresponding to the position 337 are position 337, position 337, position 335, position 339, position 338, position 339, position 338, position 338, position 337, and position 357.

The present protein is preferably protein having an amino acid sequence having an identity of 70% or more, preferably 75% or more, more preferably 75% or more, still more preferably 80% or more, even more preferably 85% or more, still even more preferably 90% or more, yet even more preferably 95% or more, and most preferably 98% or more with any of amino acid sequences expressed by SEQ ID NO:1, SEQ ID NOs:14, 17, 21 and 22, and having asparagine at a position corresponding to position 337 of SEQ ID NO:1 substituted with an amino acid other than asparagine (preferable examples are cysteine, threonine, valine, and alanine; a mutation substituting any of the amino acids for asparagine is preferable; and in some cases cysteine and threonine are preferable).

The present protein is available by various methods. For example, the present protein can be obtained by extracting a protein having the 1st to 5th motifs at identities not less than a certain level by means of a publicly known homology search, motif analysis, or the like using an amino acid sequence selected from the group consisting of SEQ ID NOs:1 and 14 to 23, or a nucleotide sequence coding for the amino acid sequence as a query sequence; and introducing a mutation to an asparagine position in the 5th motif of the extracted protein. Site-specific introduction of a mutation into an amino acid sequence is possible by those skilled in the art according to a publicly known technique. Example of a method for preparing DNA coding for a protein with a modified amino acid sequence well known to those skilled in the art include a site-directed mutagenesis method (Kramer W, and Fritz H-J: Methods Enzymol 154: 350, 1987).

Alternatively, proteins containing an amino acid other than asparagine at a specific asparagine may be extracted using, for example, SEQ ID NOs:30 to 40 substituting a specific asparagine position with another amino acid in SEQ ID NOs:1 and 14 to 23, or a nucleotide sequence coding for the same as a query sequence. Also in the natural world, by a mutation of a nucleotide sequence, a mutation of the encoded amino acid sequence of a protein may take place.

Further, a DNA may be isolated by a hybridization technique using a DNA coding for an amino acid sequence expressed by SEQ ID NOs:1, 14 to 23, or 30 to 40, or the complementary strand thereof as a probe, and a wild type of the present protein encoded by the DNA may be obtained, followed by modification; or the present protein may be obtained directly. Further, using an oligonucleotide which hybridizes specifically with the DNA or the complementary strand as a primer, a wild type of the present protein may be obtained by a PCR reaction, followed by modification, or the present protein may be obtained directly. Acquisition of the present protein as above can be performed routinely by those skilled in the art.

With respect to a hybridization technique, a hybridization reaction should preferably be carried out under a stringent condition. The stringent condition will be described below.

The present protein is prepared by transforming an appropriate host, such as a eukaryotic cell, by a DNA construct containing a DNA coding for the present protein, culturing the transformed host cell by an ordinary method well known to those skilled in the art, and harvesting the present protein from the cultured cells or culture medium. The technique is well known to those skilled in the art.

(DNA Coding for the Present Protein)

The present DNA is a DNA with a nucleotide sequence coding for the present protein. The present DNA can be obtained by preparing synthetically a DNA coding for the present protein, or as described above, by a site-directed mutagenesis method, a hybridization technique, a PCR, or the like.

Stringent condition in hybridization refers to conditions, for example in which so-called specific hybrid is formed, a non-specific hybrid is not formed. For example, a condition such that complementary strand of the DNA having high identity such as at least 70% identical, preferably at least 80% identity, more preferably at least 85%, or still more preferably at least 90%, or most preferably at least 95% identity with the nucleotide sequence represented by any one of SEQ ID NOS: 1, 3, 5, 7, 9, 11 or 13 hybridizes with the DNA while the complementary strand of the DNA having the lower identity does not hybridize with the DNA is included. Typically, Na salt concentration is 15 to 750 mM, preferably 50 to 750 mM, more preferably 300 to 750 mM, temperature is 25 to 70 deg C., preferably 50 to 70 deg C., more preferably 55 to 65, and formamide concentration is 0 to 50%, preferably 20 to 50%, more preferably 35 to 45%. Further, stringent condition includes filter washing condition after hybridization which Na salt concentration is 15 to 600 mM, preferably 50 to 600 mM, more preferably 300 to 600 mM and temperature is 50 to 70 deg C., preferably 55 to 70 deg C., more preferably 60 to 65 deg C., typically.

In a nucleotide sequence coding for a specific amino acid sequence, at least one base in a nucleotide sequence coding for the predetermined amino acid sequence can be substituted with another kind of base as per degeneracy in genetic coding without changing an amino acid sequence of a protein. Therefore, the present DNA includes a DNA coding for a nucleotide sequence modified by substitution as per degeneracy in genetic coding. The present DNA may be constituted with a nucleotide sequence optimized for expression in a eukaryotic cell, such as yeast.

(Vector for Transformation)

The vector for transformation disclosed herein retains the present DNA downstream of an appropriate promoter as operable by the promoter. Examples of the promoter include various promoters functioning in a eukaryotic cell, etc. as described below, and inductive promoters, such as a GAL promoter. The recombinant vector for transformation may be further provided with a terminater, an enhancer, a replication origin (ori), a marker, etc., and such elements may be selected appropriately according to need. Further, in the event that the recombinant vector is intended to implant a desired DNA fragment into a chromosome, as for gene substitution, the same has a homologous domain corresponding to a predetermined domain on the chromosome. Further, the present vector can be constructed utilizing an appropriately selected commercially available yeast expression vector, etc.

Such general manipulations required for constructing a recombinant vector are conducted routinely by those skilled in the art, and those skilled in the art can carry out the same by referring appropriately to a handbook of experimental techniques, for example, T. Maniatis, J. Sambrook, et al. "Molecular Cloning, A Laboratory Manual", Cold Spring Harbor Laboratory, 1982, 1989, 2001.

(Eukaryotic Cell)

The eukaryotic cell disclosed herein is a eukaryotic cell containing the present DNA. The present eukaryotic cell is typically a transformed eukaryotic cell transformed by the present vector. The DNA may be retained outside a chromosome in a host cell, but is preferably retained on a chromosome. Further, for exhibiting high xylose utilization ability, it is preferable, for example, that a plurality of copies thereof are retained.

There is no particular restriction on a eukaryotic cell as a host of a transformant disclosed hereunder. From the standpoint of substance production and the like, it may be an *Aspergillus* or other mold or yeast. Examples of *Aspergillus* species include *Aspergillus aculeatus, Aspergillus orizae* and the like. Examples of yeasts include various known yeasts including *Saccharomyces cerevisiae* and other *Saccharomyces* yeasts, *Schizosaccharomyces pombe* and other *Schizosaccharomyces* yeasts, *Candida shehatae* and other *Candida* yeasts, *Pichia stipitis* and other *Pichia* yeasts, *Hansenula* yeasts, *Klocckera* yeasts, *Schwanniomyces* yeasts and *Yarrowia* yeasts, *Trichosporon* yeasts, *Brettanomyces* yeasts, *Pachysolen* yeasts, *Yamadazyma* yeasts, *Kluyveromyces marxianus, Kluyveromyces lactis* and other *Kluyveromyces* yeasts, *Issatchenkia orientalis* and other *Issatchenkia* yeasts and the like. Of these, a *Saccharomyces* yeast is preferred from the standpoint of industrial utility and the like. Of these, *Saccharomyces cerevisiae* is preferred.

The DNA is carried by the host in such a way that it can be expressed. That is, it may be linked under the control of a suitable promoter, and a terminater, enhancer, replication origin (ori), marker or the like may also be provided. The promoter may be inductive or constitutive. Examples of constitutive promoters in yeasts include the 3-phosphoglycerate kinase (PGK) promoter, glyceraldehyde-3-phosphate dehydrogenase (GAPDH) promoter, alcohol dehydrogenase 1 (ADH1) promoter, histidine nutritional function gene (HIS3) promoter, cytochrome bc1 complex (CYC1) promoter and hyperosmolarity responsive 7 gene (HOR7) promoter and modifications of these.

The eukaryotic cell may also be one that secretorily expresses a cellulase or hemicellulase either extracellularly or on the cell surface. Examples include endoglucanase, cellobiohydrolase, β-glucosidase and various other cellulases as well as hemicellulase and other biomass degrading enzymes. Expression of such proteins allows for effective utilization of sugars other than lignin derived from lignocellulose. The transformant disclosed in this Description may also be one that has been given genetic engineering modifications as necessary, such as introduction of an exogenous gene or disruption of an endogenous gene.

The eukaryotic cell may be one capable of producing desired useful chemicals by fermentation as explained below. An eukaryotic cell capable of producing a useful chemical may be provided with an endogenous gene and/or exogenous gene involved in producing the useful chemical. A desired endogenous gene may also be disrupted. Yeasts ordinarily produce ethanol by anaerobic fermentation, but a host that has been transformed by genetic engineering modifications or the like to make it capable of producing another useful chemical is also possible. Examples of useful chemicals include not only ethanol but also lactic acid, acetic acid, 1,3-propane-diole, propanol, butanol, succinic acid, ethylene and glycerol. Preferably the transformant is capable of producing one or two or more of these as useful substances. The host of the transformant disclosed in this Description may comprise a genetic modification or the like to yeast or the like that produces an organic acid such as lactic acid (Japanese Patent Application Publication No. 2003-259878, Japanese Patent Application Publication No. 2006-006271, Japanese Patent Application Publication No. 2006-20602, Japanese Patent Application Publication No. 2006-75133, Japanese Patent Application Publication No. 2006-2966377 and Japanese Patent Application Publication No. 2007-89466).

Introducing methods of the vector into the host cell include calcium phosphate method, transformation, transfection, conjugation, protoplast fusion, electroporation, lipofection, lithium acetate method and any other methods known to the art. These techniques are described in published books including the above mentioned text. The transformant of the present Description can be obtained by screening by the marker gene or the expression of the activity of the gene among yeast which the vector is introduced.

(Method of Producing Useful Chemical)

The useful chemical production method disclosed in this Description is provided with a step of culturing the eukaryotic cell in the presence of xylose. Because the eukaryotic cell has xylose utilization ability, it can effectively use any xylose contained as a carbon source, and convert it into a useful substance in the production method disclosed in this Description. Thus, even when the medium contains saccharides of lignocellulose including xylose, this biomass carbon source can be effectively utilized and converted into a useful substance. In addition to xylose, the lignocellulose saccharides may include glucose, as well as hemicellulose decomposition products.

Xylose includes arabinoxylan, glucuronoxylan and other xylans. In nature, these polymers form one component of hemicellulose, and are present in lignocellulose and other forms of biomass and the like. Xylose can be obtained by digesting xylans with an endoxylanase, xylosidase or the like.

The useful chemical may also be a compound that is not an intrinsic metabolite, but one that the yeast has been made capable of synthesizing by a genetically engineered substitution, addition or the like in one or two or more enzymes in the glucose metabolism system. Examples of useful chemicals include ethanol as well as lower alcohols, lactic acid, acetic acid and other organic acids. In addition, 1,3-propane-diol, propanol, butanol, succinic acid, glycerol and ethylene, farnesol, geranylgeraniol, squalene and other terpenoids and fine chemicals (coenzyme Q10, vitamins and other raw materials and the like) obtained by addition of isoprenoid synthesis pathways. Further, glycerin, plastics, synthetic raw materials and the like obtained by modifications in the glycolytic system and other materials used in biorefinery technology are included. As yeast has high performance of alcohol fermentation, the transformant can produce ethanol effectively in the medium with carbon source including xylose. An yeast having high performance of alcohol fermentation has high performance of an organic acid and other useful substances by modifications in the glycolytic system.

In the step of culturing, a medium which contains xylose as a carbon source is used. Further, the medium can contain glucose. Preferably, the carbon sources which are derived from biomass carbon source including lignocellulose. In addition, when yeast expresses cellulases and has an ability to metabolize cellulose, cellulose or the partial degradation products thereof can be included in the medium.

The culturing step can be accomplished according to a culture condition selected appropriately from the general culture conditions applied to the host cell of the eukaryotic cell. Typically, static culture, shaking culture or aerated stirred culture or the like can be used as the culture for fermentation. The aeration conditions can be set appropriately as anaerobic conditions, microaerobic conditions or aerobic conditions. The culture temperature is not particularly limited, and can be in the range of 25 deg C. to 55 deg C. The culture time can be set as necessary, and can be a few hours to about 150 hours. The pH can be adjusted with an inorganic or organic acid or alkali solution or the like. An antibiotic such as ampicillin or tetracycline can be added to the medium as necessary during culture.

By means of the culturing step, a useful chemical is produced according to the useful substance production ability of the microorganism used. For example, ethanol is obtained with the eukaryotic cell that has the ability to produce ethanol. The eukaryotic cell that has the ability to produce lactic acid and other organic acids due to biogenetic modification or the like can be used to produce lactic acid and the like. After completion of the useful substance production step, there can be a step in which the fraction containing the useful substance is collected from the culture liquid, and another step in which it is purified or concentrated. The processes for collection, purification and other process can be selected appropriately according to the type of useful substance and the like.

The useful substance production step may be followed by a step of collecting a useful substance-containing fraction from the culture liquid, and a further step of refining or concentrating this fraction. The collection step and refining or other step can be selected appropriately according to the type of useful substance and the like.

(Screening Method of Protein Having Xylose Isomerase Activity)

The present specification provides a screening method of protein having xylose isomerase activity. The present screening method can comprise a step of assessing xylose isomerase activity of modified protein when aligned with an amino acid sequence expressed by SEQ ID NO: 1, where the modified protein contains the following 1st to 6th motifs from the N-terminus of the protein in the order described, and has, in place of asparagine (N) in an amino acid sequence of the 6th motif of the protein having xylose isomerase activity, another amino acid. According to the method, the modified protein improved with respect to xylose isomerase activity can be obtained. Especially, a modified protein that is useful for expression in yeast can be obtained. The aforementioned another amino acid to be substituted is selected from various naturally occurring amino acids, and among these, cysteine, threonine, alanine and valine, in particular, cysteine and threonine can be exemplified. As for the $1^{st}$ to $6^{th}$ motifs in the modified protein, it is possible to apply the preferred embodiments described above.

As the protein source for obtaining such a modified protein, the amino acid sequences of RsXI can be searched as a query sequence by Protein BLAST (Database used the Non-redundant protein sequence, and Algorism parameter was in a default setting), and the top 500 species of the other similar amino acid sequences can be used; and among them, preferably the top 400 species, the top 300 species, the top 200 species, or the top 100 species of proteins may be exemplified. The position of asparagine in the $6^{th}$ motif may be identified using alignment analysis as described above. Notably, the modified protein to be subjected to screening can be obtained by a method of obtaining proteins as discussed above.

(Process for Producing a Protein Having Xylose Isomerase Activity)

According to this specification, a process for producing a protein having xylose isomerase activity is also provided. The present production method can comprise a step of producing a protein having xylose isomerase activity, which is a modified protein that, when aligned with an amino acid sequence expressed by SEQ ID NO: 1, contains the following 1st to 6th motifs from the N-terminus of the protein in the order described, and has, in place of asparagine (N) in an amino acid sequence of the 6th motif of the protein having xylose isomerase activity, another amino acid. According to the method, the modified protein having xylose isomerase activity can easily be produced. For the various aspects of other amino acids, protein source, and motifs, various aspects described hereinabove can be adapted similar to the screening method described above.

EMBODIMENTS

The present teaching is explained in detail below using examples, but the present invention is not limited by these examples. The genetic recombination operations described below were performed in accordance with Molecular Cloning: A Laboratory Manual (T. Maniatis, et al., Cold Spring Harbor Laboratory)

The compositions of culture media used in the following Examples are as follows:

SD agar culture medium: 6.7 g/L Yeast Nitrogen Base without amino acid, 20 g/L D-Glucose, and 20 g/L Agar
SX liquid culture medium: 6.7 g/L Yeast Nitrogen Base without amino acid, and 20 g/L D-Xylose
SX agar culture medium: 6.7 g/L Yeast Nitorogen Base without amino acid, 20 g/L D-Xylose, and 20 g/L Agar
SX liquid culture medium 50: 6.7 g/L Yeast Nitorogen Base without amino acid, and 50 g/L D-Xylose First Embodiment (Introduction of Mutation in RsXI Gene by Error-Prone PCR)

An error-prone PCR was carried out using GeneMorphII (by Stratagene) with pRS436GAP-RsXIC1-O, to which a xylose isomerase gene RsXI-C1-opt (GenBank: HV438143) originated from an enteric protist of *Reticulitermes speratus* optimized to a yeast codon was inserted, as a template. The reaction was carried out for 30 cycles with a cycle of at 95 deg C. for 2 min, 95 deg C. for 1 min, 60 deg C. for 1 min, and 72 deg C. for 1 min 30 sec, and followed by a reaction at 72 deg C. for 10 min. The sequences of the used primers were as follows:

```
pRSSacII-AAA-ATG-F4:
                                        (SEQ ID NO: 41)
5'-GAACTTAGTTTCGAATAAACACACATAAACAAACAAACCGCGG
AAAATG-3',
and pRSXhoI-TAA-R3:
                                        (SEQ ID NO: 42)
5'-GTGAATGTAAGCGTGACATAACTAATTACATGATGCGGCCCTC
GAGTTA-3'.
```

An amplified DNA fragment was cloned to PCR-Blunt II TOPO using a Zero Blunt TOPO PCR cloning kit (by Invitrogen) and the inserted DNA fragment was analyzed. As the result, it was confirmed that average 3 mutations per 1000 bases in the DNA fragment (error rate 0.3%) were introduced randomly.

Second Embodiment (Construction of Yeast Gene Expression-Basic Plasmid)

A low-copy type transgenic vector pRS316GAP was constructed. A PCR was conducted with pRS436GAP (DDBJ accession number: AB304862) as a template using primers TDH3p-CYC1t-IF-F and R. The PCR was carried out using a PrimeSTAR HS DNA polymerase (Takara Bio Inc.) with a cycle of at 98 deg C. for 10 sec, 55 deg C. for 15 sec, 72 deg C. for 1 min 30 sec and by repeating 30 cycles. The sequences of the used primers were as follows:

```
TDH3p-CYC1t-IF-F:
                                        (SEQ ID NO: 43)
5'-TCGCTATTACGCCAGCTGGCGAAAGGGGGATGTGC-3',
and TDH3p-CYC1t-IF-R:
                                        (SEQ ID NO: 44)
5'-GATTCATTAATGCAGCTGGCACGACAGGTTTCCCGACTG
GAAAGC-3'.
```

The produced DNA fragment was inserted using an In-Fusion Advantage PCR cloning kit (Takara Bio Inc.) in pRS316 (NBRP accession number: BYP562) digested by a restriction enzyme PvuII. The obtained plasmid was designated as pRS316GAP.

Third Embodiment (Introduction of DNA Originated from Variant XI Gene Library into Yeast)

A DNA fragment produced by an error-prone PCR or a DNA fragment (control) produced by a PCR using pRS436-GAP-RsXIC1-O as a template, pRSSacII-AAA-ATG-F4 and pRsXhoI-TAA-R3 as primers, and a PrimeSTAR HS DNA polymerase as a polymerase were mixed with pRS316GAP digested by restriction enzymes SacII and XhoI, and introduced in yeast of *Saccharomyces cerevisiae* W600W strain (see Japanese Patent Application Publication No. 2011-147445) using Frozen-EZ Yeast Transformation II (Zymo Research), which was then cultured in 5 mL of an SD liquid culture medium.

Fourth Embodiment (Enrichment Culture in Culture Medium Using Xylose as Carbon Source)

The SD culture solution in the Third Embodiment after a 2-day culture was added to 5 mL of an SX liquid culture medium, and cultured at 30 deg C., and 70 rpm in a BioPhotorecorder TVS062CA (Advantech). Cells were recovered from the culture solution on day 7 from the initiation of the culture, and added to 5 mL of a fresh SX liquid culture medium to a initial culture solution concentration of 0.1 in terms of OD (600 nm). The solution was cultured at 30 deg C., and 70 rpm for 7 days using a BioPhotorecorder, and cells were recovered from the culture solution. The cells were spread on an SX agar culture medium and cultured at 30 deg C. Colonies grown faster than yeast, to which a DNA fragment of RsXI-C1-opt was introduced, were selected, streaked on an SD agar culture medium and cultured to be purified as selected strains.

Fifth Embodiment (Extraction of Plasmids from Selected Strains and Sequencing Analyses)

From top 10 strains in terms of specific growth rate in the growth test in the Fourth Embodiment, and the strain having introduced RsXI-C1-opt, plasmids were extracted using a Yeast Plasmid Minipreparation kit, Zymoprep (Zymo research). As the results of analyses of RsXI-C1-opt gene domains in extracted plasmids, 5 types of mutant sequences were recognized. The mutant XI genes were designated respectively as RsXIC1O-T76I, RsXIC1O-E125G, RsXIC1O-I286F, RsXIC1O-N337T and RsXIC1O-K384E; and yeast expression vectors for the respective genes were designated as pRS316GAP-RsXIC1O-T76I, pRS316GAP-RsXIC1O-E125G, pRS316GAP-RsXIC1O-I286F, pRS316GAP-RsXIC1O-N337T, and pRS316GAP-RsXIC10-K384E. Further, a yeast expression vector of a wild type RsXI-C1-opt was designated as pRS316GAP-RsXIC1O.

Sixth Embodiment (Introduction of Mutant Gene into Yeast)

A plasmid prepared in the Fifth Embodiment was introduced in yeast of *Saccharomyces cerevisiae* W600W strain (see Japanese Patent Application Publication No. 2011-147445) identically with the Third Embodiment using Frozen-EZ Yeast Transformation II (Zymo Research), and the yeast was spread on an SD agar culture medium and cultured at 30 deg C. Grown colonies were streaked over a fresh SD agar culture medium and cultured for purification. The obtained selected strains after purification as well as the used plasmids were designated as below.

WR701Is: pRS316GAP-RsXIC1O-T76I
WR702Gs: pRS316GAP-RsXIC1O-E125G
WR703Fs: pRS316GAP-RsXIC1O-I286F
WR704 Ts: pRS316GAP-RsXIC1O-N337T
WR705Es: pRS316GAP-RsXIC10-K384E, and
WR700s: pRS316GAP-RsXIC1O

Seventh Embodiment (Growth Test of Genetically Modified Yeast Utilizing Xylose as Carbon Source)

Growth tests in a culture medium containing xylose as a carbon source were conducted for evaluating the xylose utilization ability of the yeasts obtained in the Sixth Embodiment. 5 types of the strains prepared in the Sixth Embodiment were cultured in an SD liquid culture medium for 24 hours, and the cells were recovered and washed with sterilized water. Thereafter, in an SX liquid culture medium prepared in an L-shaped test tube, the cells were added and a growth test was initiated. During the growth test under culture conditions of 30 deg C., 70 rpm using a BioPhotorecorder TVSO62CA, the OD (660 nm) of the culture solution was measured at 20 min intervals. A comparison of the specific growth rates of the respective strains is shown in FIG. 5.

Figure 5:
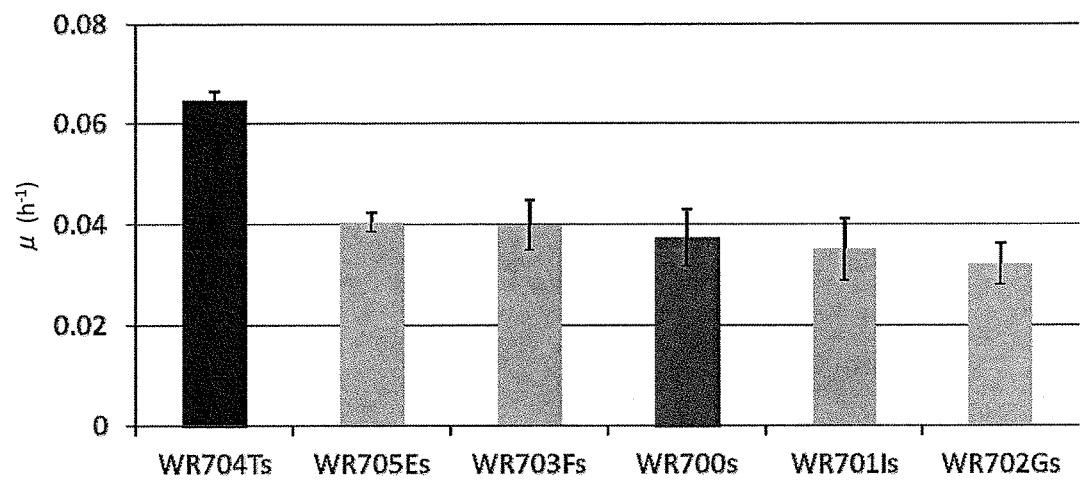
FIG. 5 is a graph showing growth test results (specific growth rates) utilizing xylose as a carbon source.

As shown in FIG. 5 it was confirmed that the specific growth rates of the WR703Fs strain having introduced RsXIC1O-I286F, the WR704 Ts strain having introduced RsXIC1O-N337T, and the WR705Es strain having introduced RsXIC1O-K384E are higher than that of the WR700s strain having introduced the wild type RsXI-C1-opt. Among others, the specific growth rate of the WR704 Ts strain was 1.6-fold the WR700s strain.

Eighth Embodiment (Fermentation Test of Genetically Modified Yeast Utilizing Xylose as Carbon Source)

Figure 6:
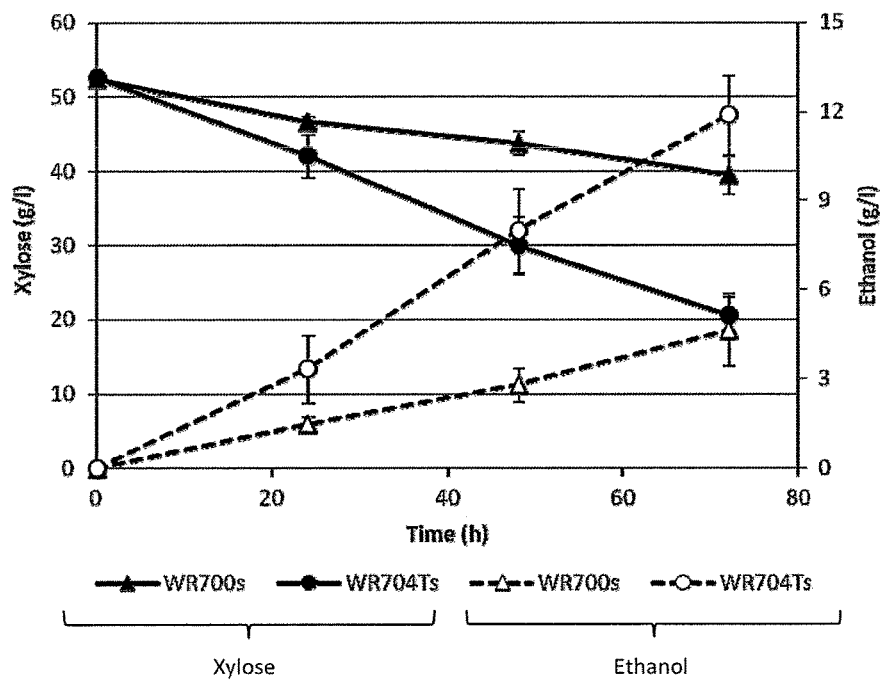
FIG. 6 is a graph showing fermentation test results (change of xylose and ethanol with time) utilizing xylose as a carbon source.

The WR700s strain and the WR704 Ts strain were inoculated in a 5 mL of SD liquid culture medium and cultured for 24 hours. Next, 1 mL of the culture solution was added to 50 mL of an SD liquid culture medium and cultured for 24 hours. The cells were recovered and washed twice by sterilized water. For a fermentation test a pressure-resistant test tube with a screw top sealed tightly with a butyl rubber closure was used. 5 mL of an SX liquid culture medium 50 was prepared by adding a yeast suspension to the final OD (600 nm) of a fermentation medium of 10, and fermented at 30 deg C., and 180 rpm. At discretionary timing an aliquot of the fermented liquid was sampled and analyzed by liquid chromatography about xylose and ethanol. As a column for liquid chromatography an HPX-87H column (Bio-RAD) was used at 60 deg C., and as a detector a differential refractive index detector RID-10A (Shimadzu Corporation) was used. For a mobile phase a 0.05% sulfuric acid solution was used, and supplied at a flow rate of 0.8 mL/min. FIG. 6 shows time-dependent changes of xylose concentration and ethanol concentration in the fermentation medium with respect to the respective strains. In this connection, the fermentation tests were repeated 4 times, and the average values are shown.

As shown in FIG. 6, the consuming rate of xylose and the ethanol production rate of the WR704 Ts strain are approx. 2.5 times as higher as the WR700s strain, and the xylose consumption by fermentation for 72 hours was approx. 12 g/L for the WR700s strain but approx. 30 g/L for the WR704 Ts strain. From the above it has become clear that the xylose utilization ability of yeast can be improved by substituting asparagine at position 337 of RsXI with threonine.

Ninth Embodiment (Construction of Amino Acid Point Mutation Library and Introduction into Yeast)

An amino acid point mutation library was constructed targeting the 337th amino acid (asparagine) of RsXIC10m, for which an improvement effect of xylose utilization ability in yeast was confirmed. A reaction was conducted using pRS316GAP-RsXIC1O described in the Fifth Embodiment as a template, primers listed in Table 1 below, and a a Quick Change Lightning MultiSite-Directed Mutagenesis kit (Agilent Technologies, Inc.) according to the protocol attached to the kit. Using the obtained reaction solution, ECOS Competent E. coli DH5 alfa (Nippon Gene Co., Ltd.) was transformed and a plasmid was extracted from a grown colony. By sequencing a mutated locus was identified and a plasmid for introduction to yeast for each of mutant XI having any of 18 types of mutations except asparagine and threonine (alanine: A, arginine: R, aspartic acid: D, cysteine: C, glutamine: G, glutamic acid: E, glycine: G, histidine: H, isoleucine: I, leucine: L, lysine: K, methionine: M, phenylalanine: F, proline: P, serine: S, tryptophan: W, tyrosine: Y, and valine: V) was obtained (Table 1). Then an obtained plasmid was introduced in the W600W strain using Frozen-EZ Yeast Transformation II, which was then spread on an SD agar culture medium. A grown colony was streaked over a fresh SD agar culture medium and cultured to purify the colony. The obtained genetically modified yeasts, plasmids used for introducing mutant XI into yeast, and introduced mutant XI genes are shown in Table 1.

Figure 7:
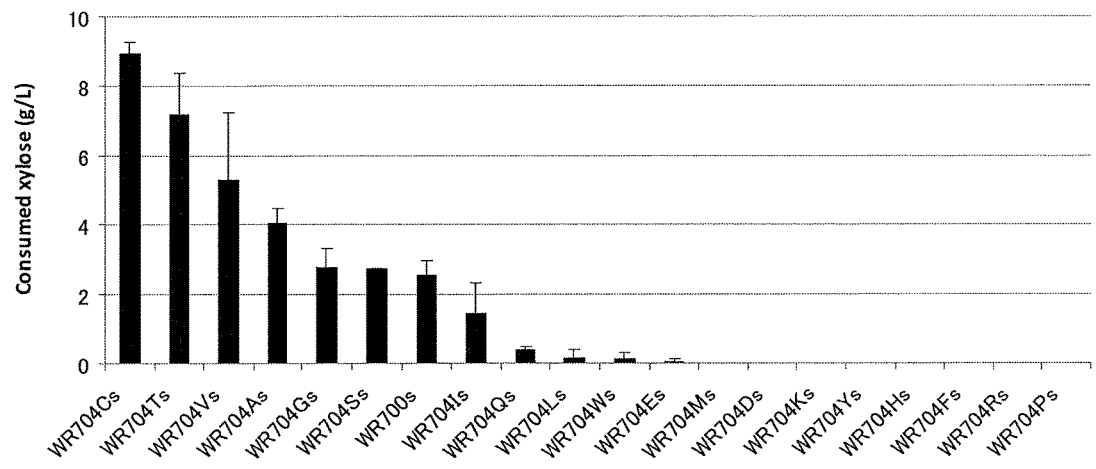
FIG. 7 is a chart showing fermentation test results (xylose consumption in 72 hours) utilizing xylose as a carbon source.

24 hours. Next, 200 microliters of the culture solutions were added to 1 mL of SD liquid culture media prepared in a 96-well Storage Block and cultured under the similar conditions for 24 hours. The cells were recovered, washed twice with sterile water, and suspended in sterile water to prepare yeast suspensions. A fermentation test was performed under the following conditions. 1 mL of an SX liquid culture medium was prepared in a 96-well Storage Block, such that a yeast suspension was added therein to the final OD (600 nm) of 1. For establishing an anaerobic condition each well was hermetically sealed with Titer Stick HC (Kajixx Co., Ltd.), and fermentation was conducted in an M-BR-022UP under conditions of 30 deg C., and 1500 rpm. At discretionary timing an aliquot of the fermented liquid was sampled and analyzed by liquid chromatography about xylose and ethanol as in Eighth Embodiment. FIG. 7 shows xylose consumption by yeast having introduced XIs from the initiation of the fermentation to 72 hours there after. The fermentation tests were repeated 2 or more times, and the average values are shown.

As shown in FIG. 7, the xylose consumption after fermentation of 72 hours of the WR700s strain having introduced the wild type RsXI gene (RsXI-C1-opt) was 2.6 g/L, and the xylose consumption of the WR704 Ts strain shown in the Seventh Embodiment was 7.2 g/L. It was confirmed that among 18 types of strains obtained from the point mutation library, the xylose consumption was improved in 3 strains of WR704Cs, WR704Vs, and WR704As surpassing the WR700s (respectively, 8.9 g/L, 5.3 g/L, and 4.0 g/L). Among others, the xylose consumption of the WR704Cs strain exceeded that of the WR704 Ts strain, and it was confirmed that the same was improved to a level 3.5-fold as high as WR700s. From the above it became clear that the xylose utilization ability of yeast could be improved 1.5-fold or more by substituting asparagine at position 337 of RsXI

TABLE 1

| Strain | Vector | Gene | Primer | SEQ ID |
| --- | --- | --- | --- | --- |
| WR704 As | pRS316GAP-RsXIO-N337 A | RsXIO-N337A | RsXI-N337 A-FP-F | 45 |
| WR704 Rs | pRS316GAP-RsXIO-N337 R | RsXIO-N337R | RsXI-N337 R-FP-F | 46 |
| WR704 Ds | pRS316GAP-RsXIO-N337 D | RsXIO-N337D | RsXI-N337 D-FP-F | 47 |
| WR704 Cs | pRS316GAP-RsXIO-N337 C | RsXIO-N337C | RsXI-N337 C-FP-F | 48 |
| WR704 Qs | pRS316GAP-RsXIO-N337 Q | RsXIO-N337Q | RsXI-N337 Q-FP-F | 49 |
| WR704 Es | pRS316GAP-RsXIO-N337 E | RsXIO-N337E | RsXI-N337 E-FP-F | 50 |
| WR704 Gs | pRS316GAP-RsXIO-N337 G | RsXIO-N337G | RsXI-N337 G-FP-F | 51 |
| WR704 Hs | pRS316GAP-RsXIO-N337 H | RsXIO-N337H | RsXI-N337 H-FP-F | 52 |
| WR704 Is | pRS316GAP-RsXIO-N337 I | RsXIO-N337I | RsXI-N337 I-FP-F | 53 |
| WR704 Ls | pRS316GAP-RsXIO-N337 L | RsXIO-N337L | RsXI-N337 L-FP-F | 54 |
| WR704 Ks | pRS316GAP-RsXIO-N337 K | RsXIO-N337K | RsXI-N337 K-FP-F | 55 |
| WR704 Ms | pRS316GAP-RsXIO-N337 M | RsXIO-N337M | RsXI-N337 M-FP-F | 56 |
| WR704 Fs | pRS316GAP-RsXIO-N337 F | RsXIO-N337F | RsXI-N337 F-FP-F | 57 |
| WR704 Ps | pRS316GAP-RsXIO-N337 P | RsXIO-N337P | RsXI-N337 P-FP-F | 58 |
| WR704 Ss | pRS316GAP-RsXIO-N337 S | RsXIO-N337S | RsXI-N337 S-FP-F | 59 |
| WR704 Ws | pRS316GAP-RsXIO-N337 W | RsXIO-N337W | RsXI-N337 W-FP-F | 60 |
| WR704 Ys | pRS316GAP-RsXIO-N337 Y | RsXIO-N337Y | RsXI-N337 Y-FP-F | 61 |
| WR704 Vs | pRS316GAP-RsXIO-N337 V | RsXIO-N337V | RsXI-N337 V-FP-F | 62 |

Tenth Embodiment (Fermentation Test of Genetically Modified Yeast Utilizing Xylose as Carbon Source)

18 recombinant yeasts in Table 1, the WR700s strain, and the WR704 Ts strain were inoculated to 1 mL of SD liquid culture media prepared in a 96-well Storage Block (Corning Incorporated) with a volume of 2 mL per each well, and cultured in a constant temperature incubator shaker M-BR-022UP (Taitec Corporation) at 30 deg C., and 1500 rpm, for with any one of threonine, cysteine, valine and alanine (DNAs coding for the proteins are expressed respectively by SEQ ID NOs:71 to 74).

Eleventh Embodiment (Introduction of Amino Acid Point Mutation into Other XIs)

Whether the improvement effect on xylose utilization ability obtained by a mutation with respect to the 337th amino acid of RsXI is reproducible in XIs originated from other biological species was investigated. Using a xylose isomerase gene originated from *Piromyces* sp. E2, and a xylose isomerase gene originated from *Clostridium phytofermentans* (Japanese Patent Application Publication No. 2011-147445), which were optimized to yeast codons, as templates, as well as primers listed in the following Table 2, DNA fragments PiXIO-N338T and CpXIO-N337T (SEQ ID NO:75 and SEQ ID NO:76) with introduced mutations substituting asparagine correspond to the 337th amino acid residue of RsXI with threonine, were synthesized. Further, as a control, DNA fragments, PiXIO and CpXIO without an introduced mutation were also simultaneously synthesized. An obtained DNA fragment was inserted into pRS316GAP digested by restriction enzymes SacII and XhoI using an In-Fusion HD PCR cloning kit (Takara Bio Inc.) to obtain a gene transduction plasmid. Then an obtained plasmid was introduced in the W600W strain using Frozen-EZ Yeast Transformation II, which was then spread on an SD agar culture medium. A grown colony was streaked over a fresh SD agar culture medium and cultured to purify the colony. The obtained genetically modified yeasts, plasmids used for introducing a mutant XI into yeast, and introduced mutant XI genes are shown in Table 2.

and 1500 rpm. At discretionary timing an aliquot of the fermented liquid was sampled and analyzed by liquid chromatography about xylose and ethanol similarly as in the Eighth Embodiment. FIG. 8 shows xylose consumption by yeast having introduced XIs from the initiation of the fermentation to 72 hours there after. The fermentation tests were repeated 2 or more times, and the average values are shown.

As shown in FIG. 8A, the xylose consumption after fermentation of 72 hours of a WP700s strain having introduced a XI gene originated from a wild type *Piromyces* sp. E2 (PiXIO) was 2.4 g/L, but the xylose consumption of the WP704 Ts strain having introduced a mutated type XI gene (PiXIO-N338T) was 7.3 g/L. From the above it was confirmed that the xylose consumption of the WP704 Ts strain was improved 3.1-fold compared to the WP700s strain.

Further, as shown in FIG. 8B, the xylose consumption after fermentation of 72 hours of the WC700s strain having introduced a XI gene originated from a wild type *Clostridium phytofermentans* (CpXIO) was 1.8 g/L, but the xylose consumption of a WC704 Ts strain having introduced a mutated type XI gene (CpXIO-N337T) was 2.2 g/L. From the above it was confirmed that the xylose consumption of the WC704 Ts strain was improved 1.2-fold compared to the

TABLE 2

| Strain | Vector | Gene | Primer | SEQ ID |
|---|---|---|---|---|
| WP704Ts | pRS316GAP-PiXIO-N338T | PiXIO-N338T | PiXI-opt-IF-F2 | 63 |
| | | | PiXI-opt-N338T-FP-R | 64 |
| | | | PiXI-opt-N338T-FP-F | 65 |
| | | | PiXI-opt-IF-R2 | 66 |
| WP700s | pRS316GAP-PiXIO | PiXIO | PiXI-opt-IF-F2 | 63 |
| | | | PiXI-opt-IF-R2 | 66 |
| WC704Ts | pRS316GAP-CpXIO-N337T | CpXIO-N337T | CpXI-opt-IF-F2 | 67 |
| | | | CpXI-opt-N337T-FP-R | 68 |
| | | | CpXI-opt-N337T-FP-F | 69 |
| | | | CpXI-opt-IF-R2 | 70 |
| WC700s | pRS316GAP-CpXIO | CpXIO | CpXI-opt-IF-F2 | 67 |
| | | | CpXI-opt-IF-R2 | 70 |

Twelfth Embodiment (Fermentation Test of Genetically Modified Yeast Utilizing Xylose as Carbon Source)

4 types of the recombinant yeasts listed in Table 2 were inoculated in 5 mL of SD liquid culture media, and cultured at 30 deg C., and 100 rpm for 24 hours. In 5 mL of a freshly prepared SD liquid culture medium, 200 microliters of a culture solution was added, and cultured under similar conditions for 24 hours. Cells were recovered, washed twice with sterile water, and suspended in sterile water to prepare a yeast suspension. A fermentation test was performed under the following conditions. 1 mL of an SX liquid culture medium was prepared in a 96-well Storage Block, such that the yeast suspension was added therein to the final OD (600 nm) of 10 in the cases of the WP700s strain and the WP704 Ts strain, and 50 in the cases of the WC700s strain and the WC704 Ts strain. For establishing an anaerobic condition each well was hermetically sealed with Titer Stick HC and fermentation was conducted under conditions of 30 deg C., WC700s strain. From the above it has become clear that the xylose utilization ability of yeast can be improved with PiXI or CpXI similarly as with RsXI by introducing a mutation to the position correspond to position 337 of RsXI.

Thirteenth Embodiment (Introduction of Mutation into XIs Originated from Other Biological Species)

With respect to a XI originated from *Piromyces* sp. E2 (PiXI), a XI originated from *Clostridium phytofermentans* (CpXI), a XI originated from *Bacteroides* thetaiotaomicron (BtXI), and a XI originated from *Lactococcus lactis* (LlXI), for which the activities in a yeast were reported, it was investigated whether the improvement effect on xylose utilization ability could be obtained by substituting an amino acid corresponding to asparagine in position 337 of RsXI with alanine, cysteine, threonine, or valine. Table 3 shows strains, plasmids, genes and primers used for transducing mutations, and Table 4 shows the primer sequences.

TABLE 3

| Strain | Plasmid | Gene | Primer | Seq ID |
|---|---|---|---|---|
| WP700s | pRS316GAP-PiXIO | PiXIO | PiXI-opt-IF-F2 | 77 |
| | | | PiXI-opt-IF-R2 | 78 |

TABLE 3-continued

| Strain | Plasmid | Gene | Primer | Seq ID |
|---|---|---|---|---|
| WP704As | pRS316GAP-PiXIO-N338A | PiXIO-N338A | PiXIO-N338A-FP-F | 86 |
| WP704Cs | pRS316GAP-PiXIO-N338C | PiXIO-N338C | PiXIO-N338C-FP-F | 87 |
| WP704Ts | pRS316GAP-PiXIO-N338T | PiXIO-N338T | PiXIO-N338T-FP-F | 88 |
| WP704Vs | pRS316GAP-PiXIO-N338V | PiXIO-N338V | PiXIO-N338V-FP-F | 89 |
| WC700s | pRS316GAP-CpXIO | CpXIO | CpXI-opt-IF-F2 | 79 |
| | | | CpXI-opt-IF-R2 | 80 |
| WC704As | pRS316GAP-CpXIO-N337A | CpXIO-N337A | CpXIO-N337A-FP-F | 90 |
| WC704Cs | pRS316GAP-CpXIO-N337C | CpXIO-N337C | CpXIO-N337C-FP-F | 91 |
| WC704Ts | pRS316GAP-CpXIO-N337T | CpXIO-N337T | CpXIO-N337T-FP-F | 92 |
| WC704Vs | pRS316GAP-CpXIO-N337V | CpXIO-N337V | CpXIO-N337V-FP-F | 93 |
| WB700s | pRS316GAP-BtXI | BtXI | BtXI-IF-F | 81 |
| | | | BtXI-IF-B | 82 |
| WB704As | pRS316GAP-BtXI-N339A | BtXI-N339A | BtXI-N339A-FP-F | 94 |
| WB704Cs | pRS316GAP-BtXI-N339C | BtXI-N339C | BtXI-N339C-FP-F | 95 |
| WB704Ts | pRS316GAP-BtXI-N339T | BtXI-N339T | BtXI-N339T-FP-F | 96 |
| WB704Vs | pRS316GAP-BtXI-N339V | BtXI-N339V | BtXI-N339V-FP-F | 97 |
| WL700s | pRS316GAP-LIXIO | LIXIO | LIXI-opt-IF-F | 84 |
| | | | LIXI-opt-IF-R | 85 |
| WL704As | pRS316GAP-LIXIO-N337A | LIXIO-N337A | LIXIO-N337A-FP-F | 98 |
| WL704Cs | pRS316GAP-LIXIO-N337C | LIXIO-N337C | LIXIO-N337C-FP-F | 99 |
| WL704Ts | pRS316GAP-LIXIO-N337T | LIXIO-N337T | LIXIO-N337T-FP-F | 100 |
| WL704Vs | pRS316GAP-LIXIO-N337V | LIXIO-N337V | LIXIO-N337V-FP-F | 101 |

TABLE 4

| Seq ID | Primer name | Sequence |
|---|---|---|
| 77 | PiXI-optIF-F2 | 5'-ataaacaaacaaaccg cggaaaatggctaaggaat acttcccacaaatccaaaa gattaaattcgaggg-3' |
| 78 | PiXI-optIF-R2 | 5'-tgatgcggccctcgag ttattggtacatagcaaca attgcttcatacaattctt gtttaccac-3' |
| 86 | PiXIO-N338A-FP-F | 5'-atcagaggtggtggtt ttgttacaggtggtaccgc tttcgatgcaaaaacca g-3' |
| 87 | PiXIO-N338C-FP-F | 5'-atcagaggtggtggtt ttgttacaggtggtacctg tttcgatgcaaaaacca g-3' |
| 88 | PiXIO-N338T-FP-F | 5'-atcagaggtggtggtt ttgttacaggtggtaccac tttcgatgcaaaaacca g-3' |
| 89 | PiXIO-N338V-FP-F | 5'-atcagaggtggtggtt ttgttacaggtggtaccgt tttcgatgcaaaaacca g-3' |
| 79 | CpXI-opt-IF-F2 | 5'-ataaacaaacaaaccg cggaaaatgaagaattact cccaaatgtcccagaagt gaaatatgaaggccc-3' |
| 80 | CpXI-opt-IF-R2 | 5'-tgatgcggccctcgag tcatctaaacaagatgtta ttgacaatagtctccaaga cttcttgtc-3' |
| 90 | CpIXO-N337A-FP-F | 5'-tgaaagctggaggctt tactaatggtggtctagct tttgatgctaaggttagaa gaggcag-3' |
| 91 | CpIXO-N337C-FP-F | 5'-tgaaagctggaggctt tactaatggtggtctatgt tttgatgctaaggttagaa gaggcag-3' |
| 92 | CpIXO-N337T-FP-F | 5'-tgaaagctggaggctt tactaatggtggtctaact tttgatgctaaggttagaa gaggcag-3' |
| 93 | CpIXO-N337V-FP-F | 5'-tgaaagctggaggctt tactaatggtggtctagtt tttgatgctaaggttagaa gaggcag-3' |
| 81 | BtXI-IF-F | 5'-ataaacaaacaaaccg cggaaaatggcaacaaaag aatttttccgggaattga aaagattaaatttg-3' |
| 82 | BtXI-IF-R | 5'-tgatgcggccctcgag ttaatacatattcagaatt gcctcataaagttcttgct tgc-3' |
| 94 | BtXI-N339A-FP-F | 5'-cggtaccggtggtacg gcttttgatgctaaaaccc gtcgtaattctactgat c-3' |
| 95 | BtXI-N339C-FP-F | 5'-cggtaccggtggtacg tgttttgatgctaaaaccc gtcgtaattctactgat c-3' |
| 96 | BtXI-N339T-FP-F | 5'-cggtaccggtggtacg acttttgatgctaaaaccc gtcgtaattctactgat c-3' |
| 97 | BtXI-N339V-FP-F | 5'-cggtaccggtggtacg gttttgatgctaaaaccc gtcgtaattctactgat c-3' |
| 84 | LIXI-opt-IF-F | 5'-ataaacaaacaaaccg cggaaaatggcctacttta acgacatcgcaccaatcaa atacgaaggtactaag-3' |

TABLE 4-continued

| Seq ID | Primer name | Sequence |
|---|---|---|
| 85 | LIXI-opt-IF-R | 5'-tgatgcggccctcgag ttataccaagtagtcgttc aaaacactctttatgtatt ccaaatgg-3' |
| 98 | LIXIO-N337A-FP-F | 5'-gaacggtggtttgggt aaaggtggtatagcttttg atgccaaagtcagaagaac atc-3' |
| 99 | LIXIO-N337C-FP-F | 5'-gaacggtggtttgggt aaaggtggtatatgttttg atgccaaagtcagaagaac atc-3' |
| 100 | LIXIO-N337T-FP-F | 5'-gaacggtggtttgggt aaaggtggtataactttg atgccaaagtcagaagaac atc-3' |
| 101 | LIXIO-N337V-FP-F | 5'-gaacggtggtttgggt aaaggtggtatagtttttg atgccaaagtcagaagaac atc-3' |

(Preparation of Template DNA)

Preparation of a template DNA for introducing a point mutation was performed as follows. With respect to PiXI and CpXI, the respective DNA fragments were synthesized using a xylose isomerase gene originated from *Piromyces* sp. E2 and a xylose isomerase gene originated from *Clostridium phytofermentans*, in which codons were optimized for expression in yeast, as templates, as well as primers listed in Table 4 (SEQ ID NOs:77, 78, 79 and 80). The obtained DNA fragments were inserted in pRS316GAP digested by restriction enzymes SacII and XhoI using an In-Fusion HD PCR cloning kit to construct pRS316GAP-PiXIO, and pRS316GAP-CpXIO (Table 3).

With respect to BtXI, the DNA fragment was synthesized using a genome DNA (ATCC 29148D) originated from *B. thetaiotaomicron* VPI 5482 furnished by ATCC (American Type Culture Collection) as a template. The used primers (SEQ ID NOs:81, 82) are listed in Table 4. The obtained DNA fragment was inserted in pRS316GAP digested by restriction enzymes SacII and XhoI using an In-Fusion HD PCR cloning kit to construct pRS316GAP-BtXI (Table 3).

With respect to LIXI, a synthetic gene LIXIO (SEQ ID NO:83), in which codons were optimized for expression in yeast, was synthesized (Genscript Corporation (www.Genscript.com)) based on an amino acid sequence described in Patent Literature 3 and an amino acid sequence acquired from Genbank (Genbank: AAD20249). Next, a DNA fragment was synthesized using the prepared LIXIO as a template, and primers listed in Table 4 (SEQ ID NOs:84, 85). The obtained DNA fragment was inserted in pRS316GAP digested by restriction enzymes SacII and XhoI using an In-Fusion HD PCR cloning kit to construct pRS316GAP-LIXIO (Table 3).

Using pRS316GAP-PiXIO, pRS316GAP-CpXIO, pRS316GAP-LIXIO and pRS316GAP-BtXI as a template, primers (SEQ ID NOs:86 to 101) listed in Table 4, and a QuickChange Lightning Multi Site-Directed Mutagenesis kit (Agilent Technologies, Inc.), a reaction was carried out according to a protocol attached to the kit. Using the obtained reaction solution, transformation of ECOS (Trademark) Competent *E. coli* DH5 alfa (Nippon Gene Co., Ltd.) was conducted, and plasmids were extracted from grown colonies. By sequencing a mutated locus was identified, and for each XI, plasmids for transducing 4 variant XI genes, in which asparagine was substituted with cysteine, threonine, valine, and alanine, were obtained (Table 3).

Then, the obtained plasmid was introduced in the W600W strain using Frozen-EZ Yeast Transformation II, and spread on an SD agar culture medium. A grown colony was streaked over a fresh SD agar culture medium and cultured to purify the colony.

Fourteenth Embodiment (Fermentation Test of Genetically Modified Yeast Utilizing Xylose as Carbon Source)

In 1 mL of SD liquid culture media prepared in a 96-well Storage Block, 20 types of recombinant yeasts listed in Table 3 were inoculated and cultured in a constant temperature incubator shaker M-BR-022UP at 30 deg C., and 1500 rpm, for 24 hours. Then 200 microliters of a culture solution was added in 1 mL of an SD liquid culture medium prepared in a fresh 96-well Storage Block and culture under similar conditions for 24 hours. Cells were recovered, washed twice with sterile water, and then suspended in sterile water to prepare a yeast suspension.

Figure 9:
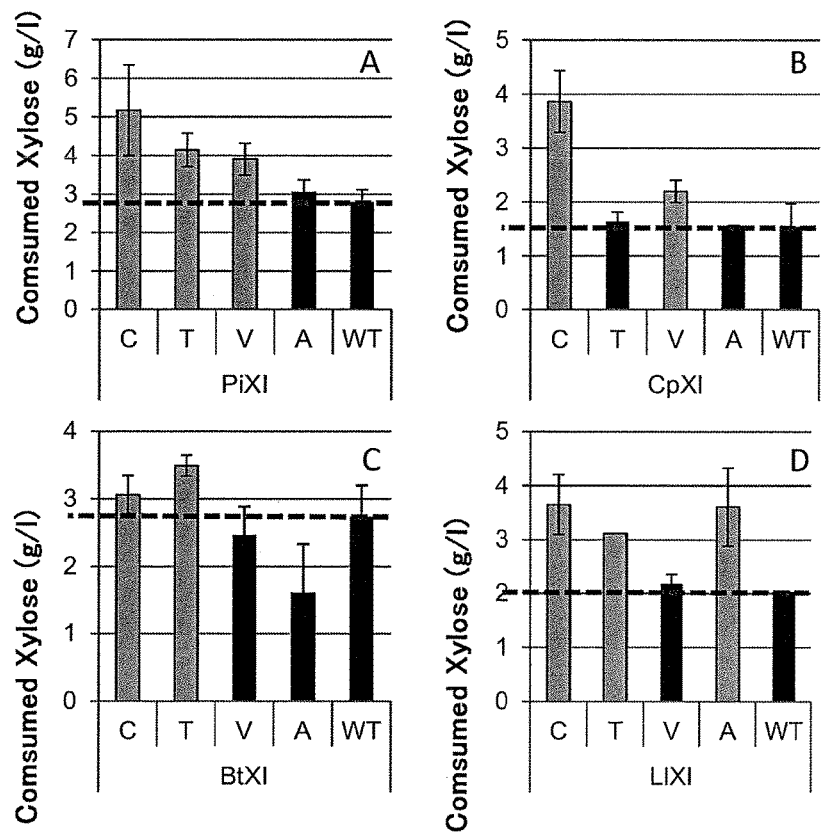
FIG. 9 is charts A to D showing fermentation test results (xylose consumption in 72 hours) with respect to various variant strains utilizing xylose as a carbon source.

A fermentation test was conducted under the following conditions. 1 mL of an SX liquid culture medium (6.7 g/L of Yeast Nitrogen Base without amino acids, and 20 g/L of xylose) was prepared in a 96-well Storage Block, in which the yeast suspension was added such that the final $OD_{600}$ of the culture medium became 10. Then, fermentation was carried out as in the Twelfth Embodiment, and xylose and ethanol were analyzed by liquid chromatography. FIG. 9 shows xylose consumptions by yeasts having introduced various XI genes from the initiation of the fermentation to 72 hours thereafter. The fermentation tests were repeated 2 or more times, and the average values are shown.

As shown in FIG. 9A, the xylose consumption after fermentation of 72 hours of the WP700s(WT) strain was 2.8 g/L, however in contrast thereto the xylose consumptions of the WP704Cs(C), the WP704 Ts(T) strain, and the WP704Vs(V) strain having introduced a mutated type XI gene, in which asparagine was substituted with cysteine, threonine, or valine, were respectively 5.1 g/L, 4.1 g/L, and 3.9 g/L to confirm improvement of the xylose utilization ability. Similarly with respect to other XIs, improvement of the xylose utilization ability was confirmed for strains having introduced mutated type XI genes, in which asparagine was substituted with cysteine or valine in the case of CpXI (FIG. 9A), cysteine or threonine in the case of BtXI (FIG. 9C), and cysteine, threonine, or alanine in the case of LIXI (FIG. 9D).

As the result of the above, it became clear that similar to RsXI also in the case of XIs originated from other organisms, such as PiXI, CpXI, BtXI, and LIXI, the xylose utilization ability of yeast could be improved by introducing a mutation at a locus corresponding to asparagine at position 337 in RsXI.

[Sequence Listing Free Text]

SEQ ID NOs: 2-13, 201-105: consensus sequence in Xylose isomerase

SEQ ID NOs: 30-40: xylose isomerase mutant

SEQ ID NOs: 41-70, 77-101: primer

SEQ ID NOs: 71-76: xylose isomerase mutant

The invention claimed is:

1. A DNA coding for a protein that has xylose isomerase activity and has an amino acid sequence including, when aligned with an amino acid sequence expressed by SEQ ID NO:1, the following 1st to 6th motifs from the N-terminus of the protein in the order described, and having, in place of asparagine (N) in an amino acid sequence of the 6th motif, an amino acid selected from the group consisting of cysteine, threonine, valine, and alanine:

1st motif: FXXXXKXXXXXXXXHDXD (SEQ ID NO:2)
        wherein X represents a naturally occurring amino acid,
    2nd motif: XXXXXXXWGGREGYXXLXNT (SEQ ID NO:3)
        wherein X represents a naturally occurring amino acid,
    3rd motif: XXXXXXXXEPKPXEPXXHQYDXD (SEQ ID NO:4)
        wherein X represents a naturally occurring amino acid,
    4th motif: LXXXXXXXNXEXNHXXLXXHXXXH (SEQ ID NO:5)
        wherein X represents a naturally occurring amino acid,
    5th motif: XGSXDXNXGXXXXGWDXDXXP (SEQ ID NO:6)
        wherein X represents a naturally occurring amino acid, and
    6th motif: GGXNFDXKXRR (SEQ ID NO:7)
        wherein X represents a naturally occurring amino acid.

2. A transformation vector for a eukaryotic cell, containing the DNA according to claim 1.

3. A eukaryotic cell retaining the DNA according to claim 1.

4. The eukaryotic cell according to claim 3, which is yeast.

5. The eukaryotic cell according to claim 4, wherein the yeast belongs to any one selected from the group consisting of *Saccharomyces, Kluyveromyces, Candida, Pichia, Schizosaccharomyces, Hancenula, Klocckera, Schwanniomyces, Yarrowia*, and *Issatchenkia*.

6. The eukaryotic cell according to claim 3, which produces secretory cellulase.

7. The eukaryotic cell according to claim 3, having an exogenous or endogenous gene that produces any one selected from the group consisting of ethanol, lactic acid, acetic acid, 1,3-propanediol, propanol, butanol, succinic acid, ethylene, glycerol, farnesol, geranylgeraniol, and squalene.

8. A method for generating a eukaryotic cell with imparted or improved xylose utilization ability, comprising a step of introducing the DNA according to claim 1 into a eukaryotic cell for transformation.

9. A method comprising culturing the eukaryotic cell according to claim 3 in the presence of xylose to form a useful substance.

10. The method according to claim 9, wherein the useful substance is any one selected from the group consisting of ethanol, lactic acid, acetic acid, 1,3-propane diol, propanol, butanol, succinic acid, ethylene, glycerol, farnecol, geranyl geraniol and squalene.

* * * * *